Figure 1:
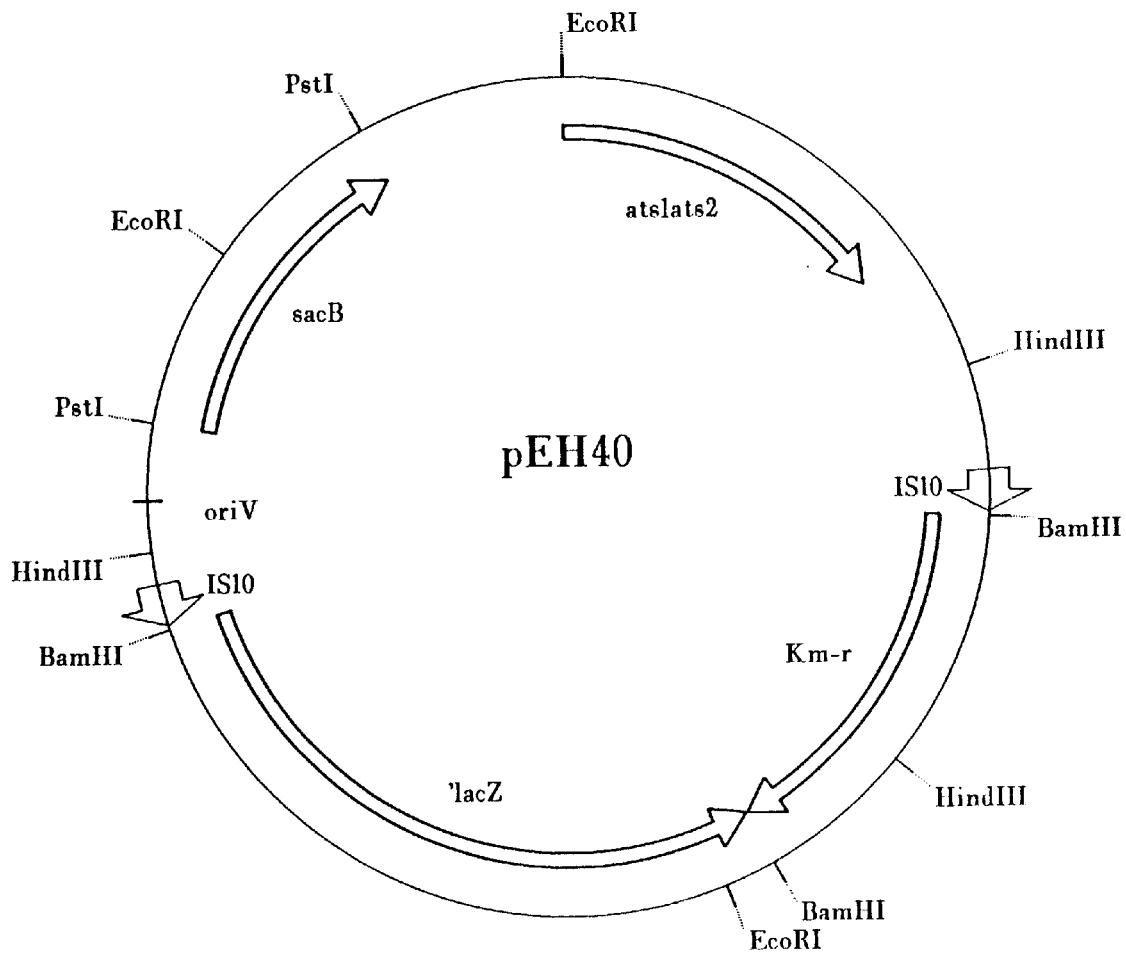

US005935782A

United States Patent [19]
Cianciotto et al.

[11] Patent Number: 5,935,782
[45] Date of Patent: Aug. 10, 1999

[54] **METHOD AND MATERIALS FOR DETECTING *LEGIONELLA PNEUMOPHILA***

[75] Inventors: Nicholas P. Cianciotto; Erin K. Hickey, both of Evanston, Ill.

[73] Assignee: Northwestern University, Evanston, Ill.

[21] Appl. No.: 08/766,858

[22] Filed: Dec. 13, 1996

Related U.S. Application Data

[60] Provisional application No. 60/011,545, Feb. 13, 1996.

[51] Int. Cl.[6] ............................ C07H 21/04; C12Q 1/68; C12P 19/34

[52] U.S. Cl. ............................ 435/6; 435/91.2; 435/810; 536/23.7; 536/24.32; 536/24.33; 935/8; 935/78

[58] Field of Search ............................ 536/23.7, 24.32, 536/24.33; 435/6, 91.2, 810; 935/8, 78

*Primary Examiner*—Carla J. Myers
*Attorney, Agent, or Firm*—Sheridan Ross P.C.

[57] ABSTRACT

The invention provides novel genes and proteins of *Legionela pneumophila*. The invention also provides methods of detecting or quantitating *L. pneumophila* using these genes, mRNAs encoded by the genes, or proteins encoded by the genes as targets. Nucleic acids designed to hybridize with the genes or mRNAs encoded by the genes, or antibodies that bind specifically to the proteins, are used in the methods, and the nucleic acids and antibodies can be provided in kits.

14 Claims, 18 Drawing Sheets

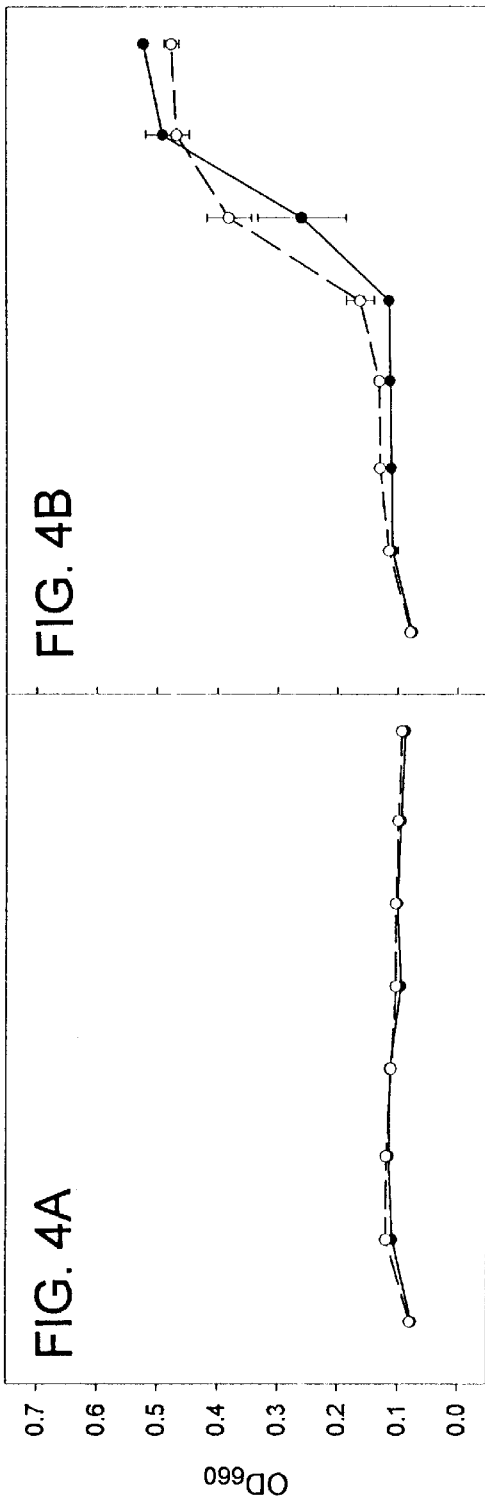
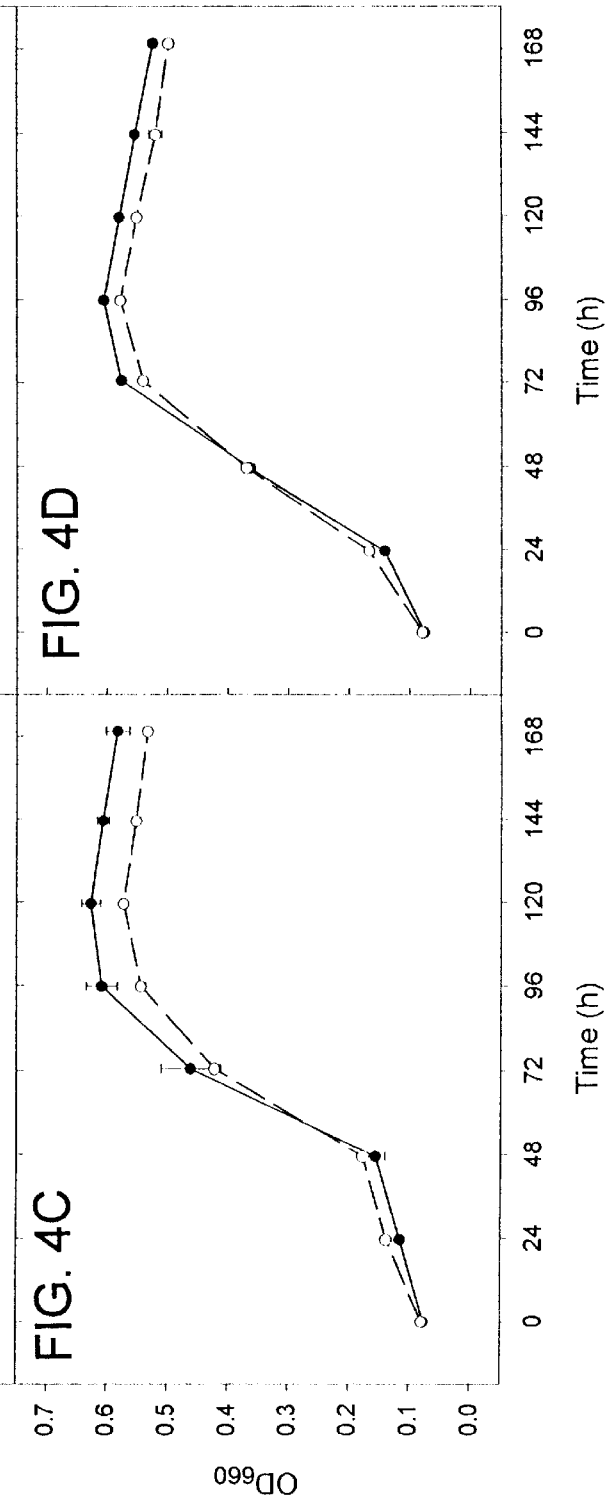
FIG. 4A  FIG. 4B  FIG. 4C  FIG. 4D

```
atttaactcagaatacagaaacttttatccaaaatcaaactctattgccaattaataat      60
            -35                        -10
attttatttgccccacctcttgcaaatgagaatgattatcattatatttaatttataac    120 aaaataatcc[ttcaggagat]aataATGGCCCTGGCGTACGGTAATTTTCATGAACTCAGC    180
                        M  A  L  A  Y  G  N  F  H  E  L  S     12

CATCAATTACGCTTTTTACTATTTGAAATTGGCATAGGACTACCACAAAATAGTGTGGAT    240
 H  Q  L  R  F  L  F  E  I  G  I  G  L  P  Q  N  S  V  D       32

TATTTTATTACCTTAGCTCATAAAAATACCCTGAAGCGTTTACAGCATGCCTCCATTAAG    300
 Y  F  I  T  L  A  H  K  N  T  L  K  R  L  Q  H  A  S  I  K    52

GAAGGATTAATTCAATCAGCCATTGCAAGTCACCATATCCATGATTTCATTGACCAATTG    360
 E  G  L  I  Q  S  A  I  A  S  H  H  I  H  D  F  I  D  Q  L    72

CAGATAAAACTGAAAAATTCAATGCCGGAAAGTAAGTTTTTTCAATGGCGAAAAATCAGG    420
 Q  I  K  L  K  N  S  M  P  E  S  K  F  F  Q  W  R  K  I  R    92

GAAGCATTAGATGAATCGATTGCCAATGAGGCTTTGGCTTACGCCTACAGGCAAAACTGG    480
 E  A  L  D  E  S  I  A  N  E  A  L  A  Y  A  Y  R  Q  N  W   112

AACACCCAATTAAGAAATGAAGCCATGCACTACAAGAGTCTGTGGACATGGATAAATAAT    540
 N  T  Q  L  R  N  E  A  M  H  Y  K  S  L  W  T  W  I  N  N   132

GAACTATCTCCGTATCAAACGTTATTATTTCTGGAACAATGGGGCAGTTTGAGGCATCCC    600
 E  L  S  P  Y  Q  T  L  L  F  L  E  Q  W  G  S  L  R  H  P   152

TATCACCCAGCATTCAGCGCAAAAACAGGGTTTACGCGAAGAGAAGTACTCCAAAACTCT    660
 Y  H  P  A  F  S  A  K  T  G  F  T  R  R  E  V  L  Q  N  S   172
       EcoRI
CCCGAATTCCAGGCCAAAGTCAGTGTACATTGGTGTGCATTAAATAAAACAAAAATTCAG    720
 P  E  F  Q  A  K  V  S  V  H  W  C  A  L  N  K  T  K  I  Q   192

TCAATAAGCCCAAAAATTGATTATGCCAACCAAATTTCTCAAGAATTTCCCAAAGAATAT    780
 S  I  S  P  K  I  D  Y  A  N  Q  I  S  Q  E  F  P  K  E  Y   212

TTTTATTGGCGTGAAAAATTGTTATTTAGCCACATCAACCCTGATGATTATTATCCAATT    840
 F  Y  W  R  E  K  L  L  F  S  H  I  N  P  D  D  Y  Y  P  I   232

CCTGTTCACCCTTGGCAGTGGAGGAATCAATTACAAATGGCGTTTGCATCTTTAATTGAT    900
 P  V  H  P  W  Q  W  R  N  Q  L  Q  M  A  F  A  S  L  I  D   252

AATAAATCCCTCATCTTGTTACCTCATCACCAAACACTAATACCTTCTTTATCACCTGAT    960
 N  K  S  L  I  L  L  P  H  H  Q  T  L  I  P  S  L  S  P  D   272

ATTATGATGCCAACACAATCCACTCAATGTACACTTAAACTGGCTACCACTTTAAGCACC   1020
 I  M  M  P  T  Q  S  T  Q  C  T  L  K  L  A  T  T  L  S  T   292

TCAATGGCTGGAAAACTTGATAATTCTAATGATATGGTATTGCTTACCAGATGGATCGAT   1080
 S  M  A  G  K  L  D  N  S  N  D  M  V  L  L  T  R  W  I  D   312

TCCCTGTTAGCAAAAACAAACTATTACCAAAATACCTTGTTTATATGTAAAAACCTGGAG   1140
 S  L  L  A  K  T  N  Y  Y  Q  N  T  L  F  I  C  K  N  L  E   332

AGCATGAGCGCCTATGATCAAACTCTCTCTGAATGCAATCGAGTAAAATTATTGTTTGGC   1200
 S  M  S  A  Y  D  Q  T  L  S  E  C  N  R  V  K  L  L  F  G   352

TTATATCAAAACCCACTCCACAAAATAAGACAGGATCAAAGAGCAGTTCCATTACCTGCC   1260
 L  Y  Q  N  P  L  H  K  I  R  Q  D  Q  R  A  V  P  L  P  A   372

CTATTAACTGATTCCCCTTGTAGCAATACACCATTACTCATTGAAATTATTAAAGCTAGC   1320
 L  L  T  D  S  P  C  S  N  T  P  L  L  I  E  I  I  K  A  S   392
```

FIG. 7A

```
GGCCTGCACCCAACGACTTATTTCACTGAATATTGTTATAAGATGTTATTTGGACAATTG  1380
 G   L   H   P   T   T   Y   F   T   E   Y   C   Y   K   M   L   F   G   Q   L     412

CATCTATTGCTAAAATATGGATTAGCACTAGAAGTGGAGCAACACAATATTTTAGTCATC  1440
 H   L   L   K   Y   G   L   A   L   E   V   E   Q   H   N   I   L   V   I     432

TTCGATGACAATAAACCTCAGGGGATAATTATAAAAGAGCCAAACAACCTTAAGCTATGC  1500
 F   D   D   N   K   P   Q   G   I   I   I   K   E   P   N   N   L   K   L   C   452

AATCATGAACTGTTTAAAAACGTTCAAAAACCCAACGCTCCAGACTCTTTATCCATCTAT  1560
 N   H   E   L   F   K   N   V   Q   K   P   N   A   P   D   S   L   S   I   Y   472

ACAAAAGATCTTAATCAGGTTAGAACCCTTTTCATCCAGGGAACATTAAAAAATCATCTA  1620
 T   K   D   L   N   Q   V   R   T   L   F   I   Q   G   T   L   K   N   H   L   492

CATCACTTGATTGGCTGTTTACGTAATGAGTATCAGATTCCTTCAAGAACCTTATGGGGA  1680
 H   H   L   I   G   C   L   R   N   E   Y   Q   I   P   S   R   T   L   W   G   512

TTAGCTCGCCAAGTCATGCAAACTGTATTTAAAGACTTATCCAAAGACATTGATCCGCGT  1740
 L   A   R   Q   V   M   Q   T   V   F   K   D   L   S   K   D   I   D   P   R   532

ATTCTAAGTTGGCAACAACATCTATTGCTTCATGATAACTGGGAGCATCAACCTGAATTG  1800
 I   L   S   W   Q   Q   H   L   L   L   H   D   N   W   E   H   Q   P   E   L   552

TTATTAAGTCTGCATTCCAAAATCAATCGAAATATTACAATAAAGGAATACAACCCATTA  1860
 L   L   S   L   H   S   K   I   N   R   N   I   T   I   K   E   Y   N   P   L   572

TCAGAGATCTAAgctctactggacttacgaaaaacccatgcgctcttgttccaatacta  1920
 S   E   I   -                                                                    575
                XhoI
aaatatgagaacttctcgaggccgggatgtggatactatgagtcaataaatcccaattga  1980
```

FIG. 7B

```
IucA   MILPSEKSATDVAAQCFLNALIRETKDWQIAEY------PPDELIIPLDE      -44
       | |            || |     . .|
FrgA   MALAYGNFHELSHQLRFLLFEIGIGLPQNSVDY---FITLAHKNTLKRLQ      -47
                   |.      ..|    |  .           ..
IucC   M---------NHKDWDLVNRRLVAKMLSELEYEQVFHAESQGDDRYCIN      -40

IucA   QKSLHFRVAYFSPTQHHRFAFPAHLVTASGSYPVDFTTLSRLIIDKLRHQ      -94
       |.     . .  ||      |  .                       |
FrgA   HASIKEGLIQSAIASHHIHDFIDQLQIKLKNSMPESKFFQWRKIREALDE      -97
                  |.     .  |..        ..
IucC   LPGAQWRFIAERGIWGWLWIDAQTLRCADEPVLAQTLLMQLKQVLSMSDA      -90

IucA   LFLPVPLCETFHQRVLESYAHTQQTIDARHDW---AILREKALNFGEAEQ      -141
       |   ..    |           . |            .| |
FrgA   SIANEALAYAYRQNWNTQLRNEAMHYKSLWTWINNELSPYQTLLFLEQWG      -147
       ..|     |  .|      |.        .|  |..
IucC   TVAEHM------QDLYATLLGDLQLLKARRGLSASDLINLNADRLQCLLS      -134

IucA   ALLTGHAFHPAPKSHEPFNRQEAERYLFDMAPHFPLRWFSVDKT------      -185
        .|   ||.|||  .   | | |      |.    |  ..         ||
FrgA   SL--PHPYHPAFSAKTGFTRREVLQNSPEFQAKVSVHWCALNKT------      -189
            | |    |                  .||.         .|| |..
IucC   G----HPKFVNKGRRGWGKEALERYAPEYANTFRLHWLAVKREHMIWRC      -180

IucA   QIAGESLHLNLQQRLTR------FAAENAPQLLNELSDNQWLFPLRPWQG      -229
       |   |.  .  ..|     |          |.  |||
FrgA   KIQSISPKIDYANQISQEFPKEYFYWREKLLFSHINHDDYYPIPVHPWQW      -239
             .|  |||  .        |  |.|||||||
IucC   DNEMDIHQLLTAAMDPQEFARFSQVWQENGL-----DHNWLPLPVHPWQW      -225

IucA   EYLFQQVWCQALFAKGLIRDLG--EAGTSWLPTTSSRSLYCATSRDMIKF      -277
          |.          |  |||
FrgA   RNQLQMAFASLIDNKSLILLPH--HQT---LIPSLSPDIMMPTQSTQCTL      -284
       |                 . .   |     |
IucC   QEKIATDFIADFGEGRMVSLGEFGDQ---WLAQQSLRTLTNASRRGGLDI      -272

IucA   SLSVRLTNSVRTLSVKE---VERGMRLARLAQTDGWQMLQAREPTFRVMQ      -324
       | . |. |.          .
FrgA   KLATTLSTSMAGKLDNS---NDMVLLTRWIDSLLAKTNYYQNTLFICKNL      -331
       ||  |.         .      |.||.  .|    ..  |
IucC   KLPLTIYNTSCYRGIPGRYIAAGPLASRWLQQVFATDATLVQSGAV--IL      -320

IucA   EDDWTGLRDLNGNIMQESLFSPAWKTLLLEQPQSQ--------TNVLVSL      -366
       |  .  |     ||  |                          . |.|
FrgA   ESMSAYDQTLSECNRVKLLFGLYQNPLHKIRQDQR-------AVPLPAL      -373
       .|       |     | |                 ||         |  |
IucC   GEPAAGYVSHEGYAALARAPYRYQEMLGVIWRENPCRWLKPDESPFLMAT      -370

IucA   TQAGPHGGDSLLVSAVKRLSDRLGITVQQAAHAWVDAYCQQVLKPLFTAE      -416
           ||.      .       .        |||    .||   | . |
FrgA   LTDSPCSNTPLLIEIIK-------ASGLHPTIYFTEYCYKMLFGQLHLL      -415
       ||||.|||    .||             |||     |         |||
IucC   LMEWDENNQPLAGAYID-------RSGLDAETWLTQLFRVVVVPLYHLL      -412

IucA   ADYGLVLLAHQQNILVQMLGDLPVGFIYRL-CQGSAFMPHATEWLDTIDE      -465
       ||| |    | ||| |         . |    |    |  |
FrgA   LKYGLALEVEQHNILVIFDDNKPQGIIIKE-PHNLKLCNH--ELFKNVQK      -462
       || ||.|  ||||||   |  |   . .|    ..|    |
IucC   CRYGVALIAHGQNITLAMKEGVPQRVLLKDFQGDMRLVKE--EF------      -454
```

FIG. 8A

```
        AQAENIFTREQLLRYFPYYLLVNSTFAVTAA--LGAAGLDSEANLMAR-V  -512
         .|    .       |..|             |   |  ..  | .
FrgA    PNAPDSLSIYTKDLNQVRTLFIQGTLKNHLH--HLIGCLRNEYQIPSRTL  -510
         |||      .. |  .      |  |   |  . ||          |
IucC    -PEMDSLP---QEVRDVTSRLSADYLIHDLQTGHFVTVLRFISPLMVRL-  -499

IucA    RTLLAEVRDQVTHKTCLNYVLESPYWNVKGNFFCYLNDHNENTIVDPSVI  -562
         |   |   |          |.      |    |  .     |   | |
FrgA    WGLARQVMQTVFKDLSKDIDPRILSWQQHLLLHDNWEHQPELLLSLHSKI  -560
         |   | |  .                    |        |    .| |
IucC    -----GVPERRFYQLLAAV------------LSDYMKKHPQMSERFALFSLF  -534

IucA    Y--FDFANPLQAQEV       -575
                      |.
FrgA    NRNITIKEYNPLSEI       -575
         .|        ||
IucC    RPQIIRVVLNP           -545
```

FIG. 8B frgA is species-specific

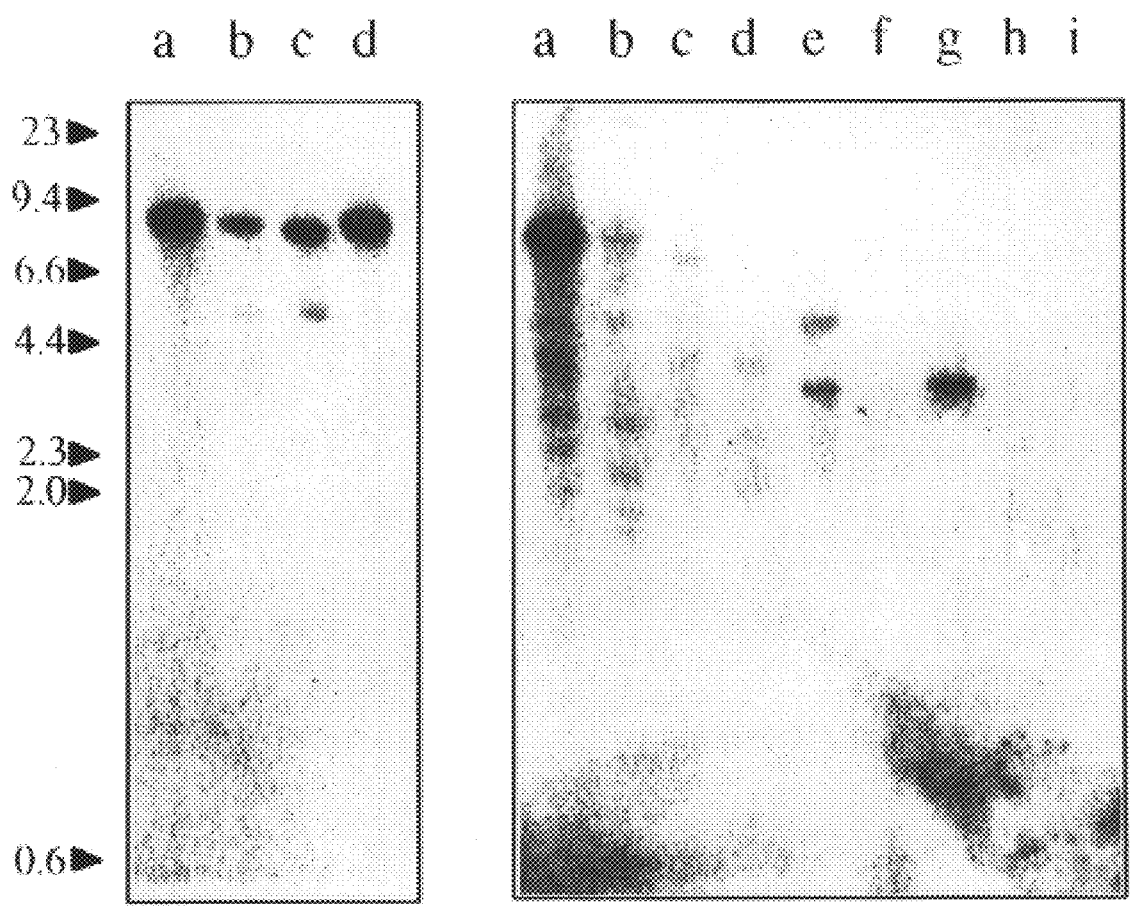

METHOD AND MATERIALS FOR DETECTING *LEGIONELLA PNEUMOPHILA*

Benefit of provisional application 60/011,545, filed Feb. 13, 1996, is hereby claimed.

This invention was made, in part, under Public Health Service Grants AI30064 and AI34937 from the National Institutes of Health. The government may have certain rights in the invention.

BACKGROUND

*Legionela pneumophila*, the agent of Legionnaires' disease, exists in many environments such as human alveolar macrophages, fresh water protozoa, and biofilms. Cianciotto, et al., *Mol. Biol. Med.* 6:409–424 (1989); Dowling, et al., *Microbiol. Rev.* 56:32–60 (1992); Fields, *Trends Genet*. 4:286–290 (1996); Horwitz, Curr. Top. *Microbiol Immunol*. 181:265–282 (1992). To survive, the bacterium must obtain essential nutrients from its environment, and the capacity to sense the availability of a particular nutrient may be important for the regulation of its uptake. Iron is essential for *L. pneumophila* growth both extracellularly and intracellularly [Byrd and Horwitz, *J. Clin. Invest.* 83:1457–1465 (1989); Feely, et al., *J. Clin. Microbiol.* 8:320–325 (1978); James, et al., *Infect. Immun.* 63:4224–4230 (1995); Pine, et al., *J. Clin Microbiol.* 9:615–626 (1979); Pope, et al., *Infect. Immun.* 64:629–36 (1996); Reeves, et al., *J. Clin Microbiol.* 13:688–695 (1981)], serving as a co-factor for an aconitase, a superoxide dismutase, and other enzymes [Hoffman, in Legionella: Proceedings of the 2nd International Symposium, *American Society for Microbiology*, Washington, D.C., p. 61–67 (Thornsberry, et al. eds., 1984); Mengaud and Horwitz, *J. Bacteriol.* 175:5666–5676 (1993); Steinman, *Mol. Gen. Genet*. 232:427–430 (1992)]. *L. pneumophila* requires 3–13 μM ferric iron for extracellular growth, a level that is relatively high compared to other bacteria. Hoffman, in Legionella: Proceedings of the 2nd International Symposium, American Society for Microbiology, Washington, D.C., p. 61–67 (Thornsberry, et al. eds., 1984); James, et al., *Infect. Immun.* 63:4224–4230 (1995); Johnson, et al., *Infect. Immun.* 59:2376–2381 (1991); Mengaud, et al., *J. Bacteriol.* 175:5666–5676 (1993); Pine, et al., *J. Clin Microbiol.* 9:615–626 (1979); Reeves, et al., *J. Bacteriol.* 154:324–329 (1983); Ristroph, et al., *J. Clin. Microbiol.* 13:115–119 (1981). However, iron within the macrophage host is either bound by transferrin, complexed as ferritin, or sequestered in the labile iron and heme pools. Bridges, in *Iron storage and transport*, CRC Press, Boca Raton, pp. 297–314 (Ponka, et al. eds., 1990); Crichton and Charloteaux-Wauters, *Eur. J. Biochem.* 164:485–506 (1987); Muller-Eberhard and Nikkila, *Semin. Hematol.* 26:86–104 (1989). Thus, the intraphagosomal *L. pneumophila* likely has evolved strategies for scavenging scarce free-iron or iron bound to cellular chelators. However, the ways in which *L. pneumophila* obtains iron from its environment remain unknown. High affinity siderophores that are commonly used for $Fe^{3+}$ assimilation by other bacteria are reported to be absent from the legionellae. Liles and Cianciotto, *Infect Immun.* 64:1873–1875 (1996); Reeves, et al., *J. Bacteriol.* 154:324–329 (1983). Also, this bacterium does not bind and utilize transferrin or lactoferrin. Bortner, et al., *Can. J. Microbiol.* 35:1048–1051 (1989); Byrd and Horwitz, *J. Clin. Invest.* 83:1457–1465 (1989); Byrd and Horwitz, *J. Clin Invest.* 88:1103–1112 (1991); Johnson, et al., *Infect. Immun.* 59:2376–2381 (1991); Quinn and Weisberg, *Curr. Microbiol.* 17:111–116 (1989). *L. pneumophila* does, however, express two internal ferric reductases which likely process internalized $Fe^{3+}$. Johnson, et al., *Infect. Immun.* 59:2376–2381 (1991); Poch and Johnson, *Biometals* 6:107–114 (1993). Undoubtedly, the legionellae have multiple iron uptake systems, like so many other pathogens. Guerinot, *Annu. Rev. Microbiol.* 48:743–72 (1994); Otto, et al., *Crit. Rev. Microbiol.* 18:217–233 (1992); Payne, *Trends Microbiol.* 1:66–69 (1993); Wooldridge and Williams, *FEMS Microbiol Rev.* 12:325–348 (1993).

In other bacteria, the factors involved in iron uptake, such as siderophores and transferrin receptors, are regulated by the repressor protein Fur. Bagg and Neilands, *Biochemistry* 26:5471–5477 (1987); de Lorenzo, et al., *J. Bacteriol.* 169:2624–2630 (1987); Guerinot, *Annu. Rev. Microbiol.* 48:743–72 (1994); Litwin, *Clin. Microbiol. Rev.* 6:137–149 (1993); Tsolis, et al., *J. Bacteriol.* 177:4628–37 (1995). In the presence of ferrous iron, the Fur dimer binds to promoter regions and represses the transcription of iron acquisition genes. Bagg and Neilands, *Biochemistry* 26:5471–5477 (1987); Hantke, *Mol. Gen. Genet.* 182:228–292 (1981). However, when the availability of iron is low, Fur does not bind and the genes are expressed. In addition to the controlling factors involved in iron uptake, Fur represses variety of other virulence determinants, such as exotoxin A in *Pseudomonas aeruginosa* and a hemolysin in *Vibrio cholerae.* Litwin, et al., *J. Bacteriol.* 174:1897–1903 (1992); Prince, et al., *J. Bacteriol.* 175:2589–2598 (1993).

Recently, the *L. pneumophila* fur gene was isolated and its predicted amino acid sequence was shown to be 50–60% identical to that of other bacteria. Hickey and Cianciotto, *Gene* 143:117–121 (1994). Furthermore, the cloned fur encoded a protein able to repress *Escherichia coil fiu* expression and decrease enterobactin production. These data suggested that *L. pneumophila* iron acquisition is regulated by Fur using the concentration of iron in the environment as a signal for when to repress gene expression.

A number of pathogens, including both intra- and extracellular parasites, have evolved mechanisms for interacting with hemin and heme-containing compounds. Otto, et al., *Crit. Rev. Microbiol.*, 18:217–233 (1992); Wooldridge and Williams, *FEMS Microbiol. Rev.* 12:325–348 (1993). This interaction can serve several functions. First, and perhaps most often, it serves as a means for iron acquisition. Strains of Aeromonas spp., *Bacteroides fragilis, Bordetella pertussis, Campylobacter jejuni, Escherichia coli, Haemophilus ducreyi, Haemophilus influenzae, Helicobacter pylori, Klebsiella pneumoniae, Neisseria gonorrheae, Neisseria meningitidis, Plesiomonas shigelloides, Porphyromonas gingivalis, Serrati marcescens, Shigella flexneri, Streptococcus pneumoniae, Vibrio cholerae, Vibrio vulnificus, Yersinia enterocolitica*, and *Yersinia pestis* scavenge the iron from hemin and related substances. Daskaleros and Payne, *Infect. Immun.* 55:1393–1398 (1987); Daskaleros, et al., *Infect. Immun.* 59:2706–2711 (1991); Genco, et al., *Infect. Immun.* 62:2885–2892 (994); Lee, *J. Med. Microbiol.* 34:317–322 (1991); Letoffe, et al., *Proc. Natl. Acad. Sci. USA*, 91:9876–9880 (1994); Massad, et al., *J. Gen. Microbiol.* 137:237–241 (1991); Otto, et al., *Crit. Rev. Microbiol.* 18:217–233 (1992); Tal, et al., *Infect. Immun.* 61:5401–5405 (1993); Wooldridge and Williams, *FEMS Microbiol. Rev.* 12:325–348 (1993); Worst, et al., *Infect. Immun.* 63:4161–4165 (1995). Second, in *H. influenzae* and *P. gingivalis*, heme structures are absolutely required as sources for porphyrin rings. Carman, et al. *Infect. Immun.* 58:4016–4019 (1990); Cope, et al., *J. Bacteriol.* 177:2644–2653 (1995). Third, hemin binding to a bacterial surface may facilitate infection of eukaryotic cells. For example, in *S. flexneri* and enteroinvasive *E. coli*, it enhances invasion of epithelial cells, whereas in *Aeromonas salmonicida*, hemin interaction with S-layer proteins promotes macrophage association. Daskaleros and Payne, *Infect. Immun.* 55:1393–1398 (1987); Garduno and Kay, *Infect. Immun.* 60:4612–4620 (1992); Stugard, et al., *Infect. Immun.* 57:3534–3539 (1989). Fourth, hemin (heme) serves as a cofactor for intracellular cytochromes and enzymes; e.g., the heme-binding FixL of *Rhizobium meliloti* is an oxygen-sensing membrane kinase. Monson, et al., *Proc. Natl. Acad. Sci. USA* 89:4280–4284 (1992). Finally, *Y. pestis* has an extraordinary capacity to store hemin. Perry, *Trends Microbiol.* 1:142–147 (1993). In recent years, a number of investigators have turned their attention toward the molecular and genetic bases of hemin binding and utilization. This complex process generally involves the concerted effort of surface/outer membrane receptors and periplasmic/inner membrane transporters and has been characterized as a TonB-dependent uptake event. Bramanti and Holt, *J. Bacteriol.* 175:7413–7420 (1993); Cope, et al., *J. Bacteriol.* 177:2644–2653 (1995); Elkins, et al., *Infect. Immun.* 63:2194–2200 (1995); Hanson and Hansen, *Mol. Microbiol.* 5:267–278 (1991); Henderson and Payne, *J. Bacteriol.* 176:3269–3277 (1994); Lewis and Dyer, *J. Bacteriol.* 177:1299–1306 (1995); Mills and Payne, *J. Bacteriol.* 177:3004–3009 (1995); Stojiljkovic and Hantke, *Mol. Microbiol.* 13:719–732 (1994). In *S. marcescens*, heme acquisition is initiated by an extracellular heme-binding protein. Letoffe, et al., *Proc. Natl. Acad. Sci. USA* 91:9876–9880 (1994).

The relationship between *L. pneumophila* and hemin has received very little attention. Although ferric/ferrous iron clearly plays a critical role in extra- and intracellular Legionella growth, [Byrd and Horwitz, *J. Clin. Invest.* 83:1457–1465 (1989); Feeley, et al., *J. Clin. Microbiol.* 8:320–325 (1978); Gebran, et al., *Infect. Immun.* 62:564–568 (1994); Quinn and Weisberg, *Curr. Microbiol.* 17:111–116 (1988); Reeves, et al., *J. Clin. Microbiol.* 13:688–695 (1981)], the role of hemin is unclear. Several early studies demonstrated bacterial growth on complex and semi-defined media which contained hemin or hemoglobin supplements. Feeley, et al., *J. Clin. Microbiol.* 8:320–325 (1978); Pine, et al., *J. Clin. Microbiol.* 9:615–626 (1979). However, since the heme compounds were easily replaced with ferric salts, it was assumed that they were not required for Legionella growth. Feeley, et al., *J. Clin. Microbiol.* 8:320–325 (1978). This idea was later confirmed by the development of defined media which completely lacked hemin but supported effective *L. pneumophila* replication. Reeves, et al., *J. Clin. Microbiol.* 13:688–695 (1981); Ristroph, et al., *J. Clin. Microbiol.* 13:115–119 (1981); Warren and Miller, *J. Clin. Microbiol.* 10:50–55 (1979). Nevertheless, hemin and hemoglobin did enhance *L. pneumophila* growth on several types of complex media. Current protocols in molecular biology (Ausubel, et al., eds., 1987); Johnson, et al., *J. Clin. Microbiol.* 15:342–344 (1982). In one study, the growth of seven *L. pneumophila* strains, representing six serogroups, was stimulated by ≧100-fold by the addition of hemin to a yeast extract phosphate (YP) medium. Johnson, et al., *J. Clin. Microbiol.* 15:342–344 (1982). Taken together, these data suggest that hemin can serve as an accessory iron source.

SUMMARY OF THE INVENTION

Figure 3A:
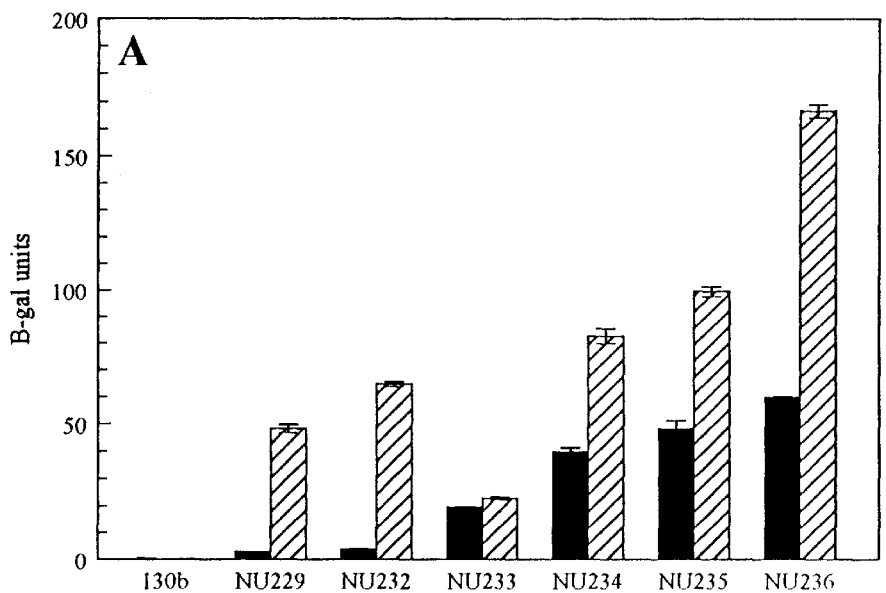
Figure 3B:
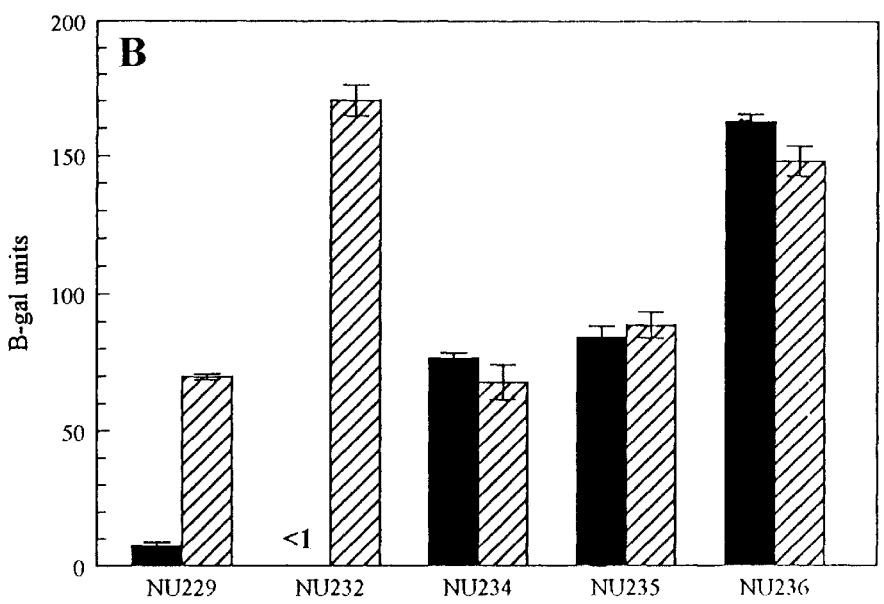

The invention comprises the frgA genes of *Legionella pneumophila*. FrgA is conserved in, and is specific to, *L. pneumophila*. Thus, the invention also comprises methods and materials for detecting *L. pneumophila*, the methods and materials being targeted to a frgA gene, an mRNA encoded by a frgA gene, or a frgA protein. The materials include frgA-specific probes and polymerase chain reaction (PCR) primers and antibodies that bind specifically to frgA proteins. The materials may be supplied in kit form.

The invention also comprises the hbp gene of *L. pneumophila*. The gene is found almost exclusively in *L. pneumophila*, and the invention comprises other methods and materials for detecting *L. pneumophila*, the methods and materials being targeted to an hbp gene, an mRNA encoded by a hbp gene, or an hbp protein. These materials include hbp-specific probes and PCR primers and antibodies that bind specifically to hbp proteins. The materials may also be supplied in kit form.

The frgA and hbp genes are exceptional for their unique, limited distribution among legionellae. All previously identified *L. pneumophila* genes, including flaA, fur, htp, lly, mip, omps, and pplA (pal), have had homologs in all or virtually all other Legionella species. Bender, et al., *Infect. Immun.* 59:3333–6 (1991); Cianciotto, et al., *Infect Immun.* 58:2912–2918 (1990); Heuner, et al., *Infect. Immun.* 63:2499–507 (1995); Hickey and Cianciotto, *Gene* 143:117–121 (1994); Hoffman, et al., *Infect. Immun.* 57:1731–1739 (1989); Hoffman, et al., *J. Bacteriol.* 174:914–920 (1992); Ott, et al., *Microb. Pathog.* 11:357–65 (1991).

BRIEF DESCRIPTION OF THE DRAWINGS

FIG. 1. Map of plasmid pEH40, the plasmid used for miniTn10'lacZ mutagenesis of *L. pneumophila*. The ca. 10-kb pEH40 contains: i) a miniTn10 (see IS10 elements) which carries a promoterless lacZ ('lacZ) and a kanamycin-resistance gene (Km-r); ii) a doubly mutated Tn10 transposase gene (atsIats2) which promotes increased variability of the transposon insertions compared to the wild-type transposase [Kleckner, et al., in *Methods in Enzymology*, 204, p. 139–180 (Miller ed. 1991)]; iii) the counterselectable levansucrase gene of *Bacillus subtilis* (sacB) [Cianciotto, et al., *FEMS Microbiol. Letts.* 56:203–208 (1988)]; and iv) a ColE1 origin of replication (oriV). Key restriction sites are indicated.

FIG. 2. Southern blots. Genomic DNAs of strains NU229 through NU236, created by miniTn10'lacZ insertions in *L. pneumophila*, were digested with HindIII, electrophoresed, and hybridized with pEH40. Lanes: A, NU229; B, NU230; C, NU231; D, NU232; E, NU233; F, NU234; G, NU235; and H, NU236. Molecular weight markers, in kb, are indicated on the left. Since HindIII cuts asymmetrically within miniTn10'lacZ (see FIG. 1), one hybridizing fragment appears more intense than the other within each lane. The intensity of the bands varied between the lanes because not all lanes contained identical amounts of DNA. Although the hybridizing bands in lane C do not appear, in this gel, to comigrate with those in lanes A and B, additional blots using HindIII and EcoRI digested DNAs illustrate that the corresponding strains do have identical insertions. Note that lane F has a faint second band at approximately 2.1-kb, while lane H has one at approximately 12-kb.

FIGS. 3A–B. Graphs of β-galactosidase production in *L. pneumophila* lacZ fusion strains. Strains were grown for 48 hours on buffered-charcoal-yeast-extract (BCYE) agar with the standard iron supplement (solid bars) or on BCYE agar with a ferric iron chelator (hatched bars). Whereas the experiment depicted in FIG. 3A utilized 50 μM iron chelator deferoxamine mesylate (DFX), the one in FIG. 3B used 52

μM iron chelator ethylenediamine di(o-hydroxyphenylacetic acid) (EDDA). FIGS. 3A and 3B are representative of two and three separate trials, respectively. In every trial, all samples were tested in triplicate.

FIGS. 4A–D. Graphs of $OD_{660}$ versus time. Wild-type strain 130b (●) and mutant strain NU229 (○) were grown in chemically defined medium (CDM) with increasing iron concentrations. FIGS. 4A–D depict growth of cultures containing 0, 4, 8, and 16 μM of added iron, respectively. Bacteria used to inoculate the cultures had been grown overnight in buffered-yeast-extract (BYE) broth without the iron supplement and washed once with CDM (0 μM added iron). Growth was estimated by measuring the $OD_{660}$ of the culture over a 7-day period. FIGS. 4A–D are representative of three separate trials, and each timepoint is the average of two separate cultures. Growth in CDM containing a 20 μM iron supplement was not different from growth with medium having 60 μM iron (data not shown).

Figure 5A:
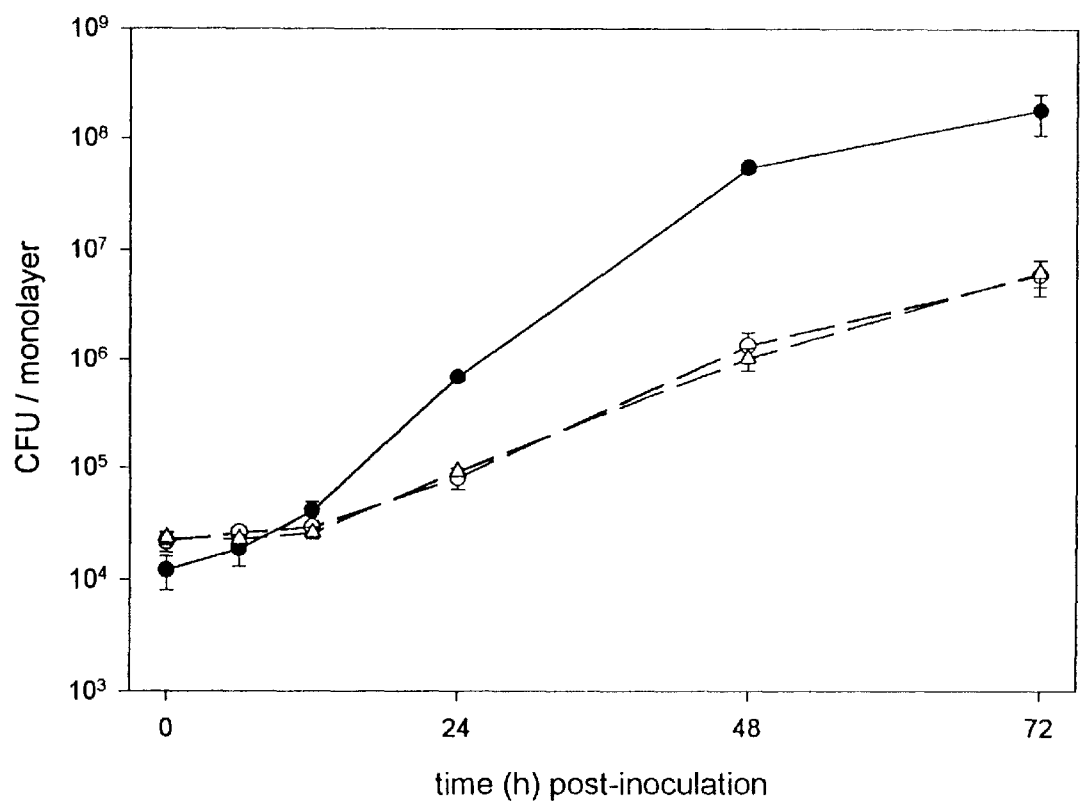
Figure 5B:
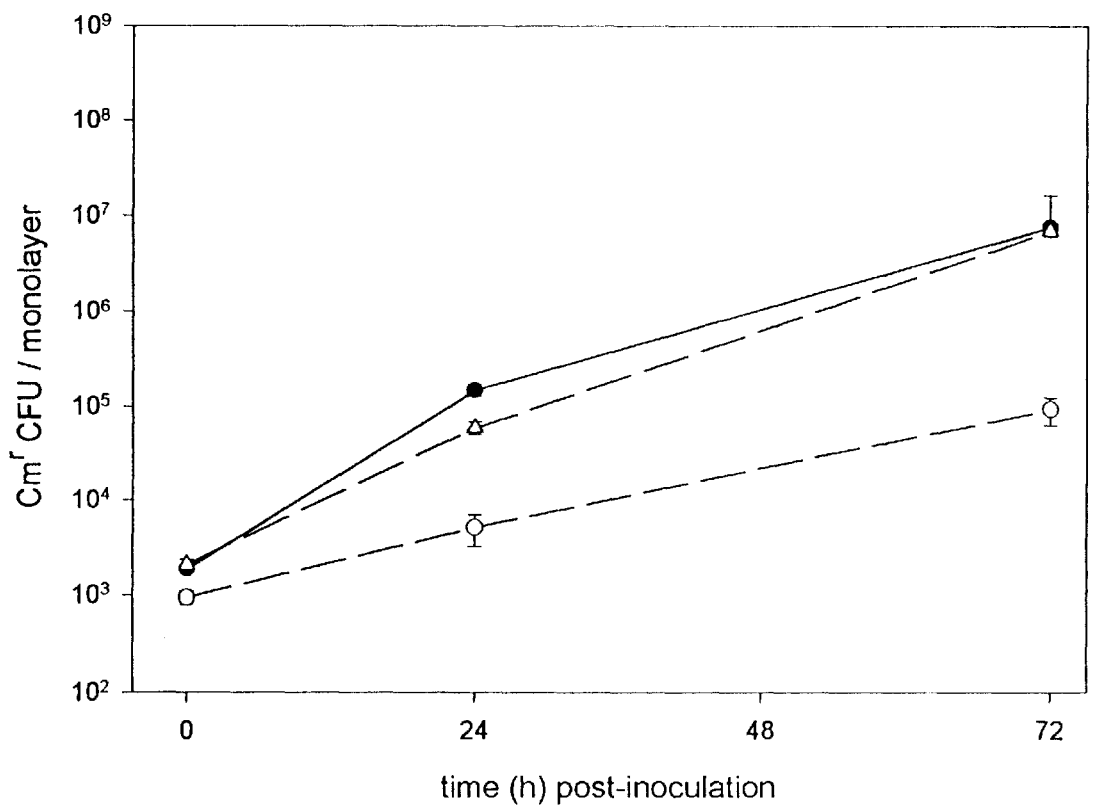

FIGS. 5A–B. Graphs of colony forming units (CFU) per monolayer versus time after inoculation of U937 cells with L. pneumophila mutants. In FIG. 5A, the monolayers (n=4) were inoculated with $10^6$ CFU of either strain 130b (●), strain NU229 (○), or strain NU229 R (Δ). After various incubation periods, the numbers of bacteria were determined. In FIG. 5B, the U937 cells were inoculated with $10^6$ CFU of either 130b(pSU2719) (●), NU229 (pSU2719) (○), or NU229 R(pEH75) (Δ). All time-points represent the mean CFU recovered, and vertical bars indicate standard deviation. The differences in the recoveries of these strains were significant at all timepoints without overlapping error bars (P<0.01, Student's t-test).

Figure 6:
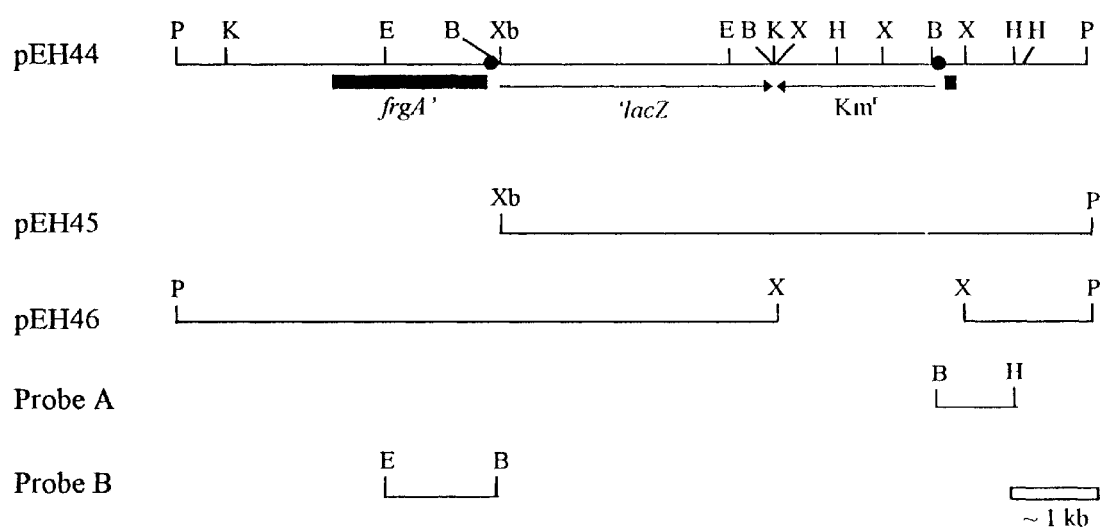

FIG. 6. Restriction map of the L. pneumophila DNA containing the interrupted frgA gene. The cloned 12-kb region containing L. pneumophila DNA and the transposon insert is depicted on the top line. The transposon consists of the thin arrows, which represent the 'lacZ and $Km^r$ genes, and the black circles indicating the location of the IS10 elements. The thick line flanking the transposon represent the interrupted frgA gene. Probe B is frgA specific, containing only frgA DNA in addition to the IS10 element. Restriction enzymes' abbreviations are BamHI (B), EcoRI (E), HindIII (H), KpnI (K), PstI (P), XbaI (Xb), and XhoI (X).

FIG. 7. DNA and predicted amino acid sequences of L. pneumophila frgA [SEQ ID NO:4]. The potential ribosome binding site is boxed. The -35 and -10 regions are in bold and labeled. Two overlapping ironboxes are underlined or double-underlined and have 4 or 5 mismatches, respectively. The target sequence that was duplicated as a result of miniTn10'lacZ insertion is indicated with a black box. Recognition sites for EcoRI and XhoI are labeled and italicized. The L. pneumophila frgA sequence has been deposited in the GenBank database at the National Center for Biotechnology Information (NCBI) under accession number U76559.

FIG. 8. comparison of sequence of FrgA of L. pneumophila with sequences of IucA and IucC of E. coli [SEQ ID NOS:6–44]. The E. coli sequences were reported previously. Martinez, et al., J. Mol. Biol. 238:288–293 (1994). Identical amino acids are indicated with a vertical line, while similar amino acids, as defined by PCGene, are indicated with a black circle. The three boxed and three shaded regions show the homologous sequences indicated in the BLASTX results from the NCBI. In these regions only, additional conserved amino acids, as defined by the BLAST program, are indicated with a small, lowered dot. Note that these regions overlap the areas that are most similar between IucA and IucC. Martinez, et al., J. Mol. Biol. 238:288–293 (1994).

Figure 9:
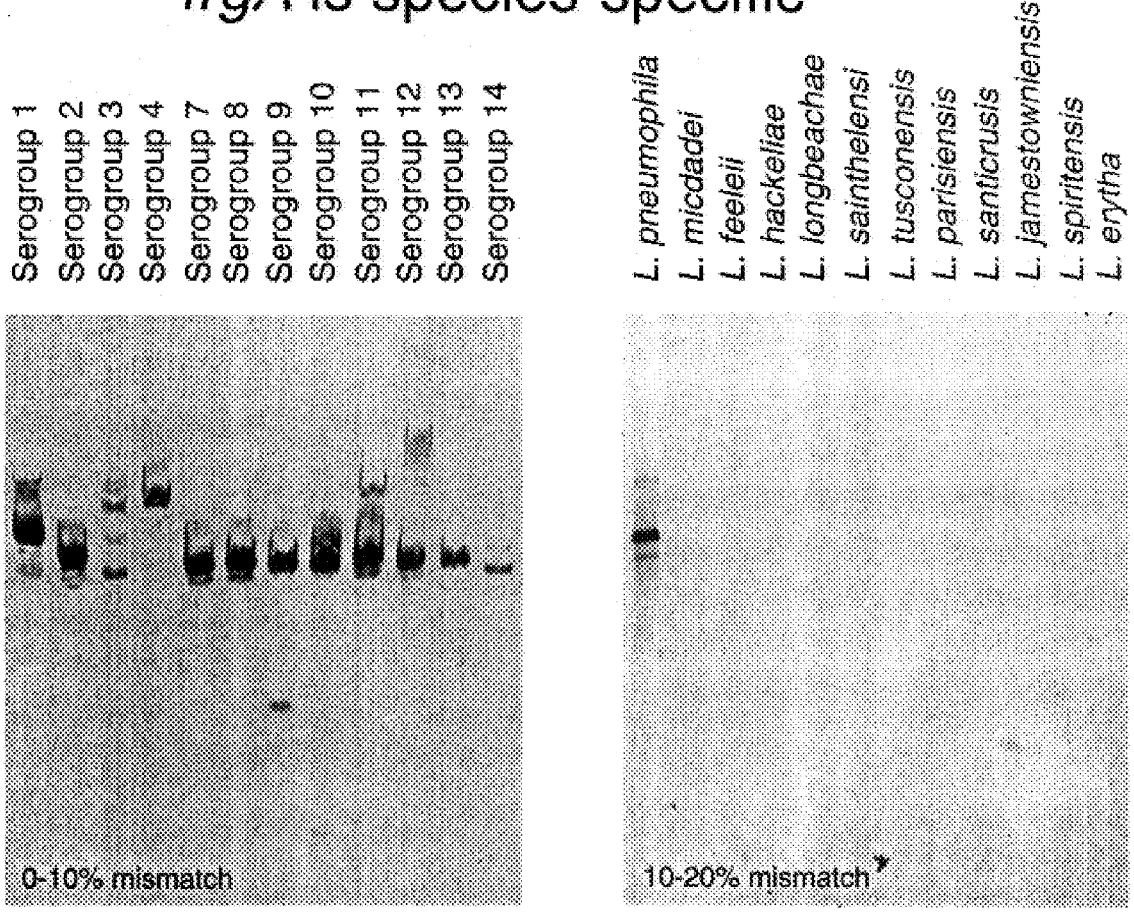

FIG. 9. Southern blots showing hybridization of DNAs from Legionella species with an frgA probe. DNAs were digested and electrophoresed through 0.8% agarose. A Southern blot was then hybridized with probe B (see FIG. 6) under high-stringency (left half of figure) and low-stringency (right half of figure) conditions.

Figure 10:
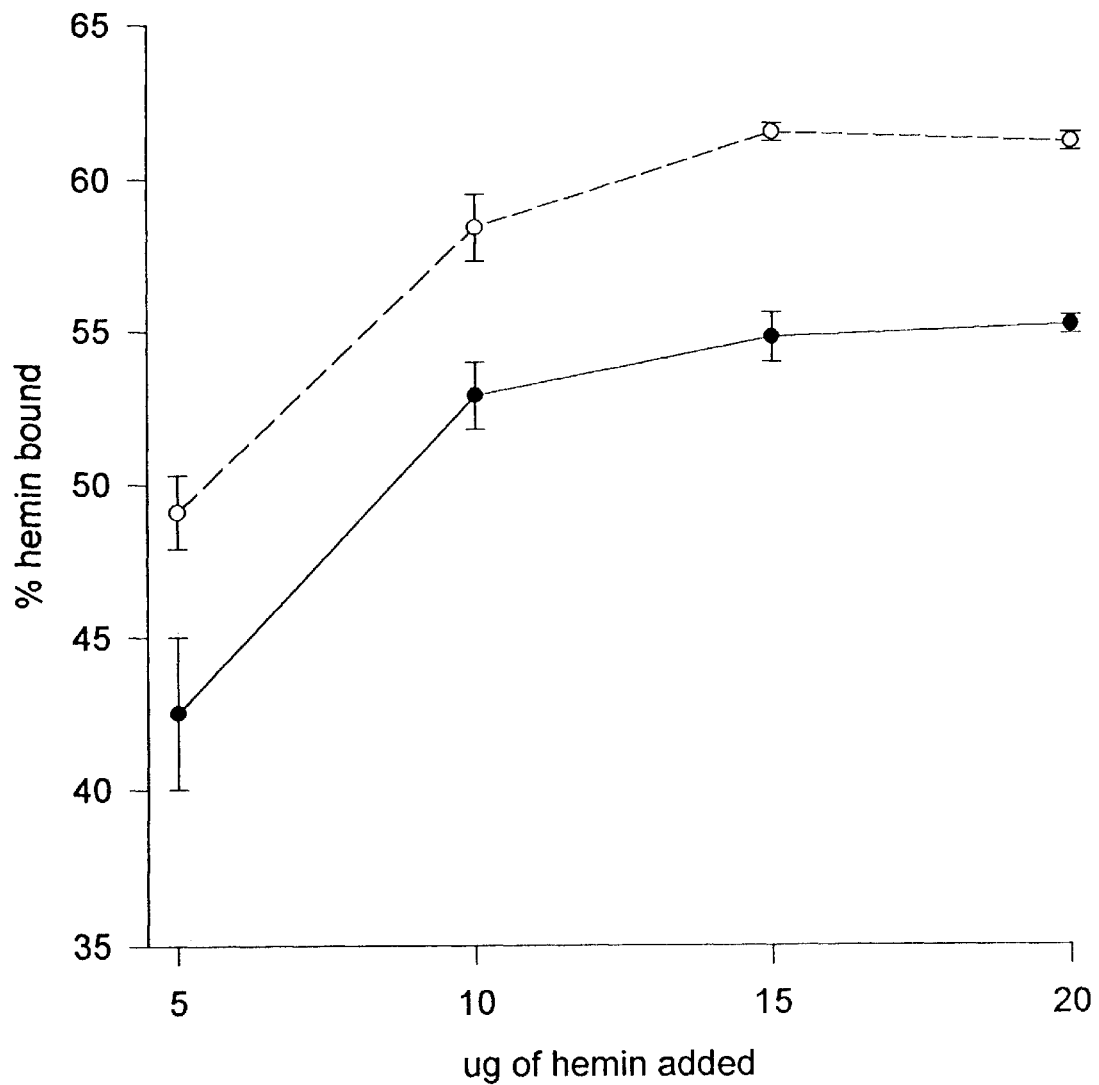

FIG. 10. Graph of % hemin bound by wild-type L. pneumophila versus the amount of hemin. A total of $1.0 \times 10^8$ CFU of strain 130b obtained from YP-minus-Fe-plus-hemin agar (○) and $1.6 \times 10^8$ CFU harvested from BCYE agar (574) were assayed for their ability to remove hemin from the solution. Each datum point represents the mean percent hemin bound for three replicate cultures, and the vertical bars denote the standard deviations. The differences in binding between the YP-minus-Fe-plus-hemin and BCYE cultures were significant at each hemin concentration (P=<0.001 for all concentrations except 5 μg. for which P=<0.01 [Student's t test].

Figure 11A:
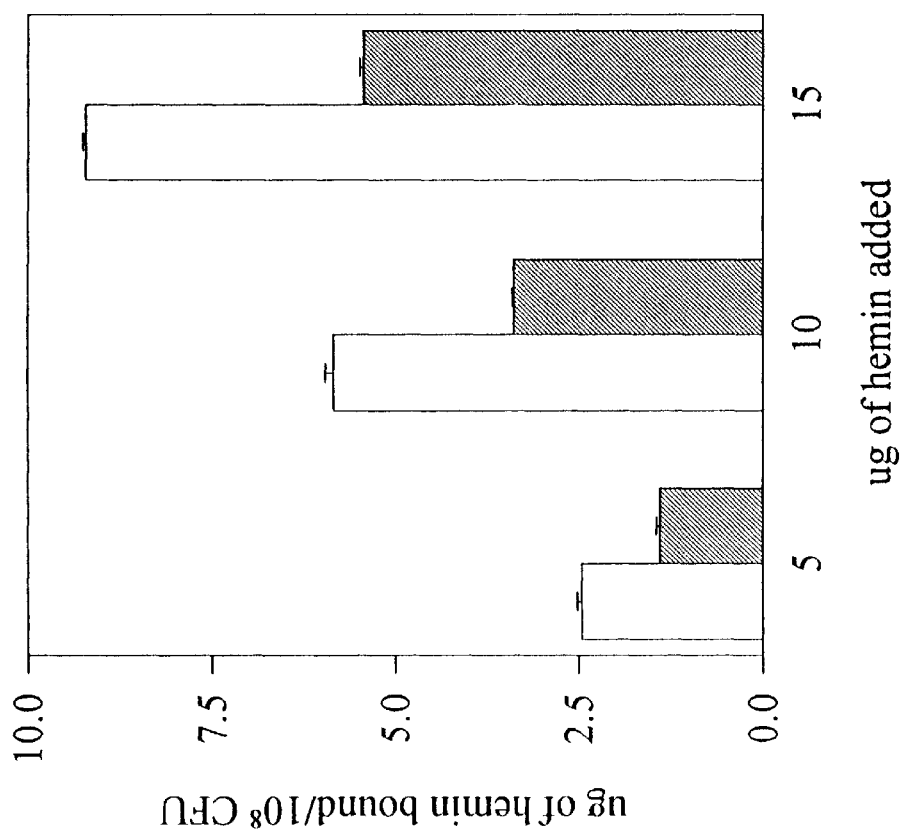
Figure 11B:
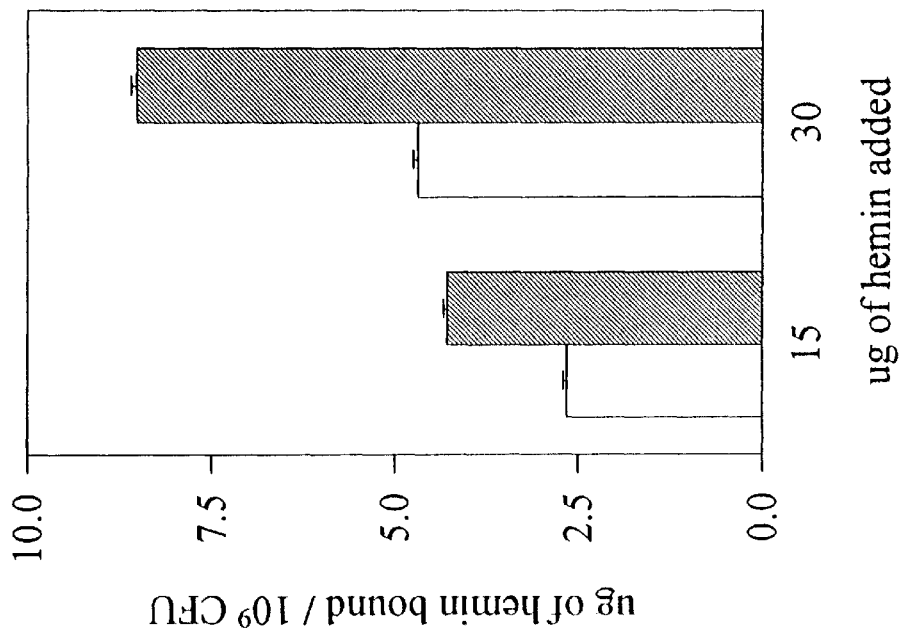

FIGS. 11A–B. Graphs of hemin bound by recombinant E. coli and mutant L. pneumophila versus amount of hemin added. FIG. 11A: E. coli HB101(pBR322) (open box) and HB101(pEH1) (shaded box) were grown to stationary phase in M9CA salts broth, and then about $10^9$ CFU of each were assayed for their ability to remove hemin from solution. Each datum point represents the mean binding for three replicate cultures, and the vertical bars denote the standard deviations. The differences in binding between the two strains were significant at both hemin concentrations (P=<0.001 [Student's t test]). HB101(pEH2) and HB101 (pBOC3) exhibited hemin-binding capacities that were comparable to that of HB101(pEH1) (data not shown). FIG. 11B. L. pneumophila 130b (open box) and NU226 (shaded box) were grown on YP-minus-Fe-plus-hemin agar plates, and then about $10^8$ CFU were assayed for hemin binding. Significant differences in binding were evident at all hemin concentrations, including the 20-μg/ml level not depicted here (P=<0.001 [Student's t test]).

Figure 12:
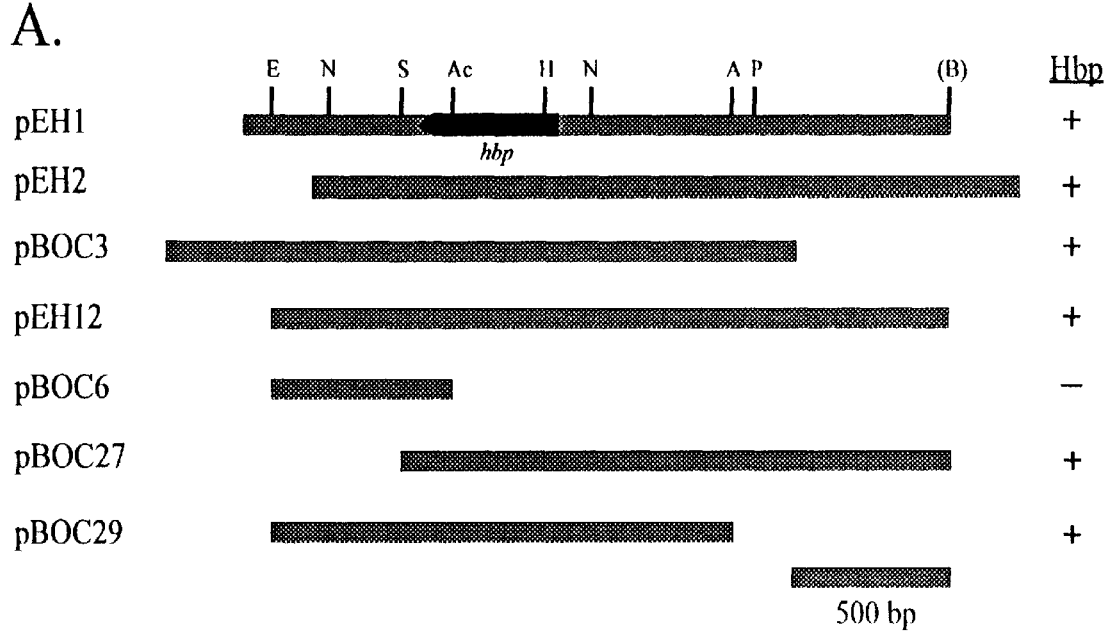

FIG. 12. Identification of the L. pneumophila hbp ORF; restriction maps and phenotypes for pEH1 and its subclones. All recombinant plasmids represent Legionella DNA cloned into pBR322+ and -, the HB101 transformant was or was not pigmented on agar media containing hemin or Congo red, respectively. Restriction enzyme recognition sites are indicated as follows: A, AflIII; Ac, AccI; B, BamHI; E, EcoRI; H, HincII; N, NdeI; P, PstI; and S, SacI.

Figure 13A:
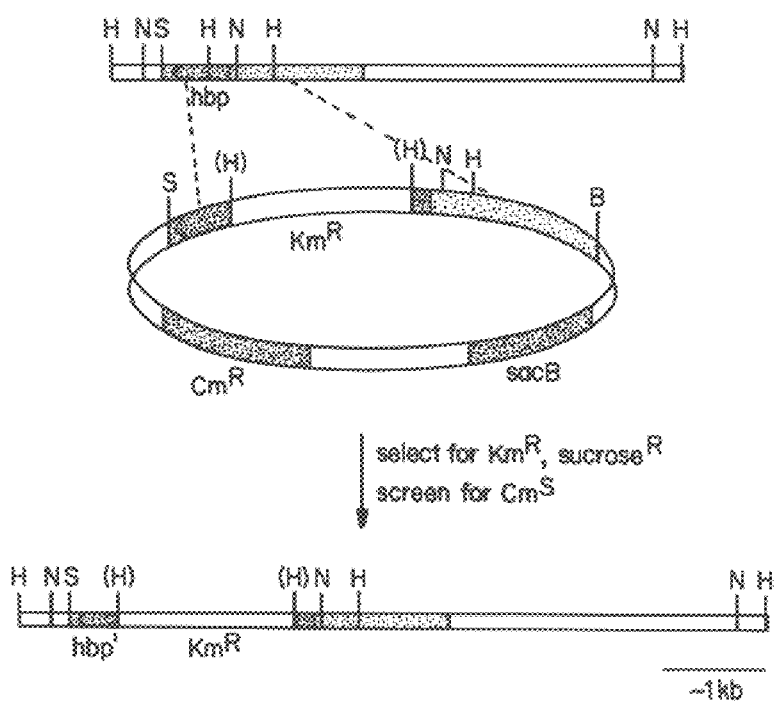
Figure 13B:
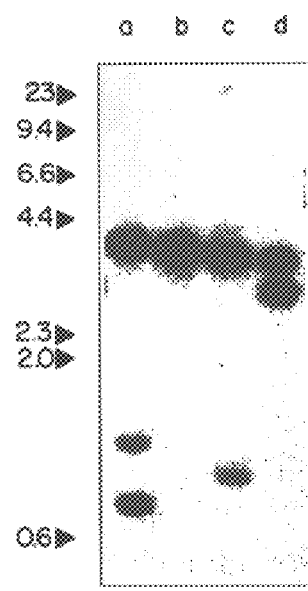

FIGS. 13A–B. Mutagenesis of the hbp gene of L. pneumophila. FIG. 13A: Diagram of the mutagenesis procedure. The top half depicts a pBOC22-containing L. pneumophila transformant. The dashed line indicates a double-crossover event between the plasmid and the chromosome. The predicted result of this recombination, with the mutated hbp replacing the wild-type gene, is shown at the bottom. The locations of BamHI, HincII, NdeI, and SacI recognition sites are indicated. (H), the HincII site that was lost upon insertion of $Km^r$ into hpb. FIG. 13B: Demonstration of allelic exchange by Southern hybridization analysis. Genomic DNAs were digested with either HincII (lanes a and b) or NdeI (lanes c and d) and were probed with $^{32}$P-labeled pBOC22. Strain 130b appears in lanes a and c, and strain NU226 is represented in lanes b and d. The migrations and sizes (in kilobases) of molecular markers are indicated.

Figure 14:
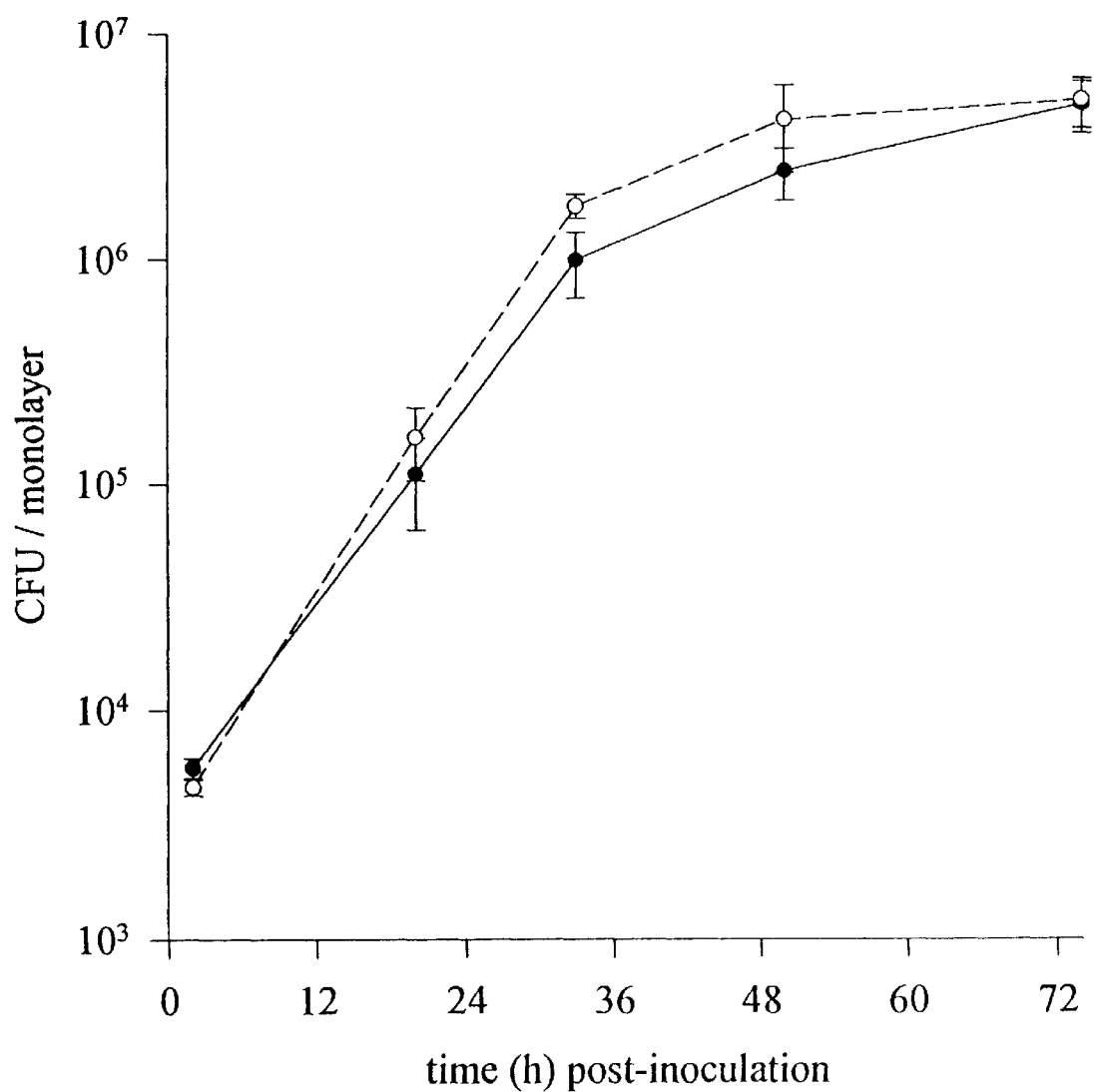

FIG. 14. Graph of CFU per monolayer versus time post-inoculation for intracellular infection of U937 cells by strains of L. pneumophila. U937 cell monolayers (n=4) were inoculated with $10^5$ CFU of either strain 130(b) (●) or strain NU226 (○), and after various incubation periods, the numbers of viable intracellular bacteria were determined. Since 2 h were allowed for bacterial attachment and entry, the first sample that was collected is presented as a 2-h datum point. Each point represents the mean CFU recovered, and the vertical bars indicate the standard deviations.

FIGS. 15A–B. Southern blots showing hybridization of DNAs from Legionella species with an hbp probe. DNAs were digested with EcoRI and electrophoresed through 0.8% agarose. A Southern blot was then hybridized with the hbp-containing NdeI-EcoRV fragment of pEH12 under high- (FIG. 15A) and low- (FIG. 15B) stringency conditions. FIG. 15A: Lanes: a and b, *L. pneumophila* serogroup 1 strains 130b and Philadelphia 1, respectively; c and d, *L. pneumophila* serogroups 8 and 13, respectively. FIG. 15B: Lanes: a, *L. pneumophila* 130b; b, *L. micdadei*; c, *L. erthyra*; d, *L. fee produce antibodies useful in the immunoassay by methods well known in the art. A frgA gene or fragment thereof may be used to produce a frgA protein or peptide. Peptides can also be prepared by solid phase synthetic methods. Single chain or other engineered antibodies or fragments of antibodies containing an antibody combining site can be also used.

To perform the immunoassay, a sample suspected of containing L. pneumophila is contacted with the antibody under conditions so that the antibody can bind to a frgA protein, if present. Since frgA proteins are believed not to be found on the surface of L. pneumophila, the cells will likely have to be lysed to release the protein. Standard immunoassay formats can be used. The antibody bound to the frgA protein may be labeled to allow for detection or quantitation of the frgA protein, or a labeled moiety that binds to the antibody (e.g., a secondary antibody directed to the first antibody or protein A) may be used. Suitable labels and methods of attaching them to antibodies and other proteins and compounds are well known. Suitable labels include radioactive labels (e.g., $^{125}I$), fluorescent labels (e.g., fluorescein, rhodamine), chemiluminescent labels, particulate labels (e.g., gold colloids), colorimetric labels (e.g., dyes), enzymes, and biotin.

Reagents useful for detecting or quantifying *L. pneumophila* by immunoassay may also be supplied as a kit. The kit will comprise at least one container holding an antibody that binds specifically to a frgA protein. The kit may contain other reagents and equipment useful in performing immunoassays, including buffers, containers (e.g., test tubes, culture plates), substrates for enzyme labels, labeled streptavidin or avidin to bind to a biotin label, etc.

The invention further provides an hbp gene of *L. pneumophila*. In particular, Example 2 describes the identification, isolation and characterization of the hbp gene of *L. pneumophila* strain 130b. Southern hybridization analysis using this gene showed that hbp genes are found almost exclusively in *L. pneumophila* strains. Under low stringency conditions, weak hybridization of an hbp probe to genes in two Legionella species was observed. The sequence of the coding region of the hbp gene of strain 130b and portions of the flanking regions is given in Chart A [SEQ ID NO:45].

As used herein an "hbp gene" is an *L. pneumophila* gene that hybridizes to the hbp gene of strain 130b, or a fragment thereof at least 18 bp in length, under conditions of high stringency.

Hbp genes other than the hbp gene of strain 130b can be identified and isolated using methods well known in the art. For instance, probes based on the sequence of the hbp gene of strain 130b can be used to screen *L. pneumophila* genomic libraries for other hbp genes.

Since, as noted above, hbp genes are found almost exclusively in *L. pneumophila* strains, hbp genes, and the mRNAs and proteins encoded by them, are good targets for the detection or quantitation of *L. pneumophila* strains. For instance, *L. pneumophila* may be detected or quantitated by polymerase chain reaction (PCR) using primers that will amplify at least a portion of an hbp gene, by the use of DNA or RNA probes that will hybridize to an hbp gene or mRNA, or by an immunoassay using antibodies that bind specifically to a hbp protein. In particular, if high-stringency conditions are used for hybridizing probes to an hbp gene, mRNA or PCR-amplified DNA, the assays will differentiate *L. pneumophila* from other Legionella species (see Example 2). Also, the use of hbp-specific probes should also enhance the specificity of PCR assays as compared to current assays using primers directed to genes found in all Legionella species (see Example 2, particularly the final paragraph). These assays are performed as described above for the frgA gene, mRNA and protein. Also, reagents for performing these assays are the same as described above, except that they are targeted to an hbp gene, an mRNA encoded by an hbp gene, or an hbp protein. The reagents may be supplied in kit form as described above.

Samples that may be used in the methods of the invention include water samples and clinical samples. Water samples may be taken from any source, including plumbing fixtures, evaporative condensers, cooling towers and supplies of potable water (e.g., lakes and rivers). Clinical samples include sputum, throat swabs, blood, urine, cerebrospinal fluid, skin, biopsies, saliva, synovial fluid, bronchial lavages, or other tissue or fluid samples from humans or other animals.

Many of the procedures described above utilize hybridization of nucleic acids. Hybridization conditions and guidelines for selecting high- and low-stringency conditions are well known in the art. See, e.g., Sambrook et al., *Molecular Cloning: A Laboratory Manual* (2nd ed. 1989). Suitable hybridization conditions can be readily determined and optimized using only ordinary skill in the art.

The above-described assays targeted to a frgA gene, an MRNA encoded by a frgA gene, or a frgA protein, or to an hbp gene, an MRNA encoded by an hbp gene, or an hbp protein may be used alone or in combination with each other or with other tests to detect or quantitate *L. pneumophila*. For instance, a PCR assay could utilize primers directed to a gene common to all Legionella in combination with primers directed to the frgA gene which is specific to *L. pneumophila*.

EXAMPLES

Example 1

Cloning and Mutation of *L. pneumophila* frg Genes

Using a new random mutagenesis protocol, the *L. pneumophila* loci that are regulated by iron were identified. In particular, wild-type *L. pneumophila* strain Wadsworth 130b was randomly mutated with a miniTn10'lacZ transposon. The resulting gene fusions were tested for iron-regulation by assessing β-galactosidase production in the presence and absence of iron chelators. Of the initial six mutants with iron-repressed lacZ fusions, two strains, NU229 and NU232, possessed fusions that were stably iron-regulated.

To assay for Fur regulation, the levels of β-galactosidase were measured in strains no longer producing Fur. As in a number of pathogenic bacteria, *L. pneumophila* fur could not be insertionally inactivated, but spontaneous $Fur^-$ derivatives were generated by selecting for manganese resistance. Strain NU229 contained a Fur-repressed fusion based on derepression of lacZ expression in its manganese-resistant derivative. Extracellular growth of NU229 in bacteriological media was similar to that of wild-type strain 130b.

To assess the role of an iron- and Fur-regulated (frgA) gene in intracellular infection, the ability of NU229 to grow within U937 cell monolayers was tested. Quantitative infection assays demonstrated that NU229 was impaired as much as 80-fold in intracellular growth. Reconstruction of the mutant by allelic exchange proved that the infectivity defect in NU229 was due to the inactivation of frgA and not a second-site mutation. Subsequently, complementation of the interrupted gene by an intact plasmid-encoded gene demonstrated that the infectivity defect was due to the loss of frgA and not a polar effect.

Nucleotide sequence analysis revealed that the 63 kD FrgA has homology with the aerobactin synthetases IucA and IucC of *Escherichia coli*, raising the possibility that *L. pneumophila* encodes a siderophore which is required for optimal intracellular replication.

Southern hybridization analysis determined that frgA is specific to the *L. pneumophila* species and is not found in other Legionella species.

Portions of this work were previously presented. Hickey and Cianciotto, in *Abstracts of the 95th General Meeting of the American Society for Microbiology*, Abstract B-375, page 230 (1995).

A. Materials and Methods

1. Bacterial Strains, Media, and Chemicals. The *L. pneumophila* frg genes were cloned from and inactivated within serogroup 1 strain 130b. Other *L. pneumophila* strains tested for the presence of frgA included serogroup 2 strain ATCC 33154, serogroup 3 strain ATCC 33155, serogroup 4 strain ATCC 33156, serogroup 7 strain ATCC 33823, serogroup 8 strain ATCC 35096, serogroup 13 strain B2A3105, serogroup 14 strain 1169-MN-H, as well as representatives of serogroups 9–12, that were obtained from the Michigan Department of Public Health. Cianciotto, et al., *Infect Immun*. 58:2912–2918 (1990). Other Legionella species examined include *L. birminghamensis* 1407-AL-H, *L. dumoffii* ATCC 33279, *L. erytha* SE-32A, *L. gormanii* ATCC 33297, *L. feeleii* WO-44C, *L. hackeliae* Lansing 2, *L. israelensis* Bercovier 4, *L. jamestowniensis* JA-26, *L. longbeachae* ATCC 33462, *L. micdadei* Rivera, *L. oakridgensis* OR-10, *L. parisiensis* PF-209, *L. sainthelensi* Mt. St. Helen's 4, *L. santicrusis* SC-63, *L. spiritensis* MSH-9, and *L. tucsoniensis* 1087-AZ-H. Cianciotto, et al., *Infect Immun*. 58:2912–2918 (1990).

All Legionella strains were grown at 37° C. on buffered-charcoal-yeast-extract (BCYE) agar for 48–72 hours or within buffered-yeast-extract (BYE) broth. Cianciotto, et al., *Infect Immun*. 58:2912–2918 (1990). When appropriate, 25 µg/ml kanamycin, 3 µg/ml chloramphenicol, 5%(w/v) sucrose, or 0.5 µg/ml streptonigrin was added to the medium. To select and maintain *L. pneumophila* Fur mutants, 0.4–0.6 mM manganese chloride was added to BCYE instead of the iron supplement. To generate low-iron BCYE, 50–60 µM of deferoxamine mesylate (DFX) or 50–80 µM of ethylenediamine di(o-hydoxyphenylacetic acid) (EDDA) was added in place of the standard 355 µM ferric pyrophosphate supplement. These levels of $Fe^{3+}$ chelators did not significantly inhibit bacterial growth. Chemically defined medium (CDM) and acid washed glassware were used for monitoring *L. pneumophila* growth kinetics in liquid. Reeves, et al., *J. Bacteriol*. 154:324–329 (1983). The indicated concentrations of iron within CDM were achieved by adding ferric pyrophosphate supplements. *E. coli* strain HB101 served as a host for recombinant plasmids and was grown on Luria-Bertani agar containing 50 µg/ml kanamycin, 50 µg/ml ampicillin, or 30 µg/ml chloramphenicol. Current protocols in molecular biology (Ausubel, et al., eds. 1987). Unless stated otherwise, all chemicals were obtained from Sigma Chemical Co., St. Louis, Mo.

2. Random Mutagenesis of *L. pneumophila* with MiniTn10'lacZ

To identify *L. pneumophila* genes regulated by iron, promoterless lacZ ('lacZ) genes were randomly inserted into the 130b chromosome. Plasmid pEH40 (FIG. 1), which was used to introduce miniTn10'lacZ into *L. pneumophila* was constructed in two steps. First, a 'lacZ cassette, isolated from BamHI-digested pNK2804, was ligated to the BglII site in the miniTn10 of pGI6145. Kleckner, et al., in *Methods in Enzymology*, 204, 139–180 (Miller, ed. 1991). Then, the resulting plasmid was digested with PstI and ligated with the sacB-containing PstI fragment from pUCD800+oriT. Cianciotto, et al., *FEMS Microbiol. Letts*. 56:203–208 (1988).

To isolate miniTn10'lacZ-containing legionellae, pEH40 was electroporated into strain 130b, and transformants were selected on BCYE agar containing kanamycin and sucrose. Cianciotto, et al., *Proc. Natl. Acad. Sci. USA* 89:5188–5191 (1992); Pope, et al., *FEMS Microbiol. Letts*. 124:107–112 (1994). The frequency of kanamycin-resistant ($Km^r$), sucrose-resistant colonies was $6.4 \times 10^{-6}$, suggesting that the transposition frequency of miniTn10'lacZ is comparable to that of miniTn10 without 'lacZ. Pope, et al., *FEMS Microbiol. Letts*. 124:107–112 (1994). To identify those mutants that produced β-galactosidase, the base plates were topped with 0.7% agar containing 0.6 mg/ml 5-bromo-4-chloro-3-indolyl-beta-D-galactopyranoside puriss (XGAL). Miller, *Experiments in Molecular Genetics* (1972). Approximately 46% of $Km^r$, sucrose-resistant colonies exhibited blue pigmentation. To quantitate the degree of lacZ expression in *L. pneumophila*, β-galactosidase activity was measured as described in Miller, *Experiments in Molecular Genetics* (1972). In preparation for the assay, strains were grown for 48–72 hours on BCYE agar and then suspended in sterile water to an optical density at 660 nm ($OD_{660}$) of 0.4–0.7.

3. Directed Mutagenesis and Trans-complementation of *L. pneumophila*.

To mutate specific genes in the *L. pneumophila* chromosome, the cloned genes, inactivated with $Km^r$ inserts, were ligated into the counterselectable pEA75, and allelic exchange was performed as described previously. Cianciotto, et al., *FEMS Microbiol. Letts*. 56:203–208 (1988); O'Connell, et al., *Infect. Immun*. 63:2840–2845 (1995). For attempts at interrupting *L. pneumophila* fur, the cloned gene was obtained from plasmid pEH22a. Hickey and Cianciotto, *Gene* 143:117–121 (1994). To complement a chromosomal mutation, the relevant *L. pneumophila* gene was cloned into the pACYC184 derivative pSU2719, transferred into the mutant by electroporation, and maintained with chloramphenicol selection. Cianciotto, et al., *FEMS Microbiol. Letts*. 56:203–208 (1988); Martinez, et al., *Gene* 68:159–162 (1988).

4. Isolation of *L. pneumophila* Genomic DNA.

Genomic DNA was isolated from *L. pneumophila* strains using a protocol adapted from Neumann, et al., *Trends Genet*. 8:332–333 (1992). The bacteria were swabbed from a fresh agar plate and resuspended in 1 ml of sterile water. After a 2 minute centrifugation (16,000×g), the bacterial pellet was suspended in 0.5 ml SET (75 mM NaCl, 25 mM EDTA, 20 mM Tris pH 7.5) containing 1 mg/ml lysozyme and 0.1 mg/ml RNase A. The mixture was incubated for 30 minutes at 37° C. before adding 0.1 volumes of 10% sodium dodecyl sulfate (SDS) and 0.05 volumes of 20 mg/ml Proteinase K. Following incubation at 55° C. for 2 hours, one third volume of NaCl-saturated water was added to the tube. Next, one volume of 0.1M Tris (pH 8)-equilibrated phenol was added, and the mixture incubated at room temperature for 30 minutes using a rotator. The phases were separated by a 5-minute centrifugation (16,000×g), and the aqueous phase was removed to a new tube. Two additional extractions were performed using 1 volume of phenol/chloroform/isoamyl alcohol (25:24:1) and then 1 volume of chloroform/isoamyl alcohol (24:1). Finally, after removing the aqueous phase to a new tube, the DNA was precipitated by adding 1 volume of isopropanol.

5. DNA Hybridizations.

For Southern blot hybridizations, genomic DNAs from L. pneumophila strains were digested with restriction enzymes according to the manufacturer's protocols (New England Biolabs, Beverly, Mass.). DNAs were then electrophoresed through 0.8% agarose and transferred to a nitrocellulose filter. Current protocols in molecular biology (Ausubel et al., eds., 1987). Digoxigenin-labeling of the indicated probes and high-stringency hybridizations (i.e., ca. 10% basepair mismatch) were performed using the Genius System v2.0 (Boehringer Mannheim, Indianapolis, Ind.). Two modifications were made to the Genius System protocols to achieve low stringency conditions (i.e., ca. 30% basepair mismatch). First, the hybridization and wash temperatures were dropped to 49° C. and, second, the sodium chloride-sodium citrate (SSC) concentration in the wash buffer was raised to 5× (750 mM NaCl, 75 mM sodium citrate; pH 7.0).

For colony blot hybridizations, an L. pneumophila 130 genomic library, consisting of 4–6 kb Sau3A1 fragments cloned into pBR322 [Current protocols in molecular biology (Ausubel et al., eds., 1987)], was plated on LB-ampicillin agar for isolation of colonies. The colonies were transferred to nitrocellulose and lysed by incubating the membranes on Whatman paper saturated with 10% SDS, followed by subsequent incubations on denaturing solution (0.5N NaOH, 1.5M NaCl), neutralizing solution (1M Tris-HCl, pH 8.0, 1.5M NaCl), and 2× SSC. All incubations were performed at room temperature for five minutes. Digoxigenin-labeled probes and high-stringency hybridizations were performed as above.

6. Western Blot.

Whole cell lysates were harvested and reacted with antiserum as described previously. Cianciotto, et al., Infect Immun. 58:2912–2918 (1990). Antiserum against E. coli Fur was received from Michael Vasil and used at a 1/100 dilution. Prince, et al., J. Bacteriol. 175:2589–2598 (1993). Horseradish peroxidase-conjugated secondary antibody was used at a 1/1000 dilution (Gibco BRL, Gaithersburg, Md.).

7. Intracellular Infection of U937 Cells.

U937 is a human cell line that differentiates into macrophage-like cells after treatment with phorbol esters. Pearlman, et al., Microb. Pathog. 5:87–95 (1988). U937 cell monolayers were prepared and infected as previously described (Pearlman, et al., Microb. Pathog. 5:87–95 (1988)). After inoculation, the monolayers were incubated for 2 hours to permit bacterial uptake and then washed to remove unattached bacteria. The infected monolayers were incubated at 37° C. in RPMI medium supplemented with 10% fetal bovine serum (Gibco BRL). To assess the relative infectivity of L. pneumophila strains, 50% infective doses ($ID_{50}$) were determined after a 3-day incubation. Cianciotto, et al., Infect. Immun., 57:1255–1262 (1989); O'C.onnell, et al., Infect. Immun., 63:2840–2845 (1995). To quantitate intracellular bacteria, replicate (n=4) monolayers were inoculated with approximately $10^6$ colony forming units (CFU), incubated for 24–72 hours, and then lysed. O'C.onnell, et al., Infect. Immun. 63:2840–2845 (1995). Tenfold serial dilutions of the lysates were plated on BCYE agar, containing chloramphenicol where appropriate, and the resulting CFU were used to calculate the corresponding numbers of bacteria per monolayer.

8. DNA Sequence Analysis.

Cloned L. pneumophila DNA was sequenced from double-stranded plasmids by the dideoxy chain termination method using [$^{35}$S]dATP (Amersham Life Science, Arlington Heights, Ill.) and Sequenase (United States Biochemical, Cleveland, Ohio). Current protocols in molecular biology (Ausubel et al., eds. 1987). Initially, M13-based primers (5'-CCCAGTCACG ACGTTGTAAA ACG [SEQ ID NO: 1] and 5'-AGCGGATAAC AATTTCACAC AG [SEQ ID NO: 2]) and an IS10-based primer (5'-CCTTAACTTA ATGATTTTTA C [SEQ ID NO: 3]) were used to sequence DNAs cloned into pSU2719, which contains lacZ and the multicloning site from pUC19. Andrews, et al., J. Bacteriol. 171:3940–3947 (1989). Twenty custom 18- to 20-mer oligonucleotide primers were used in subsequent reactions. The primers were prepared by the Northwestern University Biotechnology Center using the Applied Biosystems DNA synthesizer (Perkin-Elmer, Foster City, Calif.). Sequencing reactions were performed according to the manufacturer's protocols and the olignonucleotides were electrophoresed in Long-Ranger (AT Biochem, Malvern, Pa.) acrylamide gels. Both strands of DNA were sequenced and then analyzed using PCGene (Intelligenetics, Mountain View, Calif.). Nucleotide and predicted amino acid sequences, as well as initial homology studies, were obtained from GenBank at the National Center for Biotechnology Information (NCBI), National Library of Medicine, NIH. Sequence homologies on the complete predicted amino acid sequences were performed using PCGene. The frgA sequence is deposited in the GenBank database, NCBI, under accession number U76559.

B. Results

1. Identification of Iron-repressed Genes in L. pneumophila.

Figure 2:
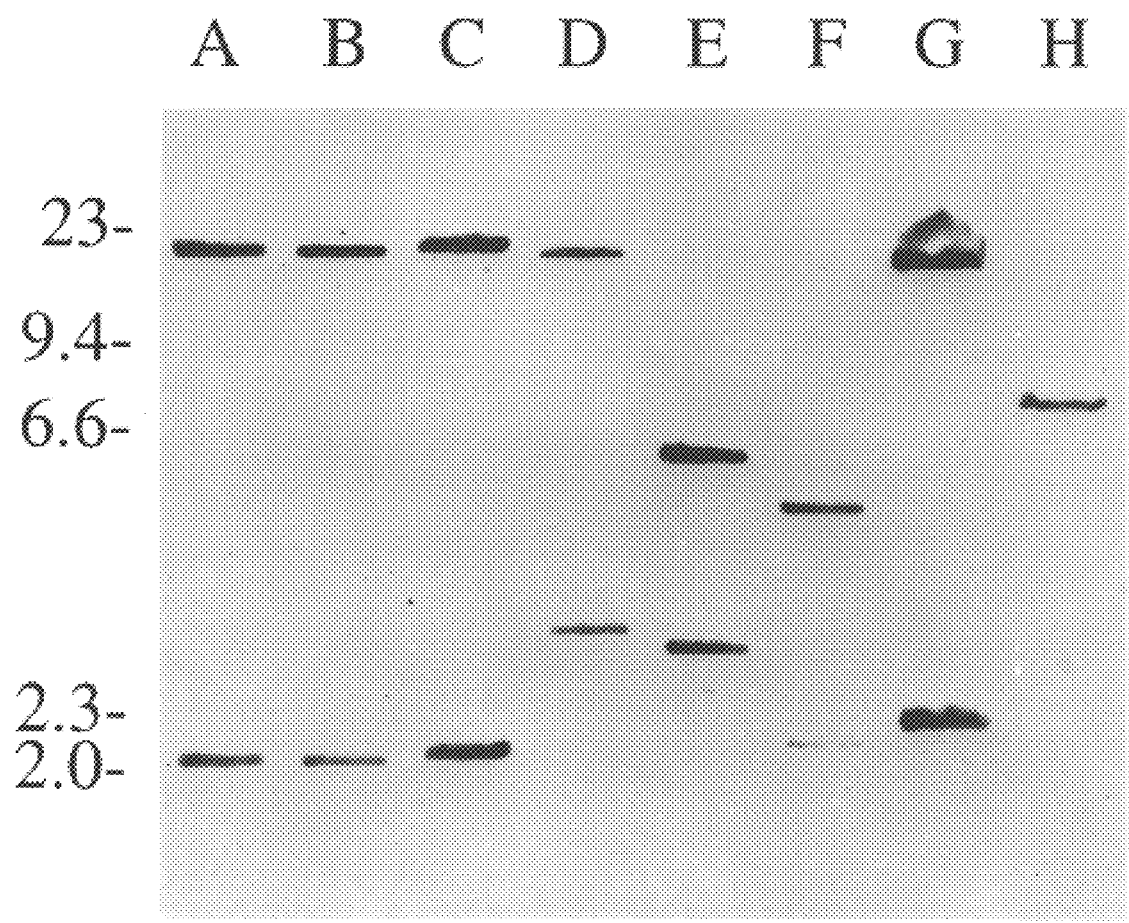

To identify iron-repressed genes of L. pneumophila, strain 130b was mutated with miniTn10'lacZ and screened for strains that had the highest β-galactosidase expression under low-iron growth conditions. Approximately 700 colonies, which appeared white to light blue on standard BYCE agar overlaid with XGAL, were replica plated onto BCYE agar containing 50 μM DFX. The chelator DFX has its greatest affinity (i.e., $10^{31}$) for $Fe^{3+}$, while its next highest affinity (i.e., $10^{14}$) is for $Cu^{2+}$. Keberle, Ann N.Y. Acad. Sci. USA 119:758–768 (1964). Eight mutants, designated as strains NU229 through NU236, consistently expressed higher levels of β-galactosidase activity on the low-iron medium, suggesting that they contained iron-repressed lacZ fusions. Southern blot analyses were performed to determine the number and location of the miniTn10'lacZ insertions in these strains. More specifically, genomic DNAs were digested with HindIII, an enzyme that cuts once within miniTn10'lacZ (FIG. 1), and hybridized with pEH40 (FIG. 2). The banding patterns revealed that each mutant had only one transposon insertion but no additional pEH40 sequences. However, strains NU229, NU230, and NU231 contained identical insertions (see lanes A, B, and C). These results were confirmed by a Southern hybridization using EcoRI digested DNAs (data not shown). Thus, in this initial screening, six unique lacZ fusions were identified that appeared to be iron-regulated. of course, some of these strains may bear mutations in the same gene or operon. Because the goal was to assess the role, if any, for iron-repressed genes in L. pneumophila intracellular infection, rather than an exhaustive search for the total number of iron-regulated genes, these six were the subject of further investigations.

To quantitate the repression of these gene fusions by iron, liquid β-galactosidase assays were performed on NU229, NU232, NU233, NU234 4, NU235, NU236. In two initial trials, all strains, except for NU233, produced less β-galactosidase when grown under high-iron conditions (FIG. 3A, P<0.0001, Student's t-test). NU229 and NU232 showed a 17 fold repression, whereas NU234, NU235, and NU236 exhibited 2–3 fold drops in lacZ expression. Similar levels of repression have been seen in other iron-regulated genes (e.g., E. coli sodA (2–3 fold) and Vibrio anguillarum fatA (14 fold)). Niederhoffer, et al., J. Bacteriol. 172:1930–1938 (1990); Tolmasky, et al., J. Bacteriol. 176:213–220 (1994). In subsequent trials that used increased amounts of DFX, a greater derepression was seen for NU229 and NU232. However, the phenotypes of NU234, NU235, and NU236 were different. In each case, the level of lacZ expression on standard BCYE agar appeared to increase (data not shown). Thus, β-galactosidase production in the presence of EDDA was assessed to confirm the nature of iron-regulation within these strains (FIG. 3B). Like DFX, EDDA is best able to chelate $Fe^{3+}$, having an affinity of $10^{34}$. Freedman, et al., Nature 179:1020–1021 (1957); Miles and Khimji, J. Med. Microbiol. 8:477–492 (1975). In these experiments, the levels of β-galactosidase production in NU234, NU235, and NU236 remained unresponsive to iron. The reason for these changes are not known, but it is assumed that compensatory mutations were sustained and maintained during passage and storage. However, the lacZ fusions in NU229 and NU232 again demonstrated significant derepression when grown on BCYE agar containing an iron chelator. Taken together, these experiments indicate that two mutants, NU229 and NU232, contain stable iron-repressed 'lacZ fusions. The inactivated genes have been designated as frg for iron (fe)-repressed-gene.

2. Fur Repression of the L. pneumophila frq::lacZ Fusions

To begin to understand the mechanism of frg iron regulation, lacZ expression in L. pneumophila strains that differed only in Fur production was assessed. Western blot analysis confirmed the earlier prediction that strain 130b expresses a protein that is cross-reactive with and slightly smaller than E. coli Fur (data not shown). Hickey and Cianciotto, Gene 143:117–121 (1994). Initially, it had been hoped that cloned L. pneumophila fur and allelic exchange could be used to insertionally inactivate the chromosomal fur genes. However, all attempts at this method were unsuccessful in strain 130b (data not shown). The inability to interrupt fur also has been seen in Neisseria gonorrhoeae, Neisseria menigiditis, P. aeruginosa, and V. anguillarum. Berish, et al., Infect. Immun. 61:4599–4606 (1993); Prince, et al., J. Bacteriol. 175:2589–2598 (1993); Thomas and Sparling, Molec. Microbiol. 11:725–737 (1994); Tolmasky, et al. J. Bacteriol. 176:213–220 (1994). As an alternate approach toward isolating Fur mutants, spontaneous manganese-resistant ($Mn^r$) mutants were sought. Since $Mn^{2+}$ and $Fe^{2+}$ can displace each other as co-factors, manganese resistance in E. coli is often achieved through fur mutations that permit increased intracellular iron levels. Hantke, Mol. Gen. Genet. 210:135–139 (1987). The feasibility of this approach was tested in wild-type L. pneumophila. $Mn^r$ legionellae were isolated on BCYE agar containing 0.4–0.6 mM $MnCl_2$ and examined for the loss of Fur by Western blot analysis (Table 1). Whereas strains isolated on 0.4 mM manganese expressed full-sized Fur at normal levels, those obtained on higher concentrations of manganese either expressed a more rapidly migrating protein or an undetectable amount of Fur. The apparently truncated proteins were approximately 5-kDa smaller than Fur and appeared as faint bands on the immunoblot. Introduction of cloned L. pneumophila fur into $Mn^r$ strains restored manganese-sensitivity (data not shown). Therefore, as in P. aeruginosa, V. anguillarum, and V. cholerae, it is possible to isolate L. pneumophila Fur mutants by selecting for $MnCl_2$ resistance. Litwin, et al., J. Bacteriol. 174:1897–1903 (1992); Prince, et al., J. Bacteriol. 175:2589–2598 (1993); Tolmasky, et al., J. Bacteriol. 176:213–220 (1994).

TABLE 1

Manganese resistance and alterations in Fur expression[a]

| [$MnCl_2$] | Frequency of $Mn^r$ CFU | $Mn^r$ strains tested for Fur | # full-length Fur | # truncated Fur | # absent Fur |
|---|---|---|---|---|---|
| 0.1 mM | $8.5 \times 10^{-1}$ | 0 | nd[b] | nd | nd |
| 0.2 mM | $5.0 \times 10^{-4}$ | 0 | nd | nd | nd |
| 0.4 mM | $1.2 \times 10^{-6}$ | 2 | 2 | 0 | 0 |
| 0.5 mM | $3.6 \times 10^{-7}$ | 10 | 3 | 1[c] | 6 |
| 0.6 mM | $3.6 \times 10^{-7}$ | 4 | 1[c] | 2[c] | 1 |

[a]Bacteria were grown on BCYE media for 48 hours and then resuspended in sterile water. Serial dilutions were then plated on BCYE agar containing $MnCl_2$ ranging from 0 to 0.6 mM.
[b]Not determined
[c]Cross-reactive band on the Western blot was barely detectable.

Returning to the original goal of assessing Fur-regulation of frg, $Mn^r$ mutants of NU229 and NU232 were derived on 0.6 mM $MnCl_2$ and then tested for the loss of Fur by Western Blot. Although a Fur null mutant of NU229 was readily obtained, all seven $Mn^r$ derivatives of NU232 tested still produced a full size Fur protein (data not shown). To determine if the frg::lacZ fusion in NU229 is Fur-repressed, quantitative β-galactosidase assays were performed using lysates from $Mn^s$ and $Mn^r$ bacteria grown on standard (high iron) BYCE agar (Table 2). In three trials, the $Mn^r$ derivative displayed elevated enzyme activity (P<0.001, Student's t-test), indicating that the loss of Fur allows for frg::lacz expression in the presence of high iron. The differences in β-galactosidase production within the $Fur^-$ populations likely reflect reversion of the fur mutation since the bacteria used in the assays were necessarily grown in the absence of manganese. In contrast to $Mn^r$ NU229, a representative $Mn^r$ derivative of NU232 did not display derepression of lacZ when it was grown on high iron media (data not shown), a result compatible with the presence of full-length Fur (see above). Strain NU229 became the focus of attention since it possessed a stable iron- and Fur-regulated lacZ fusion, designated frgA.

TABLE 2

NU229 frgA: :lacz expression in the presence or absence of Fur

| | β-galactosidase units[a] | |
|---|---|---|
| Trial[b] | NU229 $Fur^+$ | NU229 $Fur^-$ |
| 1 | 4.2 ± 0.4 | 160.2 ± 20.1 |
| 2 | 2.4 ± 1.5 | 320.5 ± 9.4 |
| 3 | 3.1 ± 0.3 | 583.4 ± 10.0 |

[a]$Fur^+$ ($Mn^s$) NU229 and $Fur^-$ ($Mn^r$) NU229 were grown on standard BCYE agar for 48 hours.
[b]For each trial, each strain was examined in triplicate.

3. Extracellular Growth of NU229.

Because many iron- and Fur-repressed genes are involved in iron-uptake, it was determined if the interruption of frgA affected extracellular growth, particularly under iron-stressed conditions. More specifically, strains 130b and NU229 were compared for their abilities to grow in CDM containing either 0, 4, 8, or 16 μM of added iron (FIG. 4). As expected, no significant growth of 130b was seen in the absence of iron and, as the concentration of iron increased, the duration of the lag phase decreased. Upon entering logarithmic growth, all 130b cultures reached stationary phase within 48–72 hours. Although the final $OD_{660}$ achieved by the NU229 cultures was slightly lower than that reached by 130b, the growth characteristics of the mutant were remarkably similar to wild-type (FIG. 4B–4D). Indeed, the mutant entered logarithmic growth at the same time as the wild-type strain and had comparable growth rates. Similar growth characteristics for 130b and NU229 were also seen when these strains were grown in BYE (data not shown). Therefore, it was concluded that the interruption of frgA had minimal effects on the extracellular growth capacity and extracellular iron acquisition/assimilation functions of *L. pneumophila*. To further demonstrate the latter point, we assessed the mutant's sensitivity to EDDA and its resistance to streptonigrin, an antibiotic that acts with internal iron sources to inhibit bacterial growth. White and Yeowell, *Biochem. Biophys. Res. Commun.* 106:407–411 (1982). Toward this end, 130b, NU229, and strains previously shown to be either streptonigrin-resistant or EDDA-sensitive [Pope, et al., *Infect. Immun.* 64:629–36 (1996)] were plated on BCYE containing either 0.5 $\mu$g/ml of the antibiotic or 50–80 $\mu$M of the chelator. Both 130b and NU229 failed to grow on the streptonigrin medium and grew comparably in the presence of EDDA (data not shown), indicating that there was no change in iron assimilation or storage in the frgA mutant under standard extracellular growth conditions.

4. Intracellular Infection by *L. pneumophila* frg Mutants

Because intracellular growth is the focal point of Legionella pathogenesis, the next step was to determine if NU229 was impaired in infection of macrophages. Initially, $ID_{50}$ analyses were performed using macrophage-like U937 cells. In four separate experiments, strain NU229 displayed a 3.2±1.4 fold increase in $ID_{50}$. More importantly, the monolayers infected with the mutant appeared to contain fewer bacteria than those infected with the wild-type strain. Taken together, these data suggested that frgA has a role in infection in addition to being iron- and Fur-regulated, Incidentally, NU232, NU234, and NU235 showed no change in infectivity during these same $ID_{50}$ experiments, whereas NU236 exhibited an 11.2±3.1 fold increase in $ID_{50}$ (95% confidence limits are defined by $ID_{50}$ ratios of 5.0 and 17.4). To confirm that the infectivity defect seen in NU229 was significant, U937 cell monolayers were infected with comparable numbers of 130b and NU229, and the levels of intracellular bacteria were assessed at 0, 6, 12, 24, 48, and 72 hours post-inoculation (FIG. 5A). At the first three timepoints, there were no differences in recovery between the wild-type and the mutant, indicating that NU229 is not impaired in entry or resistance to immediate intracellular killing. Beginning at 24 hours post-inoculation, however, significantly fewer bacteria were recovered from monolayers infected with NU229. Indeed, there were 9, 80, and 30 fold fewer bacteria at 24, 48, and 72 hours post-inoculation, respectively. Similar results were obtained in two subsequent experiments that assayed the number of bacteria per monolayer at 72 hours post-inoculation (data not shown). Therefore, NU229 has a significant and reproducible defect in intracellular growth.

It was next investigated whether the reduced infectivity of NU229 was due to the inactivation of frgA rather than a spontaneous second-site mutation. Thus, the mutant was remade by allelic exchange. More specifically, an approximately 12-kb PstI fragment containing frgA::lacZ (and $Km^r$) was isolated from NU229 and cloned into the PstI site in sacB-containing pEA75. Following electroporation of the recombinant plasmid into strain 130b, six $Km^r$, sucrose-resistant colonies were obtained. All of these clones, when tested by Southern hybridization, contained the same DNA insertion as NU229 (data not shown). In addition, all of the clones produced higher levels of β-galactosidase when grown under low-iron conditions, as did NU229. One strain, designated as NU229R, was further tested in U937 cells. NU229R demonstrated no infectivity difference from the original NU229 on three separate occasions, one of which is represented in FIG. 5A. The similarities between NU229 and NU229R indicate that the frgA interruption, not a second-site mutation, caused the defect in intracellular growth.

5. Sequence Analysis of *L. pneumophila* frgA.

As the first step towards understanding the behavior of NU229, the nucleotide sequence of frgA was determined. Toward that end, the 12-kb PstI fragment containing frgA::lacZ was cloned into pSU2719 to yield pEH44 (FIG. 6). To initiate sequence analysis using IS10 primers, the subclones pEH45 and pEH46 (FIG. 6) were utilized. Subsequent sequencing reactions were performed with the pEH44 template DNA and a series of custom primers. To confirm the nucleotide sequence at the point of transposon insertion, a plasmid (pEH65) containing the uninterrupted 3' end of frgA was isolated from a genomic library using probe A (see FIG. 6) and then analyzed. FIG. 7 contains the sequence of the frgA open reading frame (ORF), as well as flanking regions [SEQ ID NO: 4], and the predicted amino acid sequence [SEQ ID NO;5]. The frgA ORF begins at an ATG start codon and ends 1725 bp downstream at a TAA stop codon. This ORF would encode a protein of 575 amino acids and 63.3 kDa. The *L. pneumophila* frgA ORF was preceded by a ribosome binding site within 10 bp of the start codon, as well as a -10 and a -35 region that closely matched the *E. coli* consensus. Rosenberg and Court, *Annu. Rev. Genet.* 13:319–353 (1979). Most promoter regions of genes regulated by Fur contain at least one ironbox [Calderwood and Mekalanos, *J. Bacteriol.* 169:4759–4764 (1987); de Lorenzo, et al., *J. Bacteriol.* 169:2624–2630 (1987)], generally occurring within the -35 region to the -10 region, that represents the binding site(s) for $Fur\text{-}Fe^{2+}$ repressors [Litwin, et al., *J. Bacteriol.* 174:1897–1903 (1992)]. The *L. pneumophila* frgA promoter region contained two overlapping ironboxes that had 4–5 mismatches, as compared to the *E. coli* consensus sequence, 5'-GATAATGATA ATCATTATC [SEQ ID NO:47] (FIG. 7). Calderwood, et al., *J. Bacteriol.* 169:4759–4764 (1987); de Lorenzo, et al., *J. Bacteriol.* 169:2624–2630 (1987). This finding supports our earlier conclusion that frgA is iron- and Fur-regulated.

Database searches using the predicted amino acid sequence of frgA showed that it shares homology with two proteins, IucA and IucC, encoded by the first and third genes in the Fur-repressed *E. coli* aerobactin operon (FIG. 8; SEQ ID NOS: 6–44). Martinez, et al., *J. Mol. Biol.* 238:288–293 (1994). In the third step of the siderophore's biosynthesis, IucA catalyzes the addition of $N^{\epsilon}$-acetyl-$N^{\epsilon}$-hydroxylysine to citric acid to yield the intermediate $N^{\alpha}$-citryl-$N^{\epsilon}$-acetyl-$N^{\epsilon}$-hydroxylysine. Subsequently, IucC adds another $N^{\epsilon}$-acetyl-$N^{\epsilon}$-hydroxylysine moiety to the intermediate to form aerobactin. de Lorenzo and Neilands, *J. Bacteriol.* 167:350–5 (1986). In a previous report by de Lorenzo, et al. [Martinez, et al., *J. Mol. Biol.* 238:288–293 (1994)], a 21% identity and 47% similarity between IucA and IucC was recognized as significant. While IucA and IucC catalyze similar reactions and have structural homology, they are not interchangeable (de Lorenzo and Neilands, *J. Bacteriol.* 167:350–5 (1986)). The overall identity and similarity between *L. pneumophila* FrgA and *E. coli* IucA were 15.7% and 26.1% respectively. Furthermore, FrgA had an 18.3% identify and a 32.6% similarity to IucC. BLASTX results from the NCBI specified the three regions of greatest homology between FrgA and the *E. coli* proteins. The three boxes in FIG. 8 denote these regions for IucA, and the BLASTX identity:similarity results were 23%:51%, 29%:45%, and 31%:46%, respectively. The three shaded areas denote these regions for IucC with BLASTX identify:similarity results of 21%:47%, 45%:75%, 32%:51% respectively. It is also worth noting that FrgA is comparable in size to both IucC and IucA; indeed, it is predicted to have the same number of amino acids as IucA (FIG. 8). Taken together, these data suggest that frgA encodes an IucA- or IucC-like protein. Sequences upstream and downstream of frgA, however, did not reveal any ORFs that could be a part of an iuc-like operon (FIG. 7 and data not shown).

6. Complementation of the frgA Mutation.

To determine if the infectivity defect in NU229 is due to the loss of FrgA or due to a polar effect (i.e., a block in transcription of a gene downstream of frgA), efforts were made to restore full infectivity to the mutant by introducing into it an intact plasmid-encoded frgA. First, using a frgA specific probe (see probe B in FIG. 6), the complete gene was isolated on plasmid pEH74 from our genomic library. Next, frgA was subcloned on a 2886 bp KpnI-XhoI fragment into the vector pSU2719 to yield pEH75. Although pEH75 contains 1093 bp upstream of the frgA start codon, it does not contain any ORFs that would be transcribed in the same direction as frgA. More importantly, pEH75 does not contain any downstream ORFs since the XhoI site is only 62 bp downstream from the frgA stop codon (FIG. 7). Finally, pEH75 was electroporated into NU229, and transformants were obtained on BCYE containing kanamycin and chloramphenicol. To have controls for the infectivity studies, NU229 and 130b containing the Cm$^r$ pSU2719 vector were isolated. In three separate experiments, one of which is depicted in FIG. 5B, strain NU229 (pEH75) exhibited intracellular growth characteristics that were comparable to 130b. This result demonstrates that the presence of frgA alone was sufficient to restore infectivity to NU229, and that this gene is required for optimal intracellular infection.

7. Distribution of frgA Among *L. pneumophila* Strains and Legionella Species

To determine if frgA is conserved among different *L. pneumophila* strains and Legionella species, southern hybridization analyses were performed using probe B (FIG. 6). The frgA specific probe hybridized under high stringency conditions to DNAs from the eleven strains of *L. pneumophila* that were tested (i.e., representatives of serogroups 1–4 and 6–14) (FIG. 9). However, the probe did not hybridize, even under low stringency conditions, with DNAs from *L. birminghamensis, L. dumoffii, L. erytha, L. gormanii, L. feeleii, L. hackeliae, L. israelensis, L. jamestowniensis, L. longbeachae, L. micdadei, L. oakridgensis, L. parisiensis, L. sainthelensi, L. santicrusis, L. spiritensis*, and *L. tucsoniensis* (FIG. 9). The strains tested represent both clinical and environmental isolates. These results indicate that frgA is conserved within, and is specific to, strains of *L. pneumophila*.

C. Discussion

The identification of genes whose expression is repressed by Fur in response to iron availability may lead to the isolation of virulence determinants for two central reasons. First, genes encoding iron-acquisition systems can themselves be essential for bacterial survival within mammalian hosts. Examples of these are the ferrous iron uptake systems and the aerobactin operon of pathogenic *E. coli*. Kammler, et al., *J. Bacteriol*. 175:6212–6219 (1993); Payne, *Trends Microbiol*. 1:66–69 (1993); Valvano and Crosa, *Infect Immun*. 46:159–167 (1984). Second, factors not directly involved in iron assimilation can be repressed by Fur. Several examples of these are the Shiga-like toxin and superoxide dismutase from *E. coli*, a hemolysin and the outer membrane IrgA protein from *V. cholerae*, and exotoxin A from *P. aeruginosa*. Calderwood and Mekalanos, *J. Bacteriol*. 169:4759–4764 (1987); Goldberg, et al., *Proc. Natl. Acad. Sci USA* 88:1125–1129 (1991); Litwin, et al., *J. Bacteriol*. 174:1897–1903 (1992); Niederhoffer, et al., *J. Bacteriol*. 172:1930–1938 (1990); Prince, et al., *J. Bacteriol*. 175:2589–2598 (1993). The majority of information on iron- and Fur-repressed genes comes from studies on either extracellular pathogens or facultative intracellular parasites of the gastrointestinal tract. Litwin and Calderwood, *Clin. Microbiol. Rev*. 6:137–149 (1993).

The data indicated that *L. pneumophila* Fur is structurally and antigenically similar to *E. coli* Fur, but the Legionella fur gene, unlike Escherichia fur, appears to be essential for bacterial viability, as seen by the inability to insertionally inactivate it. A complete loss of Fur in *L. pneumophila*, as well as in *N. meningiditis, N. gonorrhoeae, P. aeruginosa*, and *V. anguillarum*, probably increases the levels of iron to a point that is bactericidal under aerobic growth conditions. Berish, et al., *Infect. Immun*. 61:4599–4606 (1993); Prince, et al., *J. Bacteriol*. 175:2589–2598 (1993); Thomas and Sparling, *Molec. Microbiol*. 11:725–737 (1994); Tolmasky, et al., *J. Bacteriol*. 176:213–220 (1994); Touati, et al., *J. Bacteriol*. 177:2305–2314 (1995). To study Fur-regulated genes, spontaneous $Mn^r$ mutants were used. $Mn^r$ strains of *V. anguillarum* and *V. cholerae* have been shown to bear point mutations in fur, generally causing changes in the amino-terminal half of Fur. Lam, et al., *J. Bacteriol*. 176:5108–5115 (1994); Wertheimer, et al., *J. Bacteriol* 176:5116–5122 (1994). Since minimal levels of Fur activity are likely present in our $Mn^r$ mutants, it may not be able to identify genes whose expression is regulated only slightly by Fur. Nevertheless, the ability to generate fur mutants and effectively introduce 'lacZ into virulent legionellae allowed study of the iron regulation of five *L. pneumophila* (frg) loci.

Stable iron regulation was noted in two of the five strains, NU232 and NU229. The frg (frgB) in strain NU232 was repressed 17 fold in response to iron. However, its Fur regulation could not be assessed because an NU232 $Fur^{-1}$ derivative could not be obtained. An initial attempt at demonstrating Fur repression of frgB in *E. coli* also proved inconclusive, i.e., when cloned along with 3 kb of upstream DNA, frgB-lacZ was expressed to a similar degree in $Fur^+$ and $Fur^-$ strains (data not shown). The basis for the lethality of the fur-frgB double mutation is unclear, but it likely involves toxic levels of intracellular iron associated with the fur mutation. This result may provide a clue to frgB function. For example, the inability of the frgB mutation to offset Fur derepression suggests that it is not involved in iron-uptake. Instead, it may encode an iron-storage protein, such as bacterioferritin or the ferritin H-like protein, whose absence would facilitate iron overload. Andrews, et al., *J. Bacteriol*. 171:3940–3947 (1989); Izuhara, et al., *Mol. Gen. Genet*. 225:510–513 (1991). Alternately, it may express a protein, such as a DNA repair enzyme, superoxide dismutase, or peroxidase, involved in the protection of DNA damage from iron-catalyzed oxygen radicals. Touati, et al., *J. Bacteriol*. 177:2305–2314 (1995). The frgA gene in strain NU229 had a similar level of iron-regulation as frgB, but was repressed by Fur. Since a fur mutation in NU229 could be isolated, frgA is more likely to be involved in iron uptake than the frgB. The level of derepression associated with the loss of Fur was greater than that achieved by growth under low-iron conditions. A likely explanation for this result is that some Fur dimers were still bound to promoter regions at the levels of iron chelator that were tested. Assessment of lacZ expression under conditions of greater iron limitation was attempted. However, an increased concentration of the chelator caused an inhibition of growth by both wild-type and mutant strains, prohibiting any further examination of specific gene expression. Regardless, the characterization of NU229 demonstrates that iron regulation in *L. pneumophila* is explained, at least in part, by Fur-mediated repression.

Although essentially unaltered in its extracellular growth capability, NU229 was significantly impaired in intracellular growth. Despite an apparently normal capacity to enter into host cells and to resist macrophage bacteriocidal elements, the mutant replicated in a manner that yielded significantly fewer progeny than wild-type in a 72 hour time period. A comparison of macrophage growth kinetics suggests that NU229 is distinct from all other *L. pneumophila* mutants (i.e., mip, icm, dot, and ira mutants) found to be impaired for intracellular replication. Berger, et al., *Molec. Microbiol.* 14:809–22 (1994); Brand, et al., *Molec. Microbiol.* 14:797–808 (1994); Cianciotto, et al., *Infect Immun.* 57:1255–1262 (1989); Pope, et al., *Infect. Immun.* 64:629–36 (1996). Complementation analysis further demonstrated that the infectivity defect of NU229 was due directly to the inactivation of frgA. Thus, frgA can be added to the small but growing list of *L. pneumophila* infectivity genes. Furthermore, the demonstration that an iron- and Fur-regulated gene can promote intracellular growth supports the notion that the phagosomal compartment is a low-iron environment. Pope, et al., *Infect. Immun.* 64:629–36 (1996); Portillo, et al., *Mol. Microbiol.* 6:3289–3297 (1992).

The *L. pneumophila* FrgA protein was similar to IucA and IucC in the aerobactin iron-uptake system of *E. coli*. A comparison of IucA and IucC sequences disclosed three hydrophilic domains of greater than 57% similarity which are thought to contain the active centers of these enzymes. Martinez, et al., *J. Mol. Biol.* 238:288–293 (1994). Interestingly, the regions of highest homology between FrgA and the Iuc proteins overlap these sequences. Thus, the 21–45% amino acid identities that exist between FrgA and IucA/C may reflect a common function. In a potentially analogous situation, the carboxyl-terminals of *L. pneumophila* Mip and the FK506-binding protein of *Neurospora crassa* share 39% of their sequence and still possess similar peptidyl-prolyl cis/trans isomerase activity. Fischer, et al., *Molec. Microbiol.* 6:1375–1383 (1992); Tropschug, et al., *Nature* 346:674–677 (1990). The discovery that frgA has homology with genes intimately involved in siderophore biosynthesis was exciting but also quite unexpected for several reasons. First, the absence of a aerobactin-like siderophore in *L. pneumophila* strains was demonstrated by the Csaky assay, which identifies hydroxymate siderophores due to their chemical structure. Reeves, et al., *J. Bacteriol.* 154:324–329 (1983). Second, the Chrom-Azurol S (CAS) assay, a procedure which measures chelating activity independent of structure, failed to detect siderophores in culture supernatants of strain 130b. Goldoni, et al., *J. Med. Microbiol.* 34:113–8 (1991); Liles and Cianciotto, *Infect Immun.* 64:1873–1875 (1996). Third, in a classic bioassay, concentrated supernatants from one iron-depleted *L. pneumophila* culture did not stimulate the growth of a second iron-starved culture. Reeves, et al., *J. Bacteriol.* 154:324–329 (1983). Finally, NU229 was not sensitive to iron limitation and was not resistant to streptonigrin when grown on bacteriological media. On the other hand, the importance of frgA for growth within the iron-limiting environment of a macrophage and its iron-dependent regulation by Fur suggests a role in iron-acquisition. These data can be rationalized in one of two ways. Either FrgA catalyzes a reaction akin to the ones mediated by IucA and IucC, but does not result in the production of a "classic" siderophore or, along with unlinked loci, frgA is involved in the production of an iron chelator prevalent in the intracellular environment. The absence of $Fe^{3+}$-chelating activity in *L. pneumophila* supernatants, despite frgA expression in low-iron bacteriological media, would suggest that the production of this putative siderophore is not solely responsive to iron and Fur fluctuations. Clearly, the role of frgA in iron acquisition is yet to be elucidated; however, its sequence has caused us to once again reexamine our view of *L. pneumophila* and siderophores.

The frgA gene was interesting not only for its role in macrophage infection and its sequence homologies, but also for its unique distribution among legionellae. Southern hybridization analysis indicated that frgA sequences are limited to the *L. pneumophila* species. Nearly all previously identified *L. pneumophila* genes, including flaA, fur, htp, lly, mip, ompS, and pplA (pal), have had homologs in all or virtually all other Legionella species. Bender, et al., *Infect. Immun.* 59:3333–6 (1991); Cianciotto, et al., *Infect Immun.* 58:2912–2918 (1990); Heuner, et al., *Infect. Immun.* 63:2499–507 (1995); Hickey and Cianciotto, *Gene* 143:117–121 (1994); Hoffman, et al., *Infect. Immun.* 57:1731–1739 (1989); Hoffman, et al., *J. Bacteriol.* 174:914–920 (1992); Ott, et al., *Microb. Pathog.* 11:357–65 (1991). The other exceptional gene beside frgA is hbp, whose isolation and identification is described in Example 2. See also O'C.onnell, et al., *Infect. Immun.* 64:842–848 (1996). The absence of frgA among the sixteen Legionella species examined signals that the gene can be used as a diagnostic reagent. The mip primers used for the PCR detection of *L. pneumophila* within water and clinical samples have, on several instances, amplified DNAs from other Legionella species. Atlas, et al., *App. Environ Microbiol.* 61:1208–1213 (1995); Cianciotto and Fields, *Proc. Natl. Acad. Sci. USA* 89:5188–5191 (1992); Jaulhac, et al., *J. Clin Microbiol* 30:920–924 (1992); Kessler, et al., *J. Clin. Microbiol.* 31:3325–3328 (1993); Lindsay, et al., *J. Clin. Microbiol.* 32:3068–3069 (1994). Thus, frgA primers, even more so than hbp primers, should enhance the specificity of *L. pneumophila* detection protocols (see Example 2).

Example 2

Cloning and Mutation of *L. pneumophila* hbp Genes

A. Materials and Methods

1. BACTERIAL STRAINS AND MEDIA. Virulent *L. pneumophila* serogroup 1 strains Wadsworth 130b and Philadelphia 1, serogroup 8 strain Concord 3, and serogroup 13 strain B2A3105 were previously described. Cianciotto, et al., *Mol. Biol. Med.* 6:490 (1981). Strains of *Legionella erthyra, L. feeleii, L. hackeliae, L. longbeachae, L. micdadei, L. moravica, L. sainticrucis*, and *L. spiritensis* were also included in this study. Cianciotto, et al., *Mol. Biol. Med.* 6:490 (1981). Like *L. pneumophila*, the species *L. feeleii, L. hackeliae, L. longbeachae*, and *L. micdadei* have been associated with human disease. Generally, the legionellae were grown on standard BCYE agar plates for 48 h at 37° C., and, when appropriate, 3 μg of chloramphenicol per ml, 25 μg of kanamycin per ml, or 5% (wt/vol) sucrose was added to the medium. For experiments that assessed hemin utilization and binding, a slightly modified form of yeast extract phosphate (YP) medium was employed as the base medium. Armon, and Payment, *J. Microbiol. Methods* 11:65–71 (1990); Johnson, et al., *J. Clin. Microbiol.* 15:342–344 (1982). This medium contained, as a supplement, 250 mg of ferric pyrophosphate ($PP_i$) and 400 mg of cysteine per liter. The chemically defined medium (CDM) described by Reeves et al. was employed to further assess the ability of Legionella species to use hemin as an iron source. Reeves, et al., *J. Clin. Microbiol.* 13:688–695 (1981). BYE broth cultures were washed in CDM and then inoculated into acid-washed, 125-ml flasks containing 25 ml of CDM. The resultant cell suspensions were incubated at 37° C. with agitation.

E. coli HB101 served as the host for recombinant plasmids. *Current protocols in molecular biology* (Ausubel, et al., eds., 1987). It was maintained on Luria-Bertani agar medium containing either 30 μg of chloramphenicol, 50 μg of kanamycin, or 50 μg of ampicillin per ml. *Current protocols in molecular biology* (Ausubel, et al., eds., 1987). Recombinant E. coli cells were also grown on M9CA-salts agar supplemented with either 100 μg of hemin or Congo red per ml. Hanson and Hansen, *Mol. Microbiol.* 5:267–278 (1991).

Unless otherwise noted, chemicals were obtained from Sigma Chemical Co., St. Louis, Mo.

2. Plasmids and a Genomic Library. Plasmids pBR322 and pUC18 were used as cloning vehicles. *Current protocols in molecular biology* (Ausubel, et al., eds., 1987). Another ColE1 replicon, pBOC20, was used in the allelic exchange protocol. This plasmid represents the multicloning site from PHXK cloned into pEA75. O'C.onnell et al., *Infect. Immun.* 63:2840–2845 (1995). Importantly, it contains a selectable chloramphenicol resistance (Cm$^r$) marker and the counterselectable sacB. The vector pNK2794 served as the source for a 1.7-kb BamHI fragment which contains a kanamycin resistance (Km$^r$) gene. O'C.onnell et al., *Infect. Immun.* 63:2840–2845 (1995). Finally, the mip-containing plasmid pSMJ31.42 was used as a probe in Southern hybridizations. Engleberg, et al., *Infect. Immun.* 57:1263–1270 (1989). Plasmids were isolated from E. coli by the alkaline lysis procedure. *Current protocols in molecular biology* (Ausubel, et al., eds., 1987). The genomic library used in this study was derived from L. pneumophila 130b and consisted of 3–6 kb Sau3A fragments cloned into pBR322. Hickey and Cianciotto, *Gene* 143:117–121 (1994).

3. Electroporation and Allelic-exchange Mutagenesis. Plasmids were introduced into L. pneumophila by electroporation. Cianciotto and Fields, *Proc. Natl. Acad. Sci USA* 89:5188–5191 (1992). The procedure for allelic exchange with ColE1 vectors containing counterselectable markers has been previously described. Cianciotto, et al., *FEMS Microbiol. Lett.* 56:203–208 (1988); O'C.onnell, et al., *Infect. Immun.* 63:2840–2845 (1995). Using this protocol, we achieved insertional inactivation of hbp within a strain that had been passaged six times on BCYE agar plates.

4. Northern (RNA) and Southern Hybridizations. Whole-cell RNAs and DNAs were extracted from Legionella strains as described previously. Cianciotto, et al., *FEMS Microbiol. Lett.* 56:203–208 (1988); Engleberg, et al., *Infect. Immun.* 57:1263–1270 (1989). Northern hybridizations were performed by standard protocols. *Current protocols in molecular biology* (Ausubel, et al., eds., 1987). RNAs were electrophoresed through a gel that contained 1% agarose and 2.2M formaldehyde and that was bathed in 1× morpholinepropanesulfonic acid (MOPS) buffer. The sizes of the molecular weight standards that were used to estimate the lengths of mRNA species were 9.5, 7.5, 4.4, 2.4, 1.4, and 0.24 kb (Gibco-BRL, Gaithersburg, Md.). Southern hybridizations were performed under high- and low-stringency conditions which permit approximately 10 and 30% bp mismatching, respectively. *Current protocols in molecular biology* (Ausubel, et al., eds., 1987); Cianciotto, et al., *Infect. Immun.* 58:2912–2918 (1990). Probes consisted of both plasmids and gel-isolated restriction fragments which were radiolabeled with $^{32}$P by using a random primer labeling kit (Gibco-BRL).

5. DNA Sequence Analysis. Cloned L. pneumophila DNA was sequenced from double-stranded plasmids by the dideoxy chain-termination method with $^{35}$S-dATP and Sequenase (Amersham, Arlington Heights, Ill.). *Current protocols in molecular biology* (Ausubel, et al., eds., 1987). Initially, M13-based primers were used to sequence DNAs cloned into pUC18; however, custom 20-bp oligodeoxyribonucleotide primers were used in subsequent reactions. The unique primers were prepared by the Northwestern University Biotechnology Center with an Applied Biosystems DNA synthesizer. Sequencing reactions were performed according to the manufacturer's protocols. Nucleotide sequences were analyzed with PCGENE (IntelliGenetics), and homology searches were conducted through GenBank at the NCBI.

6. Liquid Hemin-binding Assay. To quantitate the ability of L. pneumophila and E. coli strains to bind hemin, the standard liquid hemin-binding assay was employed. Daskaleros and Payne, *Infect. Immun.* 55:1393–1398 (1987); Deneer and Potter, *Infect. Immun.* 57:798–804 (1989); Genco, et al., *Infect. Immun.* 62:2885–2892 (1994); Hanson and Hansen, *Mol. Microbiol.* 5:267–278 (1991); Kay, et al., *J. Bacteriol.* 164:1332–1336 (1985). Prior to exposure to hemin, the legionellae were grown for 48 h on agar media and then subjected to a series of washes. First, the bacteria were harvested from plates into 40 ml of distilled water, achieving an optical density at 660 nm ($OD_{660}$) of approximately 1.5. Then, after centrifugation of the cell suspension for 10 min at 4,500×g, the pellet was dissolved in 15 ml of 0.1M Tris (pH 8.0). Subsequent to a second centrifugation step, the bacteria were resuspended for the last time in 15 ml of BYE broth. After removal of 0.1 ml from the final cell suspension for a CFU determination, 1-ml aliquots were placed into 1.5-ml Microfuge tubes and brought to concentrations of either 5, 10, 15, or 20 μg of hemin per ml by additions from a freshly prepared 1-mg/ml stock in BYE. The bacterium-hemin mixture was then rotated at 37° C. After a 1-h incubation, the cell suspension was centrifuged for 2 min at 8,000×g. Finally, 0.75 ml of the supernatant was examined, along with the appropriate hemin-BYE control, for its $A_{400}$. As always, the extent of hemin binding was a reflection of the reduction in the $OD_{400}$. E. coli strains were grown and assayed in M9CA salts broth.

7. Intracellular Infection of U937 Cells and Amoebae by L. pneumophila. U937 cell monolayers were prepared and infected with L. pneumophila as previously described. Cianciotto, et al., *Infect. Immun.* 57:1255–1262 (1989); O'C.onnell, et al., *Infect. Immun.* 63:2840–2845 (1995); Pearlman, et al., *Microb. Pathog.* 5:87–95 (1988). Following inoculation, the monolayers were incubated for 2 h to permit bacterial uptake and were then vigorously washed to remove unattached bacteria. The infected monolayers were incubated at 37° C. in RPMI medium supplemented with 10% fetal bovine serum. To assess the relative infectivity of strains for U937 cells, 50% infective doses were determined after 72 h of incubation. Cianciotto, et al., *Infect. Immun.* 57:1255–1262 (1989). To monitor intracellular growth rates, replicate monolayers were inoculated with approximately $10^6$ bacteria, incubated for various times, and then lysed. Cianciotto, et al., *Infect. Immun.* 57:1255–1262 (1989); O'C.onnell, et al., *Infect. Immun.* 63:2840–2845 (1995). Tenfold serial dilutions of the lysates were plated on BCYE agar, and the resulting CFU were used to calculate the corresponding numbers of bacteria per monolayer. In some experiments, the U937 cells were treated before and after infection with 7 μM DFX. DFX inhibits Legionella replication within macrophages by reducing intracellular iron availability. Byrd and Horwitz, *J. Clin. Invest.* 83:1457–1465 (1989); Gebran, et al., *Infect. Immun.* 62:564–568 (1994); Pope, et al., *Infect. Immun.* 64:629–636 (1996).

Intracellular infection of the freshwater amoeba *Hartmannella vermiformis* was performed as previously described. Cianciotto and Fields, *Proc. Natl. Acad. Sci USA* 89:5188–5191 (1992); King, et al., *Infect. Immun.*

59:758–763 (1991). Briefly, replicate Hartmannella cultures containing $10^5$ amoebae were infected with $10^3$ CFU, and after various incubation periods, the numbers of legionellae within the cocultures were determined by plating aliquots on BCYE medium.

8. Nucleotide Sequence Accession Number. The hbp sequence has been deposited in the GenBank database at the NCBI under accession number U4338.

B. Results

1. Hemin Utilization and Binding by *L. pneumophila*. Since the ability of hemin to enhance Legionella growth is most manifest on YP agar plates [Johnson, et al., J. Clin. Microbiol. 15:342–344 (1992)], the behavior of wild-type strain 130b on this medium was examined. Initially, two key observations of the previous study were confirmed. First, the number of CFU recoverable on YP agar was 3% of that recoverable on BCYE (Table 3 below). Second, the addition of hemin to the medium increased the CFU by nearly 10-fold (Table 3). However, to highlight more clearly the role of hemin in Legionella physiology, the growth of strain 130b on YP media that were lacking $Fe^{3+}$ supplements and that were thus nonpermissive (Table 3) was examined. In six separate experiments (two of which appear in Table 3), the addition of 30 μM hemin completely restored the ability of strain 130b to form colonies on low-iron YP medium. Importantly, an equimolar amount of protoporphyrin IX could not substitute for hemin. Taken together, these data suggest that hemin can be an iron source for *L. pneumophila*. To support this idea, the ability of hemin to replace ferric iron in a CDM was examined. The omission of ferric salts from the CDM prevented the growth of strain 130b, confirming that iron is essential for *L. pneumophila* replication. The addition of 6.25, 12.5, or 25 μM $Fe^{3+}$ to the medium fully restored bacterial growth (data not shown). More importantly, growth of 130b was supported by $Fe^{3+}$-free CDM that had been supplemented with hemin. Whereas the addition of 6.25 μM hemin yielded 75 to 90% maximal growth, the addition of 12.5 or 20 μM hemin promoted full replication (data not shown). Since 6.25 μM $Fe^{3+}$ supported better growth than did an equimolar amount of heme-iron, it is suspected that ferric iron is the more effective iron source for the legionellae. Nevertheless, the data demonstrated that hemin can be the sole iron source for *L. pneumophila*.

TABLE 3

Plating efficiency of *L. pneumophila* 130b on YP media

| Agar medium[a] | Average no. of CFU/ml recovered[b] | |
|---|---|---|
| | Expt 1 | Expt 2 |
| BCYE | $1.7 \times 10^8$ | $1.6 \times 10^8$ |
| YP | $5.5 \times 10^6$ | ND |
| YP + Hemin | $4.7 \times 10^7$ | ND |
| YP − Fe | $<10^{2c}$ | $<10^{1c}$ |
| YP − Fe + hemin | $3.9 \times 10^7$ | $2.1 \times 10^7$ |
| YP − Fe + PP | ND | $<10^{1c}$ |

[a]YP + hemin, YP supplemented with 30 μM hemin; YP − Fe, YP lacking its ferric $PP_i$ supplement; YP − Fe + hemin, YP lacking ferric $PP_i$ but supplemented with 30 μM hemin; YP − Fe + PP, YP lacking ferric $PP_i$ but supplemented with 30 μM protoporphyrin IX.
[b]Bacteria were grown on BCYE agar plates for 48 h, resuspended in distilled $H_2O$ to an $OD_{660}$ of approximately 0.3, and then plated in triplicate for determinations of the numbers of CFU on the indicated media. ND, not determined.
[c]No CFU recovered.

To substantiate the idea that *L. pneumophila* can directly utilize heme compounds, we assayed strain 130b for its ability to bind hemin. Following growth on YP-minus-Fe-plus-hemin (Table 3) media, *L. pneumophila* consistently bound 50 to 60% of the added hemin (see FIG. 10). This level of hemin binding was 10-fold greater than that of *E. coli* HB101 (see below). Legionellae harvested from BCYE agar plates also bound appreciable amounts of hemin, indicating that *L. pneumophila* hemin binding was not a peculiarity of growth on YP media (FIG. 10). Interestingly, however, these bacteria adsorbed noticeably less of the compound than did those obtained from the hemin-containing YP agar. Taken together, these initial experiments predicted that *L. pneumophila* had surface structures (proteins) which promote hemin acquisition.

2. Identification of a *L. pneumophila* Gene That Promotes Hemin Binding. To identify *L. pneumophila* proteins involved in hemin acquisition, a genomic library was screened for a locus that could confer upon *E. coli* HB101 the ability to bind hemin. Using an approach which recently led to the characterization of a hemin-binding membrane protein of *H. influenzae* [Hanson and Hansen, Mol. Microbiol. 5:267–278 (1991)], recombinant bacteria that appeared brown on M9CA salts agar plates containing 0.01% hemin were sought. Since bacteria and proteins that specifically interact with hemin often bind Congo red [Daskaleros and Payne, Infect. Immun. 55:1393–1398 (1987); Deneer and Potter, Infect. Immun. 57:798–804 (1989); Genco, et al., Infect. Immun. 62:2885–2892 (1994); Kay, et al., J. Bacteriol. 164:1332–1336 (1985); Stugard, et al., Infect. Immun. 57:3534–3539 (1989)], screening was for clones that were also colored on media containing that dye. Three pigmented recombinant strains were obtained. Importantly, the plasmids pEH1, pEH2, and pBOC3, which were isolated from these clones, conferred pigmentation upon retransformation into HB101. To confirm that HB101(pEH1), HB101(pEH2), and HB101(pBOC3) had enhanced hemin-binding activity, their abilities to remove hemin from solution were assessed. Indeed, all three clones bound about 60% more hemin than did HB101 (pBR322) (see FIG. 11A). Restriction enzyme digestion analyses and Southern hybridizations indicated that pEH1, pEH2, and pBOC3 were overlapping and contained *L. pneumophila* 130b DNA (see FIG. 12).

Subcloning mapped the locus responsible for hemin binding to a 1.1-kb SacI-AflII fragment (FIG. 12). DNA sequence analysis indicated that this region of the *L. pneumophila* chromosome contained one intact open reading frame (ORF). A $Km^r$ insertion into the HincII site of pEH12 abolished pigmentation in recombinant *E. coli*, confirming that this ORF is required for hemin binding (FIG. 12). The ORF is designated as hbp for hemin binding promotion. (Note that in a preliminary report the ORF had been referred to as heb for hemin binding. O'C.onnell and Cianciotto, Abstr. B-7, p. 29, in Abstracts of the 94th General Meeting of the American Society for Microbiology 1994 (American Society for Microbiology, Washington, D.C. 1994). The hbp ORF was predicted to encode a protein (Hbp) of 141 amino acids and 15.5 kDa. Interestingly, Hbp contained a 22-residue signal sequence (see Chart A below), indicating that it may be secreted in *E. coli* and *L. pneumophila*. Database searches failed to reveal significant degrees of homology between Hbp and known proteins.

The hbp ORF was preceded by a ribosome-binding site within 13 bp of the initiation codon (Chart A). Further upstream, there existed two potential -10 regions. The first of these putative promoter regions contained several sets of sequences that had homology with Fur binding sites. Hickey and Cianciotto, Gene 143:117–121 (1994). The presence of ironboxes suggested that hbp is regulated by *L. pneumophila* Fur and intracellular iron levels. Hickey and Cianciotto, Gene 143:117–121 (1994). Finally, the presence of a potential transcription terminator shortly after the Hbp stop codon suggested that hbp is transcribed as a monocistronic message (Chart A). To confirm this idea, Northern blot analysis was performed using RNA isolated from strain 130b and, as a probe, the hbp-containing NdeI-EcoRV fragment of pEH12 (FIG. 12). *L. pneumophila* expressed a single hbp-hybridizing transcript (data not shown). Importantly, the length of that mRNA was estimated to be 440 bases, a size which is compatible with that of the hbp ORF.

Chart A gives the nucleotide sequence of the hbp region [SEQ ID NO:45] and the predicted amino acid sequence of Hbp [SEQ ID NO:46]. Potential -10 regions for the hbp promoter are in boldface lowercase type, and the area containing possible iron boxes is underlined. The locations of key restriction enzyme recognition sites, the ribosome binding site, and the transcription terminator are also clearly indicated. The putative signal sequence for Hbp is in boldface uppercase type.

chloramphenicol was performed (see FIG. 13B). To simultaneously confirm that the strain contained a $Km^r$ insertion while lacking other vector sequences, pBOC22 was used as the probe. As predicted, this strain, which was designated NU226, had a 2.5-kb hbp-containing NdeI fragment in place of a 0.8-kb hybridizing NdeI fragment (compare lanes c and d). Southern hybridization analysis of genomic DNAs digested with HincII, HindIII, PstI, and PvuI further confirmed that NU226 underwent allelic exchange (FIG. 13B, lanes a and b; and data not shown).

To ascertain whether hbp is associated with hemin binding in *L. pneumophila*, NU226 and 130b were grown on YP-minus-Fe-plus-hemin agar and then compared for their

CHART A

```
                                      Nde I
gaaaaatatccttataaatatgaattagccattgcatatggcaaaagataatctgaaaca     60 attcccgacaacatccttttaaaacggttgcaactgaaaattcaacttgttagtcttttg    120

RBS                              Hinc II
aagattttaactgctaagtaacaaggagaagtaacATGATGTTGAAAACCCAGTTGACT    180
                                    M  M  L  K  T  Q  L  T      8

GCTTTTATCGGTGCTGTAATCTTGGCTGGCTCTTCTTTAGCAAATCCAATAAAACCTGAG    240
 A  F  I  G  A  V  I  L  A  G  S  S  L  A  N  P  I  K  P  E     28

GTATGCCCCAGTGTACCCTCTATTCAATCGGAAGGAATGTCCATGTCTTCTGAAATTTTG    300
 V  C  P  S  V  P  S  I  Q  S  E  G  M  S  M  S  S  E  I  L     48

GAGGGCATGTACATCACCTATAATTTAAGTCATTACAATACCAGTTCAAGCTGGGTGTTT    360
 E  G  M  Y  I  T  Y  N  L  S  H  Y  N  T  S  S  S  W  V  F     68

ATTGTAGGGCCAATCGCAGCTGAAAATGATGATATGGCATTGGCAGAAAGCAATAAATTA    420
 I  V  G  P  I  A  A  E  N  D  D  M  A  L  A  E  S  N  K  L     88

CTTTCAACCATGTCAGGGTCTCCCCATCCGGAAGATGATGGAGAAGGCAATTGGATATGT    480
 L  S  T  M  S  G  S  P  H  P  E  D  D  G  E  G  N  W  I  C    108

CAGTATACGACCAAATCCAAAGATATTATTGCATTTGCCATAGAAGCAGATGATATGCTT    540
 Q  Y  T  T  K  S  K  D  I  I  A  F  A  I  E  A  D  D  M  L    128

Eco RV
TCTCCATTGAAAATGATGAGATATCTCAGAACAATCCGCTGATAAGTGGATAACACCTGC    600
 S  P  L  K  M  M  R  Y  L  R  T  I  R  -                      141

Sac I
ACGGACACGGAAGCATGATTTGCTTCCGTGATTTAACGAATAGTTAAGAGCTC          653
                               [SEQ ID NOS: 45 & 46]
```

3. Construction and Characterization of an *L. pneumophila* hbp Mutant. To ultimately determine whether hbp promotes hemin acquisition by *L. pneumophila*, an hbp mutant was isolated. Specifically, allelic exchange was employed to insertionally inactivate the hbp gene within strain 130b. The plasmid used for this procedure, pBOC22, was constructed in two steps. First, a blunt-end 1.7-kb fragment containing $Km^r$ was introduced into the HincII site of pEH12 to yield pBOC21. As noted above, this DNA insertion into hbp abolished hemin binding in recombinant *E. coli*. Second, the mutated gene was transferred on a SacI-BamHI fragment into the $Cm^r$ and sacB-containing pBOC20. As the next step toward the construction of the mutant, pBOC22 was electroplated into strain 130b, and the transformation mixture was plated onto BCYE agar containing both kanamycin and sucrose. By simultaneously selecting for $Km^r$ and counterselecting against sacB, strains in which the plasmid is lost and the chromosomal hbp is exchanged for its mutated allele can be isolated (see FIG. 13A). To identify a strain that had undergone allelic exchange, Southern hybridization analysis on a $Km^r$, sucrose-resistant clone which had lost its resistance to abilities to remove hemin from solution. The mutant strain displayed a 42% reduction in hemin binding, indicating that although hbp is not essential, it does enhance the acquisition of hemin by Legionella organisms.

To determine whether hbp is required for intracellular infection of macrophages by *L. pneumophila*, we assessed the relative ability of NU226 to infect U937 cells. Regardless of whether the inocula were prepared from YP-minus-Fe-plus hemin or BCYE cultures, the mutant exhibited a 50% infective dose that was comparable to that of the wild-type (data not shown). Furthermore, the intracellular growth pattern of NU226 was nearly identical to that of strain 130b (FIG. 14). To explore the possibility that hbp is important for growth within iron-depleted host cells, the infections of U937 cells were repeated using U937 cells which had been treated with DFX. However, in two experiments, comparable numbers of mutant and wild-type bacteria were recovered after 72 h of incubation (data not shown). Finally, NU226 was not impaired in its ability to infect a protozoan host, the amoeba H. vermiformis (data not shown). Taken together, these results indicate that, although hbp is a promoter of hemin binding, it is not required for intracellular infection by *L. pneumophila*.

4. Distribution of hbp Among *L. pneumophila* Strains and Other Legionella Species. The *L. pneumophila* species consists of 14 serogroups, and the Legionella genus includes 39 species. Dennis, et al., Int. J. Syst. Bacteriol. 43:329–337 (1993). To determine whether hbp is conserved among *L. pneumophila* strains and Legionella species, Southern hybridization analysis was performed using an hbp-specific probe. Under high-stringency conditions, the probe hybridized with DNAs from all *L. pneumophila* strains tested, suggesting that hbp is well conserved within the *L. pneumophila* species (see FIG. 15A). In contrast, hbp was largely absent from other Legionella species. Not only did the probe fail to hybridize with DNAs from these species under high stringency (data not shown); in most cases, it did not even hybridize under reduced-stringency conditions (see FIG. 15B). Curiously, *L. moravica*, an environmental isolate, and *L. hackeliae*, a clinical isolate, were the only species that reacted with the hbp probe. Furthermore, these hybridizations were quite weak compared with those of *L. pneumophila* (FIG. 15B, lanes a, e, and g). In a control Southern blot, DNAs from all of the Legionella spp. hybridized, as expected, with a mip probe under low-stringency conditions (data not shown). Cianciotto, et al., Infect. Immun. 58:2912–2918 (1990). Taken together, these experiments indicate that although hbp is not required for intracellular infection, it is nearly exclusive to the most pathogenic of Legionella species.

C. Discussion

With the results presented here, *L. pneumophila* now shares with a number of other pathogens the ability to bind and utilize hemin as an iron source. Furthermore, the capacity of hemin to replace ferric iron in a CDM indicates that it can be the sole source of iron. This experience with hemin also suggests that *L. pneumophila* can bind and use a variety of heme-containing compounds. Feeley, et al., J. Clin. Microbiol. 8:320–325 (1978); Otto, et al., Crit. Rev. Microbiol. 18:217–233 (1992); Wooldridge and Williams, FEMS Microbiol. Rev. 12:325–348 (1993). Since cultures supplemented with hemin did not achieve the same degree of growth as those supplemented with ferric $PP_i$, ferric salts should nevertheless remain the preferred iron component of Legionella media. The level of hemin binding associated with the virulent strain 130b (i.e., 50 to 60% of added hemin) is quite comparable to those of other pathogens. Daskaleros and Payne, Infect. Immun. 55:1393–1398 (1987); Deneer and Potter, Infect. Immun. 57:798–804 (1989); Genco, et al., Infect. Immun. 62:2885–2892 (1994); Hanson and Hansen, Mol. Microbiol. 5:267–278 (1991). In other systems, hemin binding is followed by the internalization of the heme moiety, with the extraction of iron occurring within an intracellular compartment. Daskaleros, et al., Infect. Immun. 59:2706–2711 (1991); Mills and Payne, J. Bacteriol. 177:3004–3009 (1995); Stojiljkovic and Hantke, Mol. Microbiol. 13:719–732 (1994). However, a recent report on *N. gonorrhoeae* indicates that, in some cases, iron is extracted from hemin at the cell surface. Desai P. J., et al., Infect. Immun. 63:4634–4641 (1995). Clearly, transport studies with radiolabeled hemin are needed to ascertain which heme iron assimilation pathway is operative in the legionellae. However, the inability of hemin to restore growth to strain 130b cultures containing the ferric iron chelator DFX (data not shown) suggests that *L. pneumophila* is akin to *N. gonorrhoeae*. The observation that legionellae harvested from YP-minus-Fe-plus-hemin media exhibited a binding activity greater than those harvested from BCYE media warrants additional comment. Two explanations for this observation can be offered. First, it is possible that in Legionella, as in other microbes, the presence of hemin (in the YP medium) induces the expression of hemin acquisition functions. Carman, et al., Infect. Immun. 58:4016–4019 (1990); Genco, et al., Infect. Immun. 62:2885–2892 (1994). Alternately, the presence of a high level of iron (in the BCYE medium) represses hemin-binding activity. Henderson and Payne, J. Bacteriol. 176:3269–3277 (1994); Perry, Trends Microbiol. 1:142–147 (1993); Worst, et al., Infect. Immun. 63:4161–4165 (1995). The latter possibility is supported by the placement of an iron box-like sequence upstream of hbp.

In *L. pneumophila*, as in other microbes, hemin binding and utilization undoubtedly require the action of numerous genes. For five reasons, it is strongly suspected that the newly identified hbp is one of those genes. First, when cloned into *E. coli*, it promoted hemin binding both on plates and in liquid. Second, the extent of that binding was comparable to what is observed with genes cloned from other bacteria. Hanson and Hansen, Mol. Microbiol. 5:267–278 (1991). Third, the cloned hbp also conferred Congo red binding, which is a trait often associated with hemin binding. Daskaleros and Payne, Infect. Immun. 55:1393–1398 (1987); Deneer and Potter, Infect. Immun. 57:798–804 (1989); Genco, et al., Infect. Immun. 62:2885–2892 (1994); Kay, et al., J. Bacteriol. 164:1332–1336 (1985); Stugard, et al., Infect. Immun. 57:3534–3539 (1989). Fourth, the predicted product of hbp appears to be secreted, a characteristic that is common to proteins which are specifically associated with hemin acquisition. Bramanti and Holt, J. Bacteriol. 175:7413–7420 (1993); Cope, et al., J. Bacteriol. 177:2644–2653 (1995); Elkins, et al., Infect. Immun. 63:2194–2200 (1995); Hanson and Hansen, Mol. Microbiol. 5:267–278 (1991); Henderson and Payne, J. Bacteriol. 176:3269–3277 (1994); Lewis and Dyer, J. Bacteriol. 177:1299–1306 (1995); Mills and Payne, J. Bacteriol. 177:3004–3009 (1995); Stojiljkovic and Hantke, Mol. Microbiol. 13:719–732 (1994). Fifth, and most importantly, an *L. pneumophila* strain containing a DNA insertion within the monocistronic hbp displayed a 43% reduction in hemin binding. It is not clear how hbp (Hbp) potentiates hemin acquisition in *L. pneumophila* or *E. coli*. In one scenario, Hbp is the surface protein that directly binds hemin. In a second scenario, it facilitates the expression or activity of another, possibly conserved, component of the gram-negative cell wall. The fact that the Legionella hbp mutant still exhibited some hemin binding would tend to support the second scenario. The absence of a second membrane-spanning domain within Hbp is most compatible with a periplasmic rather than outer membrane location for the protein. A hemin-binding protein of *H. influenze* which was identified by screening a genomic library on hemin plates is believed to be located, at least in part, within the periplasm. Hanson and Hansen, Mol. Microbiol. 5:267–278 (1991).

In three different assays, the *L. pneumophila* hbp mutant was not impaired in its ability to infect eukaryotic hosts, clearly indicating that hbp is not required for intracellular infection. This result diminishes significantly but does not eliminate the possibility that hbp encodes a virulence factor; i.e., only experimental animal infections can ascertain whether hbp promotes (extracellular) survival and/or growth in vivo. For two reasons, this result also does not necessarily mean that hemin acquisition and utilization are not critical for intracellular *L. pneumophila* growth. On the one hand, the residual hemin binding displayed by the mutant may suffice inside host cells. On the other hand, intracellular legionellae might express other genes which can restore hemin binding to its full capacity.

Southern hybridization analysis indicated that hbp sequences are nearly limited to the L. pneumophila species. This type of gene distribution is rather peculiar. When assessed, all previously identified *L. pneumophila* genes, including flaA, fur, htp, lly, mip, ompS, and ppLa (pal), have had homologs in all or virtually all other Legionella species. Bender, et al., Infect. Immun. 59:3333–3336 (1991); Cianciotto, et al., Infect. Immun. 58:2912–2918 (1990); Heuner, et al., Infect. Immun. 63:2499–2507 (1995); Hickey and Cianciotto, Gene 143:117–121 (1994); Hoffman, et al., Infect. Immn. 57:1731–1739 (1989); Hoffman, et al., J. Bacteriol. 174:914–920 (1992); Ott, et al., Microb. Pathog. 11:357–365 (1991). Although the biological significance of this observation is unclear, the limited distribution of hbp among the legionellae warrants its use as a diagnostic reagent. Currently, mip primers are used for the PCR detection of *L. pneumophila* within water and clinical samples. Atlas, et al., Appl. Environ. Microbiol. 61:1208–1213 (1995); Bej, et al., Appl. Environ. Microbiol. 57:597–600 (1991); Jaulhac, et al., J. Clin. Microbiol. 30:920–924 (1992); King, et al., Infect. Immun. 59:758–763 (1991); Lindsay, et al., J. Clin. Microbiol. 32:3068–3069 (1994); Oshiro, et al., Can. J. Microbiol. 40:495–499 (1994). However, in several instances, these primers amplify DNAs (i.e., mip-like genes) from other Legionella species. Atlas, et al., Appl. Environ. Microbiol. 61:1208–1213 (1995); Cianciotto, et al., Infect. Immun. 58:2912–2918 (1990); Jaulhac, et al., J. Clin. Microbiol. 30:920–924 (1992); Oshiro, et al., Can. J. Microbiol. 40:495–499 (1994). Thus, hbp primers should enhance the specificity of *L. pneumophila* PCR detection protocols.

We claim:

1. A frgA gene of *Legionela pneumophila* or a fragment thereof at least 18 basepairs in length.

2. The gene of claim 1 which is the frgA gene of *L. pneumophila* strain 130b.

3. A non-chromosome nucleic acid molecule having a sequence selected so that the nucleic acid molecule specially hybridizes under conditions of high stringency to a frgA gene or an mRNA encoded by a frgA gene.

4. The molecule of claim 3 which is labeled.

5. The molecule of claim 3 which has the sequence given in FIG. 7 (SEQ ID NO:4) or a fragment thereof.

6. A kit for detecting or quantitating *Legionella pneumophila* comprising a container holding at least one nucleic acid molecule of claim 3.

7. The kit of claim 6 wherein the molecule is labeled.

8. The kit of claim 6 wherein the molecule has the sequence given in FIG. 7 (SEQ ID NO:4) or a fragment thereof.

9. A method of detecting or quantitating *Legionela pneumophila* comprising:

obtaining DNA from a sample suspected of containing *L. pneumophila;* amplifying the DNA by polymerase chain reaction using a plurality of nucleic acid molecules according to claim 3 as primers; and detecting or quantitating the *L. pneumophila* by detecting or quantitating the amplified DNA.

10. The method of claim 9 wherein the nucleic acid molecules are labeled to allow for detection or quantitation of the amplified DNA.

11. The method of claim 9 wherein labeled nucleotides are used during the polymerase chain reaction to allow for detection or quantitation of the amplified DNA.

12. The method of claim 9 wherein a nucleic acid molecule of claim 7 which hybridizes to the amplified DNA is added after the polymerase chain reaction to allow for detection or quantitation of the amplified DNA.

13. The method of claim 9 wherein the observation of a DNA of the expected size of the amplified DNA allows for detection or quantitation of the amplified DNA.

14. A method of detecting or quantitating *Legionela pneumophila* comprising:

obtaining DNA or RNA from a sample suspected of containing *L. pneumophila;* contacting the DNA or RNA with a nucleic acid molecule of claim 3 so that the molecule hybridizes to the DNA or RNA; and detecting or quantitating the *L. pneumophila* by detecting or quantitating the nucleic acid molecule hybridized to the DNA or RNA.

* * * * *

UNITED STATES PATENT AND TRADEMARK OFFICE
CERTIFICATE OF CORRECTION

PATENT NO. : 5,935,782
DATED : August 10, 1999
INVENTOR(S) : Cianciotto et al.

It is certified that error appears in the above-identified patent and that said Letters Patent is hereby corrected as shown below:

In Claim 3, delete "specially" and insert –specifically– therefor.

Signed and Sealed this

Twenty-first Day of December, 1999

Attest:

Q. TODD DICKINSON

*Attesting Officer*    *Acting Commissioner of Patents and Trademarks*

```
                          SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Primer"

(xi) SEQUENCE DESCRIPTION: SEQ ID NO:1:

CCCAGTCACG ACGTTGTAAA ACG                                              23

(2) INFORMATION FOR SEQ ID NO:2:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Primer"

(xi) SEQUENCE DESCRIPTION: SEQ ID NO:2:

AGCGGATAAC AATTTCACAC AG                                               22

(2) INFORMATION FOR SEQ ID NO:3:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Primer"

(xi) SEQUENCE DESCRIPTION: SEQ ID NO:3:

CCTTAACTTA ATGATTTTTA C                                                21

(2) INFORMATION FOR SEQ ID NO:4:

(i) SEQUENCE CHARACTERISTICS:
```

(A) LENGTH: 1980 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:4:

```
ATTTAACTCA GAATACAGAA ACTTTTTATC CAAAATCAAA CTCTATTGCC AATTAATAAT        60

ATTTTATTTG CCCCACCTCT TGCAAATGAG AATGATTATC ATTTATATTT AATTTATAAC       120

AAAATAATCC TTCAGGAGAT AATA ATG GCC CTG GCG TAC GGT AAT TTT CAT         171
                          Met Ala Leu Ala Tyr Gly Asn Phe His
                            1               5

GAA CTC AGC CAT CAA TTA CGC TTT TTA CTA TTT GAA ATT GGC ATA GGA         219
Glu Leu Ser His Gln Leu Arg Phe Leu Leu Phe Glu Ile Gly Ile Gly
 10              15                  20                  25

CTA CCA CAA AAT AGT GTG GAT TAT TTT ATT ACC TTA GCT CAT AAA AAT         267
Leu Pro Gln Asn Ser Val Asp Tyr Phe Ile Thr Leu Ala His Lys Asn
                 30                  35                  40

ACC CTG AAG CGT TTA CAG CAT GCC TCC ATT AAG GAA GGA TTA ATT CAA         315
Thr Leu Lys Arg Leu Gln His Ala Ser Ile Lys Glu Gly Leu Ile Gln
             45                  50                  55

TCA GCC ATT GCA AGT CAC CAT ATC CAT GAT TTC ATT GAC CAA TTG CAG         363
Ser Ala Ile Ala Ser His His Ile His Asp Phe Ile Asp Gln Leu Gln
         60                  65                  70

ATA AAA CTG AAA AAT TCA ATG CCG GAA AGT AAG TTT TTT CAA TGG CGA         411
Ile Lys Leu Lys Asn Ser Met Pro Glu Ser Lys Phe Phe Gln Trp Arg
     75                  80                  85

AAA ATC AGG GAA GCA TTA GAT GAA TCG ATT GCC AAT GAG GCT TTG GCT         459
Lys Ile Arg Glu Ala Leu Asp Glu Ser Ile Ala Asn Glu Ala Leu Ala
 90                  95                 100                 105

TAC GCC TAC AGG CAA AAC TGG AAC ACC CAA TTA AGA AAT GAA GCC ATG         507
Tyr Ala Tyr Arg Gln Asn Trp Asn Thr Gln Leu Arg Asn Glu Ala Met
                110                 115                 120

CAC TAC AAG AGT CTG TGG ACA TGG ATA AAT AAT GAA CTA TCT CCG TAT         555
His Tyr Lys Ser Leu Trp Thr Trp Ile Asn Asn Glu Leu Ser Pro Tyr
            125                 130                 135

CAA ACG TTA TTA TTT CTG GAA CAA TGG GGC AGT TTG AGG CAT CCC TAT         603
Gln Thr Leu Leu Phe Leu Glu Gln Trp Gly Ser Leu Arg His Pro Tyr
        140                 145                 150

CAC CCA GCA TTC AGC GCA AAA ACA GGG TTT ACG CGA AGA GAA GTA CTC         651
His Pro Ala Phe Ser Ala Lys Thr Gly Phe Thr Arg Arg Glu Val Leu
    155                 160                 165

CAA AAC TCT CCC GAA TTC CAG GCC AAA GTC AGT GTA CAT TGG TGT GCA         699
Gln Asn Ser Pro Glu Phe Gln Ala Lys Val Ser Val His Trp Cys Ala
170                 175                 180                 185

TTA AAT AAA ACA AAA ATT CAG TCA ATA AGC CCA AAA ATT GAT TAT GCC         747
Leu Asn Lys Thr Lys Ile Gln Ser Ile Ser Pro Lys Ile Asp Tyr Ala
                190                 195                 200

AAC CAA ATT TCT CAA GAA TTT CCC AAA GAA TAT TTT TAT TGG CGT GAA         795
Asn Gln Ile Ser Gln Glu Phe Pro Lys Glu Tyr Phe Tyr Trp Arg Glu
            205                 210                 215

AAA TTG TTA TTT AGC CAC ATC AAC CCT GAT GAT TAT TAT CCA ATT CCT         843
Lys Leu Leu Phe Ser His Ile Asn Pro Asp Asp Tyr Tyr Pro Ile Pro
        220                 225                 230

GTT CAC CCT TGG CAG TGG AGG AAT CAA TTA CAA ATG GCG TTT GCA TCT         891
Val His Pro Trp Gln Trp Arg Asn Gln Leu Gln Met Ala Phe Ala Ser
    235                 240                 245

TTA ATT GAT AAT AAA TCC CTC ATC TTG TTA CCT CAT CAC CAA ACA CTA         939
Leu Ile Asp Asn Lys Ser Leu Ile Leu Leu Pro His His Gln Thr Leu
250                 255                 260                 265
```

```
ATA CCT TCT TTA TCA CCT GAT ATT ATG ATG CCA ACA CAA TCC ACT CAA        987
Ile Pro Ser Leu Ser Pro Asp Ile Met Met Pro Thr Gln Ser Thr Gln
            270                 275                 280

TGT ACA CTT AAA CTG GCT ACC ACT TTA AGC ACC TCA ATG GCT GGA AAA       1035
Cys Thr Leu Lys Leu Ala Thr Thr Leu Ser Thr Ser Met Ala Gly Lys
            285                 290                 295

CTT GAT AAT TCT AAT GAT ATG GTA TTG CTT ACC AGA TGG ATC GAT TCC       1083
Leu Asp Asn Ser Asn Asp Met Val Leu Leu Thr Arg Trp Ile Asp Ser
            300                 305                 310

CTG TTA GCA AAA ACA AAC TAT TAC CAA AAT ACC TTG TTT ATA TGT AAA       1131
Leu Leu Ala Lys Thr Asn Tyr Tyr Gln Asn Thr Leu Phe Ile Cys Lys
            315                 320                 325

AAC CTG GAG AGC ATG AGC GCC TAT GAT CAA ACT CTC TCT GAA TGC AAT       1179
Asn Leu Glu Ser Met Ser Ala Tyr Asp Gln Thr Leu Ser Glu Cys Asn
330                 335                 340                 345

CGA GTA AAA TTA TTG TTT GGC TTA TAT CAA AAC CCA CTC CAC AAA ATA       1227
Arg Val Lys Leu Leu Phe Gly Leu Tyr Gln Asn Pro Leu His Lys Ile
            350                 355                 360

AGA CAG GAT CAA AGA GCA GTT CCA TTA CCT GCC CTA TTA ACT GAT TCC       1275
Arg Gln Asp Gln Arg Ala Val Pro Leu Pro Ala Leu Leu Thr Asp Ser
            365                 370                 375

CCT TGT AGC AAT ACA CCA TTA CTC ATT GAA ATT ATT AAA GCT AGC GGC       1323
Pro Cys Ser Asn Thr Pro Leu Leu Ile Glu Ile Ile Lys Ala Ser Gly
            380                 385                 390

CTG CAC CCA ACG ACT TAT TTC ACT GAA TAT TGT TAT AAG ATG TTA TTT       1371
Leu His Pro Thr Thr Tyr Phe Thr Glu Tyr Cys Tyr Lys Met Leu Phe
            395                 400                 405

GGA CAA TTG CAT CTA TTG CTA AAA TAT GGA TTA GCA CTA GAA GTG GAG       1419
Gly Gln Leu His Leu Leu Leu Lys Tyr Gly Leu Ala Leu Glu Val Glu
410                 415                 420                 425

CAA CAC AAT ATT TTA GTC ATC TTC GAT GAC AAT AAA CCT CAG GGG ATA       1467
Gln His Asn Ile Leu Val Ile Phe Asp Asp Asn Lys Pro Gln Gly Ile
            430                 435                 440

ATT ATA AAA GAG CCA AAC AAC CTT AAG CTA TGC AAT CAT GAA CTG TTT       1515
Ile Ile Lys Glu Pro Asn Asn Leu Lys Leu Cys Asn His Glu Leu Phe
            445                 450                 455

AAA AAC GTT CAA AAA CCC AAC GCT CCA GAC TCT TTA TCC ATC TAT ACA       1563
Lys Asn Val Gln Lys Pro Asn Ala Pro Asp Ser Leu Ser Ile Tyr Thr
            460                 465                 470

AAA GAT CTT AAT CAG GTT AGA ACC CTT TTC ATC CAG GGA ACA TTA AAA       1611
Lys Asp Leu Asn Gln Val Arg Thr Leu Phe Ile Gln Gly Thr Leu Lys
475                 480                 485

AAT CAT CTA CAT CAC TTG ATT GGC TGT TTA CGT AAT GAG TAT CAG ATT       1659
Asn His Leu His His Leu Ile Gly Cys Leu Arg Asn Glu Tyr Gln Ile
490                 495                 500                 505

CCT TCA AGA ACC TTA TGG GGA TTA GCT CGC CAA GTC ATG CAA ACT GTA       1707
Pro Ser Arg Thr Leu Trp Gly Leu Ala Arg Gln Val Met Gln Thr Val
            510                 515                 520

TTT AAA GAC TTA TCC AAA GAC ATT GAT CCG CGT ATT CTA AGT TGG CAA       1755
Phe Lys Asp Leu Ser Lys Asp Ile Asp Pro Arg Ile Leu Ser Trp Gln
            525                 530                 535

CAA CAT CTA TTG CTT CAT GAT AAC TGG GAG CAT CAA CCT GAA TTG TTA       1803
Gln His Leu Leu Leu His Asp Asn Trp Glu His Gln Pro Glu Leu Leu
            540                 545                 550

TTA AGT CTG CAT TCC AAA ATC AAT CGA AAT ATT ACA ATA AAG GAA TAC       1851
Leu Ser Leu His Ser Lys Ile Asn Arg Asn Ile Thr Ile Lys Glu Tyr
            555                 560                 565

AAC CCA TTA TCA GAG ATC T AAGCTCTACT GGACTTACGA AAAACCCCAT            1900
Asn Pro Leu Ser Glu Ile
570                 575
```

```
GCGCTCTTGT TCCAATACTA AAATATGAGA ACTTCTCGAG GCCGGGATGT GGATACTATG      1960

AGTCAATAAA TCCCAATTGA                                                   1980

(2) INFORMATION FOR SEQ ID NO:5:

(i) SEQUENCE CHARACTERISTICS:
        (A) LENGTH: 575 amino acids
        (B) TYPE: amino acid
        (D) TOPOLOGY: linear (ii) MOLECULE TYPE: protein (xi) SEQUENCE DESCRIPTION: SEQ ID NO:5:

Met Ala Leu Ala Tyr Gly Asn Phe His Glu Leu Ser His Gln Leu Arg
 1               5                  10                  15

Phe Leu Leu Phe Glu Ile Gly Ile Gly Leu Pro Gln Asn Ser Val Asp
                20                  25                  30

Tyr Phe Ile Thr Leu Ala His Lys Asn Thr Leu Lys Arg Leu Gln His
            35                  40                  45

Ala Ser Ile Lys Glu Gly Leu Ile Gln Ser Ala Ile Ala Ser His His
 50                  55                  60

Ile His Asp Phe Ile Asp Gln Leu Gln Ile Lys Leu Lys Asn Ser Met
 65                  70                  75                  80

Pro Glu Ser Lys Phe Phe Gln Trp Arg Lys Ile Arg Glu Ala Leu Asp
                85                  90                  95

Glu Ser Ile Ala Asn Glu Ala Leu Ala Tyr Ala Tyr Arg Gln Asn Trp
                100                 105                 110

Asn Thr Gln Leu Arg Asn Glu Ala Met His Tyr Lys Ser Leu Trp Thr
            115                 120                 125

Trp Ile Asn Asn Glu Leu Ser Pro Tyr Gln Thr Leu Leu Phe Leu Glu
130                 135                 140

Gln Trp Gly Ser Leu Arg His Pro Tyr His Pro Ala Phe Ser Ala Lys
145                 150                 155                 160

Thr Gly Phe Thr Arg Arg Glu Val Leu Gln Asn Ser Pro Glu Phe Gln
                165                 170                 175

Ala Lys Val Ser Val His Trp Cys Ala Leu Asn Lys Thr Lys Ile Gln
                180                 185                 190

Ser Ile Ser Pro Lys Ile Asp Tyr Ala Asn Gln Ile Ser Gln Glu Phe
            195                 200                 205

Pro Lys Glu Tyr Phe Tyr Trp Arg Glu Lys Leu Leu Phe Ser His Ile
210                 215                 220

Asn Pro Asp Asp Tyr Tyr Pro Ile Pro Val His Pro Trp Gln Trp Arg
225                 230                 235                 240

Asn Gln Leu Gln Met Ala Phe Ala Ser Leu Ile Asp Asn Lys Ser Leu
                245                 250                 255

Ile Leu Leu Pro His His Gln Thr Leu Ile Pro Ser Leu Ser Pro Asp
                260                 265                 270

Ile Met Met Pro Thr Gln Ser Thr Gln Cys Thr Leu Lys Leu Ala Thr
            275                 280                 285

Thr Leu Ser Thr Ser Met Ala Gly Lys Leu Asp Asn Ser Asn Asp Met
290                 295                 300

Val Leu Leu Thr Arg Trp Ile Asp Ser Leu Leu Ala Lys Thr Asn Tyr
305                 310                 315                 320

Tyr Gln Asn Thr Leu Phe Ile Cys Lys Asn Leu Glu Ser Met Ser Ala
                325                 330                 335
```

```
Tyr Asp Gln Thr Leu Ser Glu Cys Asn Arg Val Lys Leu Leu Phe Gly
            340                 345                 350

Leu Tyr Gln Asn Pro Leu His Lys Ile Arg Gln Asp Gln Arg Ala Val
            355                 360                 365

Pro Leu Pro Ala Leu Leu Thr Asp Ser Pro Cys Ser Asn Thr Pro Leu
370                 375                 380

Leu Ile Glu Ile Ile Lys Ala Ser Gly Leu His Pro Thr Thr Tyr Phe
385                 390                 395                 400

Thr Glu Tyr Cys Tyr Lys Met Leu Phe Gly Gln Leu His Leu Leu
                405                 410                 415

Lys Tyr Gly Leu Ala Leu Glu Val Glu Gln His Asn Ile Leu Val Ile
            420                 425                 430

Phe Asp Asp Asn Lys Pro Gln Gly Ile Ile Ile Lys Glu Pro Asn Asn
                435                 440                 445

Leu Lys Leu Cys Asn His Glu Leu Phe Lys Asn Val Gln Lys Pro Asn
450                 455                 460

Ala Pro Asp Ser Leu Ser Ile Tyr Thr Lys Asp Leu Asn Gln Val Arg
465                 470                 475                 480

Thr Leu Phe Ile Gln Gly Thr Leu Lys Asn His Leu His Leu Ile
                485                 490                 495

Gly Cys Leu Arg Asn Glu Tyr Gln Ile Pro Ser Arg Thr Leu Trp Gly
            500                 505                 510

Leu Ala Arg Gln Val Met Gln Thr Val Phe Lys Asp Leu Ser Lys Asp
            515                 520                 525

Ile Asp Pro Arg Ile Leu Ser Trp Gln Gln His Leu Leu Leu His Asp
530                 535                 540

Asn Trp Glu His Gln Pro Glu Leu Leu Leu Ser Leu His Ser Lys Ile
545                 550                 555                 560

Asn Arg Asn Ile Thr Ile Lys Glu Tyr Asn Pro Leu Ser Glu Ile
                565                 570                 575

(2) INFORMATION FOR SEQ ID NO:6:

(i) SEQUENCE CHARACTERISTICS:
        (A) LENGTH: 44 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Met Ile Leu Pro Ser Glu Lys Ser Ala Thr Asp Val Ala Ala Gln Cys
1               5                   10                  15

Phe Leu Asn Ala Leu Ile Arg Glu Thr Lys Asp Trp Gln Leu Ala Glu
                20                  25                  30

Tyr Pro Pro Asp Glu Leu Ile Ile Pro Leu Asp Glu
            35                  40

(2) INFORMATION FOR SEQ ID NO:7:

(i) SEQUENCE CHARACTERISTICS:
        (A) LENGTH: 47 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:
```

```
Met Ala Leu Ala Tyr Gly Asn Phe His Glu Leu Ser His Gln Leu Arg
1               5                   10                  15

Phe Leu Leu Phe Glu Ile Gly Ile Gly Leu Pro Gln Asn Ser Val Asp
                20                  25                  30

Tyr Phe Ile Thr Leu Ala His Lys Asn Thr Leu Lys Arg Leu Gln
            35                  40                  45
```

(2) INFORMATION FOR SEQ ID NO:8:

(i) SEQUENCE CHARACTERISTICS:
        (A) LENGTH: 40 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Met Asn His Lys Asp Trp Asp Leu Val Asn Arg Arg Leu Val Ala Lys
1               5                   10                  15

Met Leu Ser Glu Leu Glu Tyr Glu Gln Val Phe His Ala Glu Ser Gln
                20                  25                  30

Gly Asp Asp Arg Tyr Cys Ile Asn
            35                  40
```

(2) INFORMATION FOR SEQ ID NO:9:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Gln Lys Ser Leu His Phe Arg Val Ala Tyr Phe Ser Pro Thr Gln His
1               5                   10                  15

His Arg Phe Ala Phe Pro Ala His Leu Val Thr Ala Ser Gly Ser Tyr
                20                  25                  30

Pro Val Asp Phe Thr Thr Leu Ser Arg Leu Ile Ile Asp Lys Leu Arg
            35                  40                  45

His Gln
50
```

(2) INFORMATION FOR SEQ ID NO:10:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
His Ala Ser Ile Lys Glu Gly Leu Ile Gln Ser Ala Ile Ala Ser His
1               5                   10                  15

His Ile His Asp Phe Ile Asp Gln Leu Gln Ile Lys Leu Lys Asn Ser
                20                  25                  30

Met Pro Glu Ser Lys Phe Phe Gln Trp Arg Lys Ile Arg Glu Ala Leu
            35                  40                  45

Asp Glu
50
```

(2) INFORMATION FOR SEQ ID NO:11:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Leu Pro Gly Ala Gln Trp Arg Phe Ile Ala Glu Arg Gly Ile Trp Gly
1               5                  10                  15

Trp Leu Trp Ile Asp Ala Gln Thr Leu Arg Cys Ala Asp Glu Pro Val
            20                  25                  30

Leu Ala Gln Thr Leu Leu Met Gln Leu Lys Gln Val Leu Ser Met Ser
        35                  40                  45

Asp Ala
    50
```

(2) INFORMATION FOR SEQ ID NO:12:

(i) SEQUENCE CHARACTERISTICS:
        (A) LENGTH: 47 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

```
Leu Phe Leu Pro Val Pro Leu Cys Glu Thr Phe His Gln Arg Val Leu
1               5                  10                  15

Glu Ser Tyr Ala His Thr Gln Gln Thr Ile Asp Ala Arg His Asp Trp
            20                  25                  30

Ala Ile Leu Arg Glu Lys Ala Leu Asn Phe Gly Glu Ala Glu Gln
        35                  40                  45
```

(2) INFORMATION FOR SEQ ID NO:13:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

```
Ser Ile Ala Asn Glu Ala Leu Ala Tyr Ala Tyr Arg Gln Asn Trp Asn
1               5                  10                  15

Thr Gln Leu Arg Asn Glu Ala Met His Tyr Lys Ser Leu Trp Thr Trp
            20                  25                  30

Ile Asn Asn Glu Leu Ser Pro Tyr Gln Thr Leu Leu Phe Leu Glu Gln
        35                  40                  45

Trp Gly
    50
```

(2) INFORMATION FOR SEQ ID NO:14:

(i) SEQUENCE CHARACTERISTICS:
        (A) LENGTH: 44 amino acids
        (B) TYPE: amino acid
        (C) STRANDEDNESS:

(D) TOPOLOGY: linear (ii) MOLECULE TYPE: peptide (xi) SEQUENCE DESCRIPTION: SEQ ID NO:14:

```
Thr Val Ala Glu His Met Gln Asp Leu Tyr Ala Thr Leu Leu Gly Asp
1               5                   10                  15
Leu Gln Leu Leu Lys Ala Arg Arg Gly Leu Ser Ala Ser Asp Leu Ile
            20                  25                  30
Asn Leu Asn Ala Asp Arg Leu Gln Cys Leu Leu Ser
        35                  40
```

(2) INFORMATION FOR SEQ ID NO:15:

(i) SEQUENCE CHARACTERISTICS:
        (A) LENGTH: 44 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
Ala Leu Leu Thr Gly His Ala Phe His Pro Ala Pro Lys Ser His Glu
1               5                   10                  15
Pro Phe Asn Arg Gln Glu Ala Glu Arg Tyr Leu Pro Asp Met Ala Pro
            20                  25                  30
His Phe Pro Leu Arg Trp Phe Ser Val Asp Lys Thr
        35                  40
```

(2) INFORMATION FOR SEQ ID NO:16:

(i) SEQUENCE CHARACTERISTICS:
        (A) LENGTH: 42 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
Ser Leu Arg His Pro Tyr His Pro Ala Phe Ser Ala Lys Thr Gly Phe
1               5                   10                  15
Thr Arg Arg Glu Val Leu Gln Asn Ser Pro Glu Phe Gln Ala Lys Val
            20                  25                  30
Ser Val His Trp Cys Ala Leu Asn Lys Thr
        35                  40
```

(2) INFORMATION FOR SEQ ID NO:17:

(i) SEQUENCE CHARACTERISTICS:
        (A) LENGTH: 46 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
Gly His Pro Lys Phe Val Phe Asn Lys Gly Arg Arg Gly Trp Gly Lys
1               5                   10                  15
Glu Ala Leu Glu Arg Tyr Ala Pro Glu Tyr Ala Asn Thr Phe Arg Leu
            20                  25                  30
His Trp Leu Ala Val Lys Arg Glu His Met Ile Trp Arg Cys
        35                  40                  45
```

(2) INFORMATION FOR SEQ ID NO:18:

(i) SEQUENCE CHARACTERISTICS:
        (A) LENGTH: 44 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

```
Gln Ile Ala Gly Glu Ser Leu His Leu Asn Leu Gln Gln Arg Leu Thr
 1               5                  10                  15
Arg Phe Ala Ala Glu Asn Ala Pro Gln Leu Leu Asn Glu Leu Ser Asp
            20                  25                  30
Asn Gln Trp Leu Phe Pro Leu Arg Pro Trp Gln Gly
        35                  40
```

(2) INFORMATION FOR SEQ ID NO:19:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

```
Lys Ile Gln Ser Ile Ser Pro Lys Ile Asp Tyr Ala Asn Gln Ile Ser
 1               5                  10                  15
Gln Glu Phe Pro Lys Glu Tyr Phe Tyr Trp Arg Glu Lys Leu Leu Phe
            20                  25                  30
Ser His Ile Asn Pro Asp Asp Tyr Tyr Pro Ile Pro Val His Pro Trp
        35                  40                  45
Gln Trp
 50
```

(2) INFORMATION FOR SEQ ID NO:20:

(i) SEQUENCE CHARACTERISTICS:
        (A) LENGTH: 45 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

```
Asp Asn Glu Met Asp Ile His Gln Leu Leu Thr Ala Ala Met Asp Pro
 1               5                  10                  15
Gln Glu Phe Ala Arg Phe Ser Gln Val Trp Gln Glu Asn Gly Leu Asp
            20                  25                  30
His Asn Trp Leu Pro Leu Pro Val His Pro Trp Gln Trp
        35                  40                  45
```

(2) INFORMATION FOR SEQ ID NO:21:

(i) SEQUENCE CHARACTERISTICS:
        (A) LENGTH: 48 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Glu Tyr Leu Phe Gln Gln Val Trp Cys Gln Ala Leu Phe Ala Lys Gly
1               5                   10                  15

Leu Ile Arg Asp Leu Gly Glu Ala Gly Thr Ser Trp Leu Pro Thr Thr
                20                  25                  30

Ser Ser Arg Ser Leu Tyr Cys Ala Thr Ser Arg Asp Met Ile Lys Phe
                35                  40                  45

(2) INFORMATION FOR SEQ ID NO:22:

(i) SEQUENCE CHARACTERISTICS:
        (A) LENGTH: 45 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Arg Asn Gln Leu Gln Met Ala Phe Ala Ser Leu Ile Asp Asn Lys Ser
1               5                   10                  15

Leu Ile Leu Leu Pro His His Gln Thr Leu Ile Pro Ser Leu Ser Pro
                20                  25                  30

Asp Ile Met Met Pro Thr Gln Ser Thr Gln Cys Thr Leu
                35                  40                  45

(2) INFORMATION FOR SEQ ID NO:23:

(i) SEQUENCE CHARACTERISTICS:
        (A) LENGTH: 47 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

Gln Glu Lys Ile Ala Thr Asp Phe Ile Ala Asp Phe Gly Glu Gly Arg
1               5                   10                  15

Met Val Ser Leu Gly Glu Phe Gly Asp Gln Trp Leu Ala Gln Gln Ser
                20                  25                  30

Leu Arg Thr Leu Thr Asn Ala Ser Arg Arg Gly Gly Leu Asp Ile
                35                  40                  45

(2) INFORMATION FOR SEQ ID NO:24:

(i) SEQUENCE CHARACTERISTICS:
        (A) LENGTH: 47 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Ser Leu Ser Val Arg Leu Thr Asn Ser Val Arg Thr Leu Ser Val Lys
1               5                   10                  15

Glu Val Glu Arg Gly Met Arg Leu Ala Arg Leu Ala Gln Thr Asp Gly
                20                  25                  30

Trp Gln Met Leu Gln Ala Arg Phe Pro Thr Phe Arg Val Met Gln
                35                  40                  45

(2) INFORMATION FOR SEQ ID NO:25:

(i) SEQUENCE CHARACTERISTICS:
    (A) LENGTH: 47 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:25:

```
Lys Leu Ala Thr Thr Leu Ser Thr Ser Met Ala Gly Lys Leu Asp Asn
1               5                   10                  15

Ser Asn Asp Met Val Leu Leu Thr Arg Trp Ile Asp Ser Leu Leu Ala
            20                  25                  30

Lys Thr Asn Tyr Tyr Gln Asn Thr Leu Phe Ile Cys Lys Asn Leu
        35                  40                  45
```

(2) INFORMATION FOR SEQ ID NO:26:

(i) SEQUENCE CHARACTERISTICS:
        (A) LENGTH: 48 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

```
Lys Leu Pro Leu Thr Ile Tyr Asn Thr Ser Cys Tyr Arg Gly Ile Pro
1               5                   10                  15

Gly Arg Tyr Ile Ala Ala Gly Pro Leu Ala Ser Arg Trp Leu Gln Gln
            20                  25                  30

Val Phe Ala Thr Asp Ala Thr Leu Val Gln Ser Gly Ala Val Ile Leu
        35                  40                  45
```

(2) INFORMATION FOR SEQ ID NO:27:

(i) SEQUENCE CHARACTERISTICS:
        (A) LENGTH: 42 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

```
Glu Asp Asp Trp Thr Gly Leu Arg Asp Leu Asn Gly Asn Ile Met Gln
1               5                   10                  15

Glu Ser Leu Phe Ser Pro Ala Trp Lys Thr Leu Leu Leu Glu Gln Pro
            20                  25                  30

Gln Ser Gln Thr Asn Val Leu Val Ser Leu
        35                  40
```

(2) INFORMATION FOR SEQ ID NO:28:

(i) SEQUENCE CHARACTERISTICS:
        (A) LENGTH: 42 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

```
Glu Ser Met Ser Ala Tyr Asp Gln Thr Leu Ser Glu Cys Asn Arg Val
1               5                   10                  15
```

-continued

```
Lys Leu Leu Phe Gly Leu Tyr Gln Asn Pro Leu His Lys Ile Arg Gln
            20                  25                  30

Asp Gln Arg Ala Val Pro Leu Pro Ala Leu
            35                  40
```

(2) INFORMATION FOR SEQ ID NO:29:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

```
Gly Glu Pro Ala Ala Gly Tyr Val Ser His Glu Gly Tyr Ala Ala Leu
1               5                   10                  15

Ala Arg Ala Pro Tyr Arg Tyr Gln Glu Met Leu Gly Val Ile Trp Arg
            20                  25                  30

Glu Asn Pro Cys Arg Trp Leu Lys Pro Asp Glu Ser Pro Phe Leu Met
            35                  40                  45

Ala Thr
50
```

(2) INFORMATION FOR SEQ ID NO:30:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Thr Gln Ala Gly Pro His Gly Gly Asp Ser Leu Leu Val Ser Ala Val
1               5                   10                  15

Lys Arg Leu Ser Asp Arg Leu Gly Ile Thr Val Gln Gln Ala Ala His
            20                  25                  30

Ala Trp Val Asp Ala Tyr Cys Gln Gln Val Leu Lys Pro Leu Phe Thr
            35                  40                  45

Ala Glu
50
```

(2) INFORMATION FOR SEQ ID NO:31:

(i) SEQUENCE CHARACTERISTICS:
        (A) LENGTH: 42 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
Leu Thr Asp Ser Pro Cys Ser Asn Thr Pro Leu Leu Ile Glu Ile Ile
1               5                   10                  15

Lys Ala Ser Gly Leu His Pro Thr Thr Tyr Phe Thr Glu Tyr Cys Tyr
            20                  25                  30

Lys Met Leu Phe Gly Gln Leu His Leu Leu
            35                  40
```

(2) INFORMATION FOR SEQ ID NO:32:

(i) SEQUENCE CHARACTERISTICS:
    (A) LENGTH: 42 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:32:

```
Leu Met Glu Trp Asp Glu Asn Asn Gln Pro Leu Ala Gly Ala Tyr Ile
1               5                   10                  15
Asp Arg Ser Gly Leu Asp Ala Glu Thr Trp Leu Thr Gln Leu Phe Arg
            20                  25                  30
Val Val Val Val Pro Leu Tyr His Leu Leu
        35                  40
```

(2) INFORMATION FOR SEQ ID NO:33:

(i) SEQUENCE CHARACTERISTICS:
        (A) LENGTH: 49 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
Ala Asp Tyr Gly Leu Val Leu Ala His Gln Gln Asn Ile Leu Val
1               5                   10                  15
Gln Met Leu Gly Asp Leu Pro Val Gly Phe Ile Tyr Arg Asp Cys Gln
            20                  25                  30
Gly Ser Ala Phe Met Pro His Ala Thr Glu Trp Leu Asp Thr Ile Asp
            35                  40                  45
Glu
```

(2) INFORMATION FOR SEQ ID NO:34:

(i) SEQUENCE CHARACTERISTICS:
        (A) LENGTH: 47 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

```
Leu Lys Tyr Gly Leu Ala Leu Glu Val Glu Gln His Asn Ile Leu Val
1               5                   10                  15
Ile Phe Asp Asp Asn Lys Pro Gln Gly Ile Ile Ile Lys Glu Pro Asn
            20                  25                  30
Asn Leu Lys Leu Cys Asn His Glu Leu Phe Lys Asn Val Gln Lys
            35                  40                  45
```

(2) INFORMATION FOR SEQ ID NO:35:

(i) SEQUENCE CHARACTERISTICS:
        (A) LENGTH: 42 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
Cys Arg Tyr Gly Val Ala Leu Ile Ala His Gly Gln Asn Ile Thr Leu
```

```
                1               5                    10                       15
Ala Met Lys Glu Gly Val Pro Gln Arg Val Leu Leu Lys Asp Phe Gln
                          20                   25                   30

Gly Asp Met Arg Leu Val Lys Glu Glu Phe
            35                   40
```

(2) INFORMATION FOR SEQ ID NO:36:

(i) SEQUENCE CHARACTERISTICS:
        (A) LENGTH: 47 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

```
Ala Gln Ala Glu Asn Ile Phe Thr Arg Glu Gln Leu Leu Arg Tyr Phe
1               5                   10                  15

Pro Tyr Tyr Leu Leu Val Asn Ser Thr Phe Ala Val Thr Ala Ala Leu
                20                  25                  30

Gly Ala Ala Gly Leu Asp Ser Glu Ala Asn Leu Met Ala Arg Val
                35                  40                  45
```

(2) INFORMATION FOR SEQ ID NO:37:

(i) SEQUENCE CHARACTERISTICS:
        (A) LENGTH: 48 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

```
Pro Asn Ala Pro Asp Ser Leu Ser Ile Tyr Thr Lys Asp Leu Asn Gln
1               5                   10                  15

Val Arg Thr Leu Phe Ile Gln Gly Thr Leu Lys Asn His Leu His His
                20                  25                  30

Leu Ile Gly Cys Leu Arg Asn Glu Tyr Gln Ile Pro Ser Arg Thr Leu
                35                  40                  45
```

(2) INFORMATION FOR SEQ ID NO:38:

(i) SEQUENCE CHARACTERISTICS:
        (A) LENGTH: 45 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

```
Pro Glu Met Asp Ser Leu Pro Gln Glu Val Arg Asp Val Thr Ser Arg
1               5                   10                  15

Leu Ser Ala Asp Tyr Leu Ile His Asp Leu Gln Thr Gly His Phe Val
                20                  25                  30

Thr Val Leu Arg Phe Ile Ser Pro Leu Met Val Arg Leu
                35                  40                  45
```

(2) INFORMATION FOR SEQ ID NO:39:

(i) SEQUENCE CHARACTERISTICS:
        (A) LENGTH: 50 amino acids
        (B) TYPE: amino acid (C) STRANDEDNESS:
(D) TOPOLOGY: linear (ii) MOLECULE TYPE: peptide (xi) SEQUENCE DESCRIPTION: SEQ ID NO:39:

Arg Thr Leu Leu Ala Glu Val Arg Asp Gln Val Thr His Lys Thr Cys
1               5                   10                  15
Leu Asn Tyr Val Leu Glu Ser Pro Tyr Trp Asn Val Lys Gly Asn Phe
                20                  25                  30
Phe Cys Tyr Leu Asn Asp His Asn Glu Asn Thr Ile Val Asp Pro Ser
            35                  40                  45
Val Ile
50

(2) INFORMATION FOR SEQ ID NO:40:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

Trp Gly Leu Ala Arg Gln Val Met Gln Thr Val Phe Lys Asp Leu Ser
1               5                   10                  15
Lys Asp Ile Asp Pro Arg Ile Leu Ser Trp Gln His Leu Leu Leu
                20                  25                  30
His Asp Asn Trp Glu His Gln Pro Glu Leu Leu Leu Ser Leu His Ser
            35                  40                  45
Lys Ile
50

(2) INFORMATION FOR SEQ ID NO:41:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

Gly Val Pro Glu Arg Arg Phe Tyr Gln Leu Leu Ala Ala Val Leu Ser
1               5                   10                  15
Asp Tyr Met Lys Lys His Pro Gln Met Ser Glu Arg Phe Ala Leu Phe
                20                  25                  30
Ser Leu Phe
        35

(2) INFORMATION FOR SEQ ID NO:42:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

Tyr Phe Asp Phe Ala Asn Pro Leu Gln Ala Gln Glu Val (2) INFORMATION FOR SEQ ID NO:43:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Asn Arg Asn Ile Thr Ile Lys Glu Tyr Asn Pro Leu Ser Glu Ile
1               5                  10                  15
```

(2) INFORMATION FOR SEQ ID NO:44:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

```
Arg Pro Gln Ile Ile Arg Val Val Leu Asn Pro
1               5                  10
```

(2) INFORMATION FOR SEQ ID NO:45:

(i) SEQUENCE CHARACTERISTICS:
        (A) LENGTH: 653 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:45:

```
GAAAAATATC CTTATAAATA TGAATTAGCC ATTGCATATG GCAAAAGATA ATCTGAAACA        60

ATTCCCGACA ACATCCTTTT AAAACGGTTG CAACTGAAAA TTCAACTTGT TAGTCTTTTG       120

AAGATTTTTA ACTGCTAAGT AACAAGGAGA AGTAAC ATG ATG TTG AAA ACC CAG        174
                                        Met Met Leu Lys Thr Gln
                                          1               5

TTG ACT GCT TTT ATC GGT GCT GTA ATC TTG GCT GGC TCT TCT TTA GCA        222
Leu Thr Ala Phe Ile Gly Ala Val Ile Leu Ala Gly Ser Ser Leu Ala
            10                  15                  20

AAT CCA ATA AAA CCT GAG GTA TGC CCC AGT GTA CCC TCT ATT CAA TCG        270
Asn Pro Ile Lys Pro Glu Val Cys Pro Ser Val Pro Ser Ile Gln Ser
        25                  30                  35

GAA GGA ATG TCC ATG TCT TCT GAA ATT TTG GAG GGC ATG TAC ATC ACC        318
Glu Gly Met Ser Met Ser Ser Glu Ile Leu Glu Gly Met Tyr Ile Thr
    40                  45                  50

TAT AAT TTA AGT CAT TAC AAT ACC AGT TCA AGC TGG GTG TTT ATT GTA        366
Tyr Asn Leu Ser His Tyr Asn Thr Ser Ser Ser Trp Val Phe Ile Val
55                  60                  65                  70

GGG CCA ATC GCA GCT GAA AAT GAT GAT ATG GCA TTG GCA GAA AGC AAT        414
Gly Pro Ile Ala Ala Glu Asn Asp Asp Met Ala Leu Ala Glu Ser Asn
                75                  80                  85

AAA TTA CTT TCA ACC ATG TCA GGG TCT CCC CAT CCG GAA GAT GAT GGA        462
Lys Leu Leu Ser Thr Met Ser Gly Ser Pro His Pro Glu Asp Asp Gly
            90                  95                 100

GAA GGC AAT TGG ATA TGT CAG TAT ACG ACC AAA TCC AAA GAT ATT ATT        510
```

-continued

```
Glu Gly Asn Trp Ile Cys Gln Tyr Thr Thr Lys Ser Lys Asp Ile Ile
        105                 110                 115

GCA TTT GCC ATA GAA GCA GAT GAT ATG CTT TCT CCA TTG AAA ATG ATG      558
Ala Phe Ala Ile Glu Ala Asp Asp Met Leu Ser Pro Leu Lys Met Met
    120                 125                 130

AGA TAT CTC AGA ACA ATC CGC TGATAAGTGG ATAACACCTG CACGGACACG         609
Arg Tyr Leu Arg Thr Ile Arg
135                 140

GAAGCATGAT TTGCTTCCGT GATTTAACGA ATAGTTAAGA GCTC                     653

(2) INFORMATION FOR SEQ ID NO:46:

(i) SEQUENCE CHARACTERISTICS:
          (A) LENGTH: 141 amino acids
          (B) TYPE: amino acid
          (D) TOPOLOGY: linear (ii) MOLECULE TYPE: protein (xi) SEQUENCE DESCRIPTION: SEQ ID NO:46:

Met Met Leu Lys Thr Gln Leu Thr Ala Phe Ile Gly Ala Val Ile Leu
  1               5                  10                  15

Ala Gly Ser Ser Leu Ala Asn Pro Ile Lys Pro Glu Val Cys Pro Ser
             20                  25                  30

Val Pro Ser Ile Gln Ser Glu Gly Met Ser Met Ser Ser Glu Ile Leu
        35                  40                  45

Glu Gly Met Tyr Ile Thr Tyr Asn Leu Ser His Tyr Asn Thr Ser Ser
     50                  55                  60

Ser Trp Val Phe Ile Val Gly Pro Ile Ala Ala Glu Asn Asp Asp Met
 65                  70                  75                  80

Ala Leu Ala Glu Ser Asn Lys Leu Leu Ser Thr Met Ser Gly Ser Pro
                 85                  90                  95

His Pro Glu Asp Asp Gly Glu Gly Asn Trp Ile Cys Gln Tyr Thr Thr
            100                 105                 110

Lys Ser Lys Asp Ile Ile Ala Phe Ala Ile Glu Ala Asp Asp Met Leu
        115                 120                 125

Ser Pro Leu Lys Met Met Arg Tyr Leu Arg Thr Ile Arg
    130                 135                 140

(2) INFORMATION FOR SEQ ID NO:47:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Primer"

(xi) SEQUENCE DESCRIPTION: SEQ ID NO:47:

GATAATGATA ATCATTATC                                                  19
```